United States Patent
Devgon et al.

(10) Patent No.: US 9,744,344 B1
(45) Date of Patent: Aug. 29, 2017

(54) DEVICES AND METHODS FOR CATHETER PLACEMENT WITHIN A VEIN

(71) Applicant: Velano Vascular, Inc., San Francisco, CA (US)

(72) Inventors: Pitamber Devgon, Philadelphia, PA (US); Kevin J. Ehrenreich, San Francisco, CA (US); Richard T. Briganti, Bala Cynwyd, PA (US)

(73) Assignee: Velano Vascular, Inc., San Francisco, CA (US)

( * ) Notice: Subject to any disclaimer, the term of this patent is extended or adjusted under 35 U.S.C. 154(b) by 0 days.

(21) Appl. No.: 15/199,290

(22) Filed: Jun. 30, 2016

(51) Int. Cl.
*A61M 25/09* (2006.01)
*A61M 39/22* (2006.01)
*A61M 25/01* (2006.01)
*A61M 25/06* (2006.01)
*A61M 39/02* (2006.01)
*A61B 5/15* (2006.01)
*A61M 25/00* (2006.01)
*A61B 8/08* (2006.01)

(52) U.S. Cl.
CPC ... *A61M 39/0247* (2013.01); *A61B 5/150992* (2013.01); *A61B 8/0891* (2013.01); *A61M 25/0097* (2013.01); *A61M 2039/0202* (2013.01); *A61M 2039/027* (2013.01); *A61M 2039/0258* (2013.01); *A61M 2039/0282* (2013.01)

(58) Field of Classification Search
CPC .......... A61B 5/15003; A61B 5/150839; A61B 5/150992; A61B 5/153
See application file for complete search history.

(56) References Cited

U.S. PATENT DOCUMENTS

| | | |
|---|---|---|
| 4,192,319 A | 3/1980 | Hargens et al. |
| 4,790,830 A | 12/1988 | Hamacher |

(Continued)

FOREIGN PATENT DOCUMENTS

| | | |
|---|---|---|
| EP | 2504054 | 9/2013 |
| WO | WO 96/21393 | 7/1996 |

(Continued)

OTHER PUBLICATIONS

Office Action for U.S. Appl. No. 13/456,900, mailed Sep. 5, 2012.

(Continued)

*Primary Examiner* — Michael C Stout
(74) *Attorney, Agent, or Firm* — Cooley LLP

(57) ABSTRACT

An apparatus includes an introducer defining a lumen and a catheter movably disposed in the lumen. The introducer has a distal end portion configured to operably couple to an indwelling peripheral intravenous line at least partially disposed in a vein. The catheter is configured to be moved between a first position, in which the catheter is proximal to the peripheral intravenous line when the introducer is operably coupled thereto, and a second position, in which a distal surface of the catheter is distal to the introducer and disposed at a predetermined distance from a distal tip of the peripheral intravenous line. The predetermined distance defined between the distal surface of the catheter and the distal tip of the peripheral intravenous line is based at least in part on a venous anatomy associated with the vein.

25 Claims, 49 Drawing Sheets

(56) References Cited

U.S. PATENT DOCUMENTS

| | | | |
|---|---|---|---|
| 4,808,158 A | 2/1989 | Kreuzer et al. | |
| 4,935,010 A * | 6/1990 | Cox | A61M 39/045 |
| | | | 604/122 |
| 5,013,304 A | 5/1991 | Russell et al. | |
| 5,100,390 A | 3/1992 | Lubeck et al. | |
| 5,135,502 A | 8/1992 | Koenig, Jr. et al. | |
| 5,147,334 A | 9/1992 | Moss | |
| 5,201,722 A | 4/1993 | Moorehead et al. | |
| 5,203,771 A | 4/1993 | Melker et al. | |
| 5,270,003 A | 12/1993 | Bernes et al. | |
| 5,360,407 A | 11/1994 | Leonard | |
| 5,368,029 A | 11/1994 | Holcombe et al. | |
| 5,552,118 A | 9/1996 | Mayer | |
| 5,553,625 A | 9/1996 | Rao | |
| 5,562,631 A | 10/1996 | Bogert | |
| 5,611,782 A | 3/1997 | Haedt | |
| 5,658,263 A | 8/1997 | Dang et al. | |
| D384,741 S | 10/1997 | Musgrave et al. | |
| 5,713,876 A | 2/1998 | Bogert et al. | |
| 5,749,857 A | 5/1998 | Cuppy | |
| 5,755,709 A | 5/1998 | Cuppy | |
| 5,827,229 A | 10/1998 | Auth et al. | |
| 5,848,996 A | 12/1998 | Eldor | |
| 5,853,393 A | 12/1998 | Bogert | |
| 5,897,537 A | 4/1999 | Berg et al. | |
| 5,911,715 A | 6/1999 | Berg et al. | |
| 5,944,695 A | 8/1999 | Johnson et al. | |
| 6,036,677 A | 3/2000 | Javier et al. | |
| 6,059,759 A | 5/2000 | Mottola et al. | |
| 6,080,138 A | 6/2000 | Lemke et al. | |
| 6,093,177 A | 7/2000 | Javier et al. | |
| 6,126,618 A | 10/2000 | Bischof | |
| 6,197,001 B1 | 3/2001 | Wilson et al. | |
| 6,648,835 B1 | 11/2003 | Shemesh | |
| 6,652,507 B2 | 11/2003 | Pepin | |
| 6,685,664 B2 * | 2/2004 | Levin | A61M 1/34 |
| | | | 210/321.6 |
| 6,692,473 B2 | 2/2004 | St. Cyr et al. | |
| 6,712,790 B1 | 3/2004 | Prestidge et al. | |
| 6,719,726 B2 | 4/2004 | Meng et al. | |
| 6,719,781 B1 | 4/2004 | Kim | |
| 6,722,370 B1 * | 4/2004 | Mann | A61M 25/10 |
| | | | 128/898 |
| 6,755,812 B2 | 6/2004 | Peterson et al. | |
| 6,858,024 B1 | 2/2005 | Berg et al. | |
| 6,908,459 B2 | 6/2005 | Harding et al. | |
| 7,135,008 B2 | 11/2006 | O'Mahony et al. | |
| 7,252,654 B2 | 8/2007 | VanTassel et al. | |
| 7,311,689 B2 | 12/2007 | Levin et al. | |
| 7,316,678 B2 | 1/2008 | Nash et al. | |
| 7,462,161 B2 | 12/2008 | O'Mahony et al. | |
| 7,615,033 B2 | 11/2009 | Leong | |
| 7,625,367 B2 | 12/2009 | Adams et al. | |
| 7,662,110 B2 | 2/2010 | Flaherty | |
| 7,670,320 B2 | 3/2010 | Iwase et al. | |
| 7,691,088 B2 | 4/2010 | Howell | |
| 7,713,250 B2 | 5/2010 | Harding et al. | |
| 7,717,882 B2 | 5/2010 | Harding | |
| 7,717,899 B2 | 5/2010 | Bowe et al. | |
| 7,762,977 B2 | 7/2010 | Porter et al. | |
| 7,766,961 B2 | 8/2010 | Patel et al. | |
| 7,771,394 B2 | 8/2010 | Shue et al. | |
| 7,892,208 B2 | 2/2011 | Schnell et al. | |
| 7,972,294 B2 | 7/2011 | Nash et al. | |
| 8,062,226 B2 | 11/2011 | Moore | |
| 8,092,374 B2 | 1/2012 | Smith et al. | |
| 8,104,475 B2 | 1/2012 | Cheung | |
| 8,114,057 B2 | 2/2012 | Gerdts et al. | |
| 8,251,978 B2 | 8/2012 | Nash et al. | |
| 8,267,911 B2 | 9/2012 | Gallogly et al. | |
| 8,361,013 B2 | 1/2013 | Wood | |
| 8,361,014 B2 | 1/2013 | Wood | |
| 8,366,685 B2 | 2/2013 | Devgon | |
| 8,372,032 B2 | 2/2013 | Wood | |
| 8,425,532 B2 | 4/2013 | Flom et al. | |
| 8,444,605 B2 | 5/2013 | Kuracina et al. | |
| 8,491,568 B2 | 7/2013 | Schertiger et al. | |
| 8,523,801 B2 | 9/2013 | Nash et al. | |
| 8,690,833 B2 | 4/2014 | Belson | |
| 8,696,639 B2 | 4/2014 | Smith et al. | |
| 8,702,658 B2 | 4/2014 | Spearman | |
| 8,721,546 B2 | 5/2014 | Belson | |
| 8,728,035 B2 | 5/2014 | Warring et al. | |
| 8,728,038 B2 | 5/2014 | Spearman | |
| 8,728,058 B2 | 5/2014 | Schertiger | |
| 8,753,312 B2 | 6/2014 | Bowe et al. | |
| 8,808,246 B2 | 8/2014 | Cabot | |
| 8,876,773 B2 | 11/2014 | Ishida | |
| 9,352,128 B2 | 5/2016 | Ishida | |
| 9,415,185 B2 | 8/2016 | Notter | |
| 2002/0120215 A1 | 8/2002 | Crawford et al. | |
| 2004/0092879 A1 | 5/2004 | Kraus et al. | |
| 2004/0138622 A1 | 7/2004 | Palasis | |
| 2004/0181192 A1 | 9/2004 | Cuppy | |
| 2005/0015048 A1 | 1/2005 | Chiu et al. | |
| 2005/0119597 A1 * | 6/2005 | O'Mahony | A61M 1/3413 |
| | | | 604/4.01 |
| 2005/0192558 A1 * | 9/2005 | Bernard | A61M 25/007 |
| | | | 604/525 |
| 2006/0015068 A1 | 1/2006 | Amisar et al. | |
| 2007/0219460 A1 | 9/2007 | Goldenberg | |
| 2007/0282280 A1 | 12/2007 | Tennican | |
| 2008/0033396 A1 | 2/2008 | Danek et al. | |
| 2008/0045862 A1 | 2/2008 | Dalebout et al. | |
| 2008/0287918 A1 | 11/2008 | Rosenman et al. | |
| 2008/0300574 A1 * | 12/2008 | Belson | A61M 25/0606 |
| | | | 604/510 |
| 2008/0319387 A1 | 12/2008 | Amisar et al. | |
| 2009/0156963 A1 | 6/2009 | Noble et al. | |
| 2010/0210934 A1 | 8/2010 | Belson | |
| 2010/0286657 A1 | 11/2010 | Heck | |
| 2010/0305519 A1 | 12/2010 | McKinnon et al. | |
| 2011/0015577 A1 | 1/2011 | Baney et al. | |
| 2012/0041392 A1 | 2/2012 | Donawick | |
| 2012/0046648 A1 | 2/2012 | Scheckel | |
| 2012/0053523 A1 | 3/2012 | Harding | |
| 2012/0109079 A1 | 5/2012 | Asleson et al. | |
| 2012/0191010 A1 * | 7/2012 | Cabot | A61B 5/154 |
| | | | 600/581 |
| 2012/0277627 A1 | 11/2012 | Devgon | |
| 2012/0277630 A1 * | 11/2012 | Devgon | A61B 5/1438 |
| | | | 600/581 |
| 2013/0289537 A1 | 10/2013 | Schertiger et al. | |
| 2014/0012085 A1 | 1/2014 | Smith et al. | |
| 2014/0046214 A1 | 2/2014 | Devgon | |
| 2014/0107800 A1 | 4/2014 | Flom et al. | |
| 2014/0128774 A1 | 5/2014 | Andreae et al. | |
| 2014/0128775 A1 | 5/2014 | Andreae et al. | |
| 2014/0171803 A1 | 6/2014 | Van Hoven et al. | |
| 2014/0180127 A1 | 6/2014 | Meyer et al. | |
| 2014/0188002 A1 | 7/2014 | Close et al. | |
| 2014/0188003 A1 | 7/2014 | Belson | |
| 2014/0296745 A1 | 10/2014 | Cash | |
| 2014/0343456 A1 | 11/2014 | Cabot | |
| 2014/0358120 A1 | 12/2014 | Haarala et al. | |
| 2014/0364766 A1 | 12/2014 | Devgon | |
| 2014/0378867 A1 | 12/2014 | Belson | |
| 2015/0005669 A1 | 1/2015 | Burkholz | |
| 2015/0148747 A1 | 5/2015 | Whitley | |
| 2015/0313526 A1 * | 11/2015 | Van Wieren | A61B 5/157 |
| | | | 600/347 |
| 2015/0360005 A1 | 12/2015 | Arellano et al. | |
| 2016/0022963 A1 | 1/2016 | Belson | |
| 2016/0073937 A1 * | 3/2016 | Burkholz | A61B 5/1405 |
| | | | 604/265 |
| 2016/0206858 A1 | 7/2016 | Ishida | |
| 2016/0220786 A1 * | 8/2016 | Mitchell | A61M 25/0029 |

(56) References Cited

U.S. PATENT DOCUMENTS

2016/0220790 A1 8/2016 Borowicz
2016/0256667 A1 9/2016 Ribelin et al.

FOREIGN PATENT DOCUMENTS

| WO | WO 00/41617 | 7/2000 |
|---|---|---|
| WO | WO 00/49939 | 8/2000 |
| WO | WO 2006/065949 | 6/2006 |
| WO | WO 2008/097949 | 8/2008 |
| WO | WO 2008/130077 | 10/2008 |
| WO | WO 2008/138351 | 11/2008 |
| WO | WO 2009/029216 | 3/2009 |
| WO | WO 2009/152470 | 12/2009 |
| WO | WO 2010/065901 | 6/2010 |
| WO | WO 2010/089154 | 8/2010 |
| WO | WO 2010/107949 | 9/2010 |
| WO | WO 2011/011436 | 1/2011 |
| WO | WO 2012/064786 | 5/2012 |
| WO | WO 2013/174381 | 11/2013 |
| WO | WO 2014/093472 | 6/2014 |
| WO | WO 2016/033143 | 3/2016 |

OTHER PUBLICATIONS

Office Action for U.S. Appl. No. 13/456,900, mailed Nov. 2, 2012.
International Search Report and Written Opinion for International Application No. PCT/US12/35122, mailed Feb. 14, 2014.
Supplementary European Search Report for European Application No. EP 12776089.0, mailed May 13, 2015, 7 pgs.
Office Action for Chinese Patent Application No. 201280029672.2, mailed May 26, 2015, 21 pgs.
Office Action for U.S. Appl. No. 13/234,857, mailed Apr. 16, 2015, 17 pgs.
Office Action for U.S. Appl. No. 13/758,585, mailed Jun. 10, 2015, 20 pgs.
Office Action for U.S. Appl. No. 13/758,585, mailed Oct. 30, 2015, 14 pgs.
Office Action for U.S. Appl. No. 13/758,585, mailed May 16, 2016, 8 pages.
Office Action for Japanese Patent Application No. 2014-508539, mailed Feb. 26, 2016, 4 pgs.
Office Action for Russian Patent Application No. 2013152251, mailed Feb. 24, 2016, 6 pgs.
International Search Report and Written Opinion for International Application No. PCT/US15/46863, mailed Dec. 21, 2015, 11 pgs.
Himberger Jr., "Accuracy of drawing blood through infusing intravenous lines," 2001 [retrieved on Mar. 16, 2011] Retrieved from the Internet <URL: <http://www.ncbi.nlm.nih.gov/pubmed/?term=Accuracy%20of%20drawing%20blood%20through%20infusing%20intravenous%20lines>.
Cox, et al. "Blood Samples Drawn from IV Catheters Have Less Hemolysis When 5-mL (vs 10-mL) Collection Tubes Are Used," 2004 [retrieved on Mar. 16, 2011] Retrieved from the Internet <URL: http://www.jenonline.org/article/S0099-1767(04)00634-8/fulltext> , 2 pgs.
Jagger, et al., "Drawing Venous Blood With Syringes: A Risky Use of Injection Equipment," Advances in Exposure Prevention, vol. 5, No. 3, 2000, 3 pgs.
WHO guidelines on drawing blood: best practices in phlebotomy, © World Health Organization 2010, 125 pgs.
"Connect and Protect with BD Diagnostics—Preanalytical Systems," BD Vacutainer®, Luer-Lok™, Access Device, 2 pgs.
"Needleless IV Access Devices," BD Q-Syte™, Luer Access Split-Septum, 2007, 1 pg.
"Evidence-Based Practice (EBP) Guideline Drawing Labs from Peripheral IV Sites," Nursing Research Council of United Hospital—Developed Apr. 2004; Revised Mar. 2009, 3 pgs.
Frey, "Drawing Blood Samples From Vascular Access Devices: Evidence-based Practice," Journal of Infusion Nursing: Sep./Oct. 2003, vol. 26, Issue 5, pp. 285-293, Article: CE, Abstract, [retrieved on Mar. 16, 2011], 1 pg.
"Blood Sampling Hemolysis Study for the MaxPlus™ Positive Flow Connector," Maximus Medical Products, Inc. © 2003, 1 pg.
"Vascular Access Procedures," Vascular Access Procedures, [retrieved on Mar. 16, 2011] Retrieved from the Internet <URL: http://www.radiologyinfo.org/en/info.cfm?pg=vasc_access> 7 pgs.
Hadaway, "Reopen the Pipeline," Nursing, vol. 5, No. 8, 2005, 11 pgs.
Kiray, et al., "Anatomical Evaluation of the Superficial Veins of the Upper Extremity as Graft Donor Source in Microvascular Reconstructions: A Cadaveric Study," Acta Orthopaedica et Traumatologica Turcica, vol. 47, No. 6, 2013; pp. 405-410.
Mikuni, et al., "Topographical Anatomy of Superficial Veins, Cutaneous Nerves, and Arteries at Venipuncture Sites in the Cubital Fossa," Anatomical Science International, vol. 88, 2013, pp. 46-57.
Iimura Akira, et al., "Anatomical Study of Distribution of Valves of the Cutaneous Veins of Adult's Limbs," Annals of Anatomy, vol. 185, 2003, pp. 91-95.
Office Action for Japanese Patent Application No. 2014-508539, mailed Nov. 1, 2016, 6 pgs.

\* cited by examiner

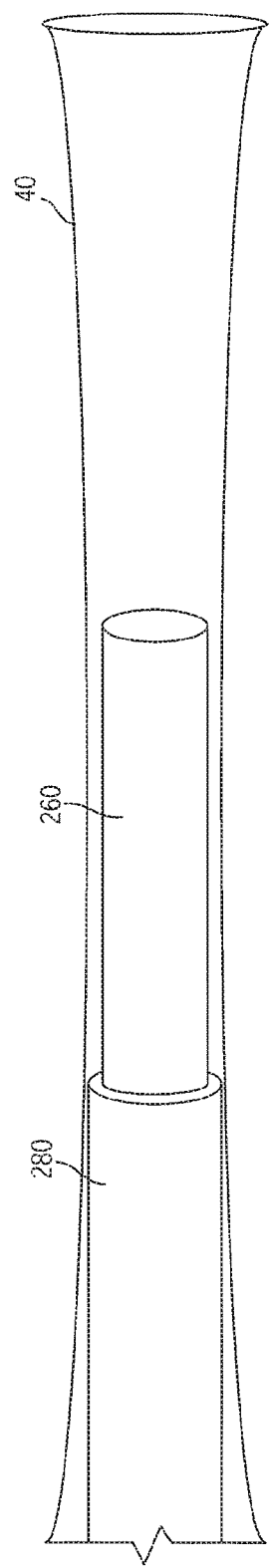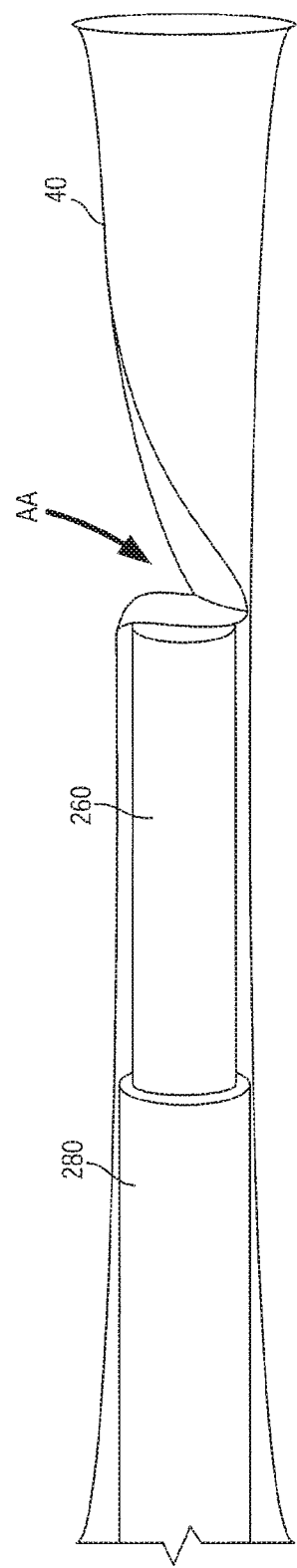
FIG. 6
FIG. 7

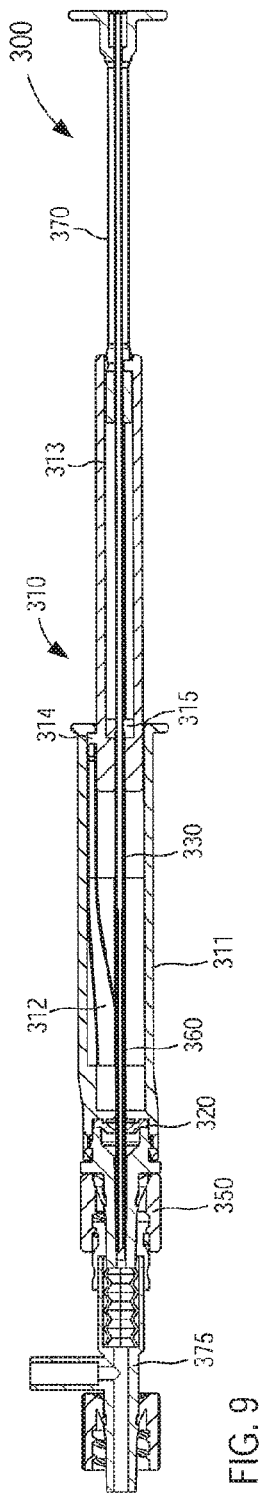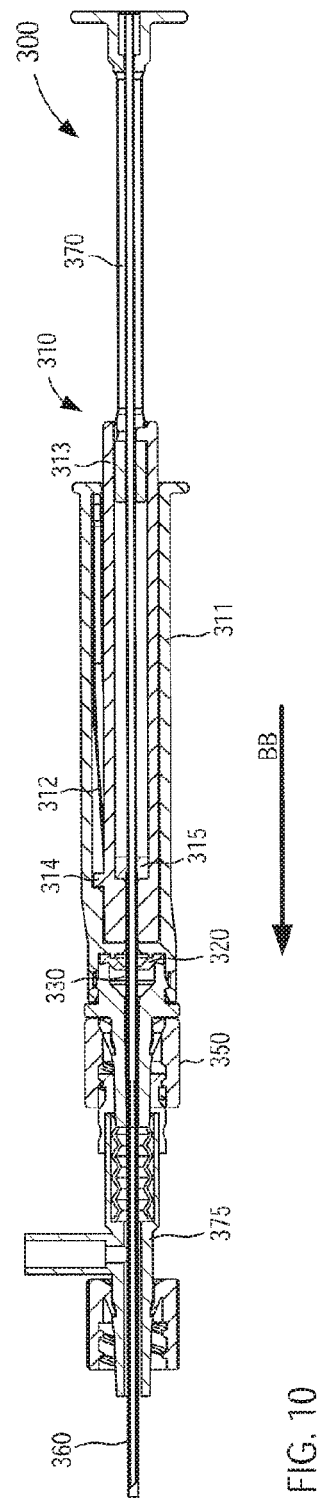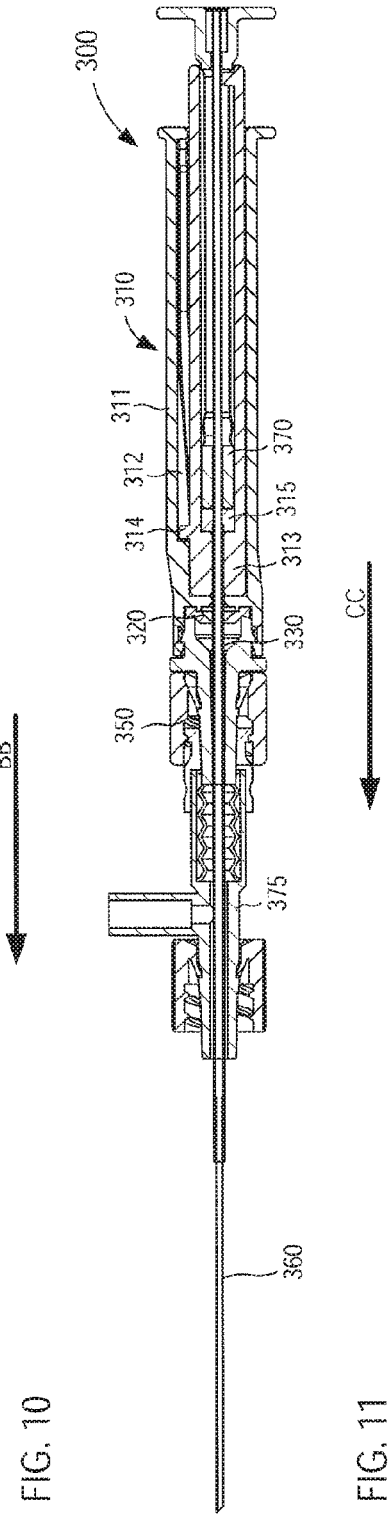

DEVICES AND METHODS FOR CATHETER PLACEMENT WITHIN A VEIN

BACKGROUND

The embodiments described herein relate generally to fluid transfer medical devices. More particularly, the embodiments described herein relate to devices and methods for placing a catheter within a vein, via an indwelling peripheral intravenous catheter, at a position suitable for blood aspiration.

The cutaneous veins of the forearm and hand are the most accessed sites for intravenous catheter insertions and venipunctures for infusing fluid into and/or aspirating bodily fluid from a patient. The standard procedure for blood extraction (i.e. phlebotomy), for example, involves percutaneous insertion of a metal needle ("butterfly needle") into a patient to gain access to that patient's vein. The typical hospitalized patient encounters a needle every time a doctor orders a lab test. Repeated needle "sticks" are not only painful and a major source of patient dissatisfaction, but can lead to significantly higher material and labor costs (needles and tubing must be disposed of after every attempt).

While most hospitalized patients receive a peripheral intravenous (PIV) catheter that is configured to dwell within a vein for an extended period, PIVs are generally used for infusing fluids and medications rather than blood extraction. In some instances, for example, the failure rates for aspiration reach 20-50% when a PIV has been indwelling (e.g., disposed in a vein) for more than a day. Blood extracted from PIVs is often hemolyzed (i.e., the red blood cells are often ruptured and their contents released), which can result in an unusable sample and a need to repeat the blood collection.

Several barriers can contribute to the shortcomings of extracting blood through a PIV. Such barriers can include, for example, catheter malfunctions, occlusion of the vein resulting from the indwelling of the PIV, debris forming around the PIV, collapse of the PIV or vein in response to the negative pressure during aspiration, and/or the like. In addition, the venous anatomy of the forearm and hand have not been well studied or described and, as such, the venous anatomy itself and/or characteristics of blood flow paths therethrough can further present barriers to phlebotomy through an indwelling PIV.

Thus, a need exists for improved understanding of the venous anatomy and for devices and methods for placing a catheter within a vein, via an indwelling PIV, at a position suitable for blood aspiration.

SUMMARY

Devices and methods for placing a catheter within a vein, via an indwelling peripheral intravenous catheter, at a position suitable for blood aspiration are described herein. In some embodiments, an apparatus includes an introducer and a catheter. The introducer has a distal end portion configured to be operatively coupled to an indwelling peripheral intravenous line at least partially disposed in a vein. The catheter is configured to be moved between a first position, in which the catheter is proximal to the peripheral intravenous line when the introducer is operably coupled thereto, and a second position, in which a distal surface of the catheter is distal to the introducer and disposed at a predetermined distance from a distal tip of the peripheral intravenous line. The predetermined distance defined between the distal surface of the catheter and the distal tip of the peripheral intravenous line is based at least in part on a venous anatomy associated with the vein.

BRIEF DESCRIPTION OF THE DRAWINGS

FIGS. 3-7 are schematic illustrations of a portion of a peripheral intravenous line and a portion of a blood aspiration catheter disposed within a portion of a vein, each of which having a different anatomic characteristic.

FIGS. 9-11 are each cross-sectional views of the fluid transfer device of FIG. 8 taken along the line 9-9 in the first configuration, a second configuration, and a third configuration, respectively.

DETAILED DESCRIPTION

Figure 1:
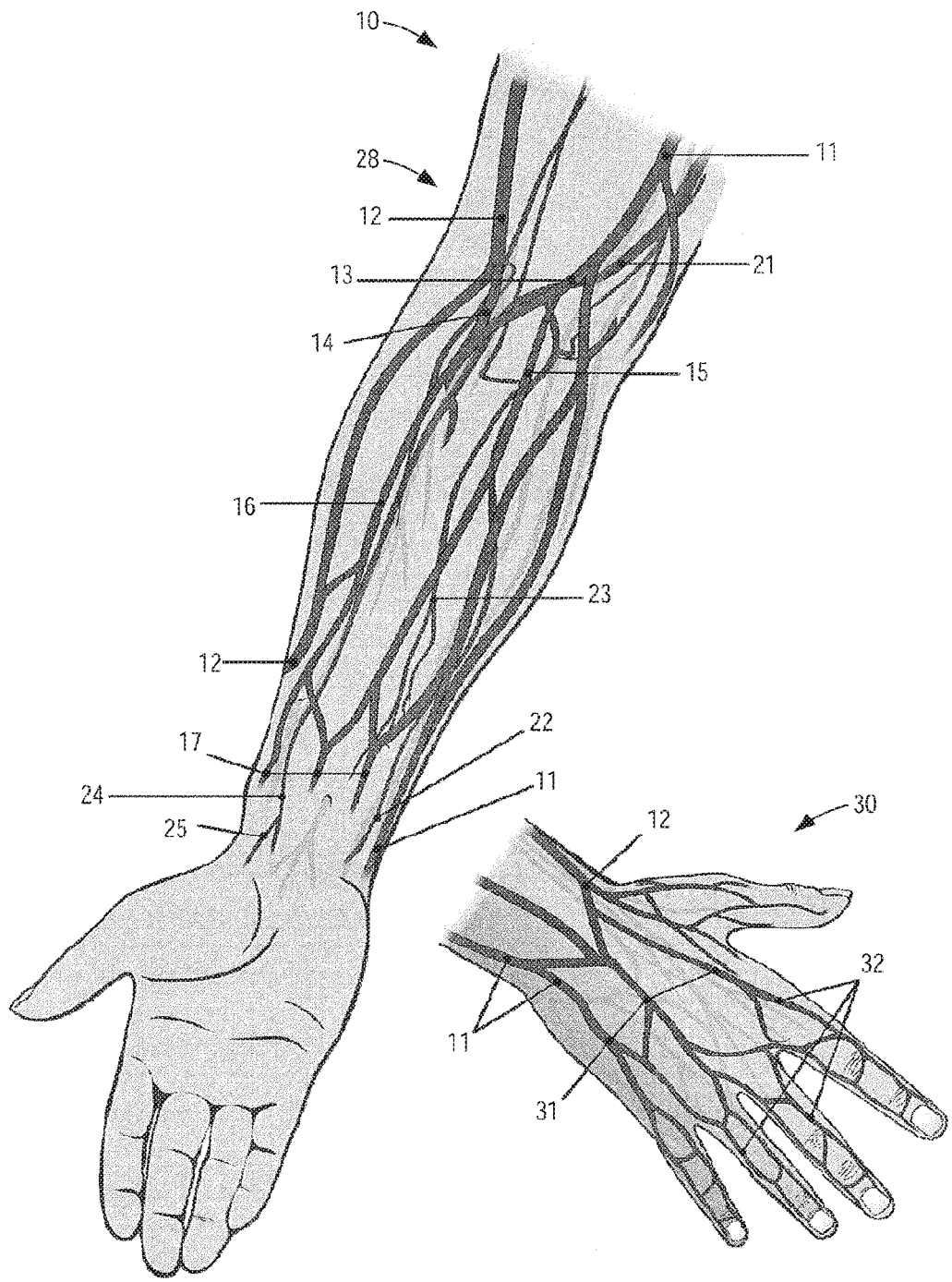
FIG. 1 is an illustration of a human forearm and human hand showing the vasculature thereof.

In some embodiments, an apparatus includes an introducer and a catheter. The introducer has a distal end portion configured to be operatively coupled to an indwelling peripheral intravenous line at least partially disposed in a vein. The catheter is configured to be moved between a first position, in which the catheter is proximal to the peripheral intravenous line when the introducer is operably coupled thereto, and a second position, in which a distal surface of the catheter is distal to the introducer and disposed at a predetermined distance from a distal tip of the peripheral intravenous line. The predetermined distance defined between the distal surface of the catheter and the distal tip of the peripheral intravenous line is based at least in part on a venous anatomy associated with the vein.

In some embodiments, an apparatus includes an introducer, a catheter, and an actuator. The introducer defines a lumen. A distal end portion of the introducer is configured to be operably coupled to an indwelling peripheral intravenous line at least partially disposed in a vein. The catheter has a proximal end portion and a distal end portion and defines a lumen extending through the proximal end portion of the catheter and the distal end portion of the catheter. At least a portion of the catheter is movably disposed in the lumen of the introducer. The actuator is movably coupled to the introducer. A portion of the actuator is disposed in the lumen and coupled to the proximal end portion of the catheter. The actuator is configured to be moved relative to the introducer to move the catheter between a first position, in which the catheter is proximal to the indwelling peripheral intravenous line when the introducer is operably coupled thereto, and a second position, in which a distal surface of the catheter is distal to the indwelling peripheral intravenous line and within the vein such that at least one of a valve of the vein or a branch vessel in fluid communication with the vein is disposed between a distal tip of the indwelling peripheral intravenous line and the distal surface of the catheter.

In some embodiments, a method includes coupling a fluid transfer device to an indwelling peripheral intravenous line at least partially disposed in a vein of a patient. The fluid transfer device includes at least a catheter configured to be moved relative to the indwelling peripheral intravenous line. The catheter is moved from a first position, in which the catheter is proximal to the indwelling peripheral intravenous line, to a second position, in which at least a portion of the catheter is disposed within the indwelling peripheral intravenous line such that a distal surface of the catheter is disposed at a predetermined distance from a distal tip of the indwelling peripheral intravenous line. The predetermined distance is based at least in part on a venous anatomy associated with the vein. A volume of blood is transferred via the catheter from the vein to a fluid reservoir in fluid communication with the catheter. The catheter is moved from the second position toward the first position after transferring a desired volume of blood to the fluid reservoir. The fluid transfer device is then decoupled from the indwelling peripheral intravenous line after moving the catheter from the second position toward the first position.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the value stated. For example, about 0.5 would include 0.45 and 0.55, about 10 would include 9 to 11, about 1000 would include 900 to 1100.

As used herein, the terms "catheter" and "cannula" are used interchangeably to describe an element configured to define a passageway for moving a bodily fluid from a first location to a second location (e.g., a fluid passageway to move a bodily fluid out of the body). While cannulas and/or catheters can receive a trocar, a guide wire, or an introducer to deliver the cannula and/or catheter to a volume inside the body of a patient, the cannulas and/or catheters referred to herein need not include or receive a trocar, guide wire, or introducer. Similarly, the terms "peripheral intravenous catheter" and "peripheral intravenous line" are used interchangeably to describe a device configured to percutaneously access a vein via venipuncture.

As used herein, the term "indwelling" when characterizing a catheter or the like generally refers to a catheter that is at least partially disposed within a portion of the body. For example, an "indwelling peripheral intravenous catheter" (also referred to as "indwelling peripheral intravenous line," "PIV catheter," "PIV line," or "PIV") can be a peripheral intravenous catheter that is percutaneously inserted into the body and at least partially disposed within a vein. In general, the methods of using the devices and/or embodiments described herein include gaining access to a vein of a patient via an indwelling peripheral intravenous catheter. In other words, the methods and/or embodiments described herein involve gaining access to a vein of a patient via a peripheral intravenous catheter previously inserted through the skin of the patient and partially disposed within the vein.

As used herein, the words "proximal" and "distal" when used in the context of a device refer to the direction closer to and away from, respectively, a user who would place the device into contact with a patient. Thus, for example, an end of the device first touching the body of the patient would be a distal end of the device, while an opposite end of the device (e.g., the end of the device being manipulated by the user) would be a proximal end of the device. The terms "proximal" and "distal" when used to describe a portion of the body refer to positions and/or directions closer to and away from, respectively, a central portion of the body. Thus, for example, a patient's hand is distal to the patient's forearm.

In some instances, the words "proximal" or "distal" can be relative terms and do not necessarily refer to universally fixed positions or directions. For example, a distal end portion of a peripheral intravenous (PIV) catheter is configured to be inserted into a vein of a patient's forearm while a proximal end portion of the PIV catheter can be substantially outside of the body. Veins, however, carry a flow of oxygen-poor blood from distal portions of the body back to the heart and, as a result, PIV catheters are generally inserted into a vein such that a distal tip of the PIV catheter is disposed within the vein in a position proximal to the insertion point (e.g., extending relative to the vein in a proximal direction). Thus, a distal position relative to the PIV catheter can refer to, for example, a proximal position relative to the vein (e.g., closer to the heart).

The devices and methods described herein can be used to advance a blood draw catheter at least partially through, for example, an indwelling PIV to place a distal end of the blood draw catheter in a desired position relative to a vein and/or the PIV. As used herein, the terms "predetermined distance" and "desired distance" generally refer to a distance defined between a distal end of a blood draw catheter and a distal end of a PIV in which the blood draw catheter is at least partially disposed. When describing a "predetermined distance" and/or a "desired distance" defined between the distal end of the catheter and the distal end of the IV, it should be understood that such a distance is within, for example, an acceptable range of predetermined distances. For example, an acceptable range of predetermined distances can be between, for example, 0.0 millimeters (mm) and about 50.0 mm. Thus, in some instances, a predetermined distance between a distal end of a first catheter and a distal end of a first PIV can be about 15.0 mm while in other instances, a predetermined distance between a distal end of a second catheter and a distal end of a second PIV can be above 30.0 mm. Furthermore, a predetermined distance can refer to a positive distance in which a distal end of a catheter is distal to a distal end of a PIV or a negative distance in which a distal end of a catheter is proximal to a distal end of a PIV.

The devices and methods described herein generally relate to the aspiration of blood from a vein of a patient, which is accessed via an indwelling peripheral intravenous (PIV) catheter. The cutaneous veins of the antecubital arm region, forearm, and hand are the most accessed sites for intravenous catheterization. For reference, FIG. 1 is illustrates a human forearm 10 and human hand 30 showing the vascular system thereof. While specific vascular structures are identified, it is to be understood that the proceeding identified regions do not constitute the entire vascular system of the forearm and/or hand; rather, the regions of the forearm 10 and the hand 30 are presented in FIG. 1 as a simplified example suitable for the discussion of the embodiments and methods herein. Moreover, it is to be understood that the vasculature represented in FIG. 1 is but one example and that while serving substantially the same function, the arrangement of an individual's vascular system in the forearm and hand can vary from what is shown in FIG. 1.

The venous system of the forearm 10 includes a basilic vein 11 and a cephalic vein 12, each of which extend distally to the hand 30. The basilic vein 11 and the cephalic vein each provide a flow of oxygen-depleted blood from distal portions of the hand 30 and forearm 10 to the vascular system of the upper arm (i.e., the subclavian vein, not shown). A median cubital vein 13 branches from the basilic vein 11 and establishes fluid communication between the basilic vein 11 and a median vein 15 as well as fluid communication between the basilic vein 11 and a median cephalic vein 16. Similarly, an accessory cephalic vein 14 joins the median cubital vein 13 to establish fluid communication between the cephalic vein 12 and the median cephalic vein 16. The median vein 15 and the median cephalic vein 16 branch collectively to form perforating or anastomotic veins 17. The basilic vein 11 and the cephalic vein 12 are each in fluid communication with the metacarpal veins 31 of the hand 30, which in turn, are in fluid communication with the dorsal digital veins 32. As shown in FIG. 1, the forearm 10 and the hand 30 can also include any number of veins and/or branches that combine or divide the veins into a fewer number of veins or a greater number of veins, respectively.

The arterial system of the forearm 10 includes a brachial artery 21 and an ulnar artery 22, each of which extend distally to the hand 30. The brachial artery 21 and the ulnar artery 22 each provide a fluid of oxygen-rich blood from the vascular system of the upper arm (i.e., the subclavian artery, not shown) to the distal portions of the forearm 10 and hand 30. The brachial artery 21 branches into a median artery 23 and a radial artery 24. The radial artery 24, in turn, branches into a metacarpal artery branch 25. The ulnar artery 22 and the metacarpal artery branch 25 supply oxygen-rich blood to the hand 30. As shown in FIG. 1, the forearm 10 and the hand 30 can also include any number of arteries and/or branches that combine or divide the arteries into a fewer number of arteries or a greater number of arteries, respectively.

Figure 2:
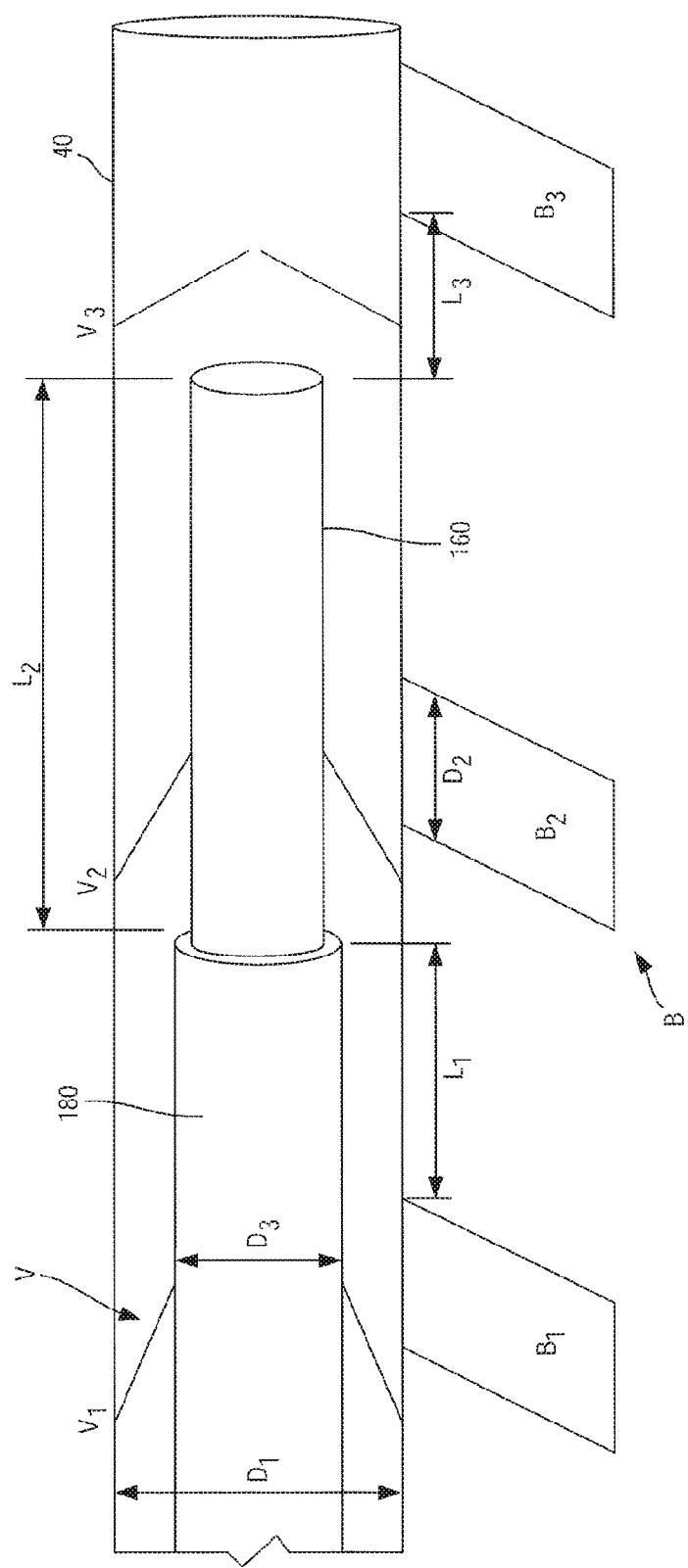
FIG. 2 is a schematic illustration of a portion of a peripheral intravenous line and a portion of a blood aspiration catheter disposed within a portion of a vein according to an embodiment.

FIG. 2 is a schematic illustration of a blood draw catheter 160 and a peripheral intravenous catheter 180 partially disposed within a vein 40 according to an embodiment. The vein 40 can be any suitable vein such as those included in the forearm or hand of a patient as described above with reference to FIG. 1. As shown, the vein 40 defines a lumen that includes a set of valves V1, V2, and V3. The vein 40 is in fluid communication with a set of branch vessels (veins) B1, B2, B3. While the vein 40 is particularly shown in FIG. 2, it should be understood that the arrangement of the vein 40 is presented by way of example and not limitation. Specifically, while the valves V1, V2, and V3, and the branch vessels B1, B2, B3 (also referred to herein as "branches") are shown in a particular arrangement relative to the vein 40, the arrangement illustrated in FIG. 2 is intended to present a general schematic of known anatomic structures of the vascular system. While the vascular structures are schematically presented with reference to FIG. 2, specific characterizations and/or data associated with these structures—at least as it relates to blood draw via catheterization through a peripheral intravenous catheter dwelling therein—is/are described in further detail hereinbelow.

The valves V1, V2, and V3 (referred to collectively as "valves V") disposed within the lumen of the vein 40 substantially control the flow of blood through the lumen. Any of the valves V, for example, can transition from a closed configuration to an open configuration to allow a selective flow of blood therethrough. When referring to the valve(s) V and/or any other valve(s) described herein it should be understood that the valve(s) can be anatomic structures within the vein or can be any other suitable form of flow control serving a function similar to anatomical valves and/or acting in a valve-like manner to obstruct and/or control blood flow in one or more directions. For example, a vein can include any number of anatomical valves formed of tissue and disposed in a given position within the vein. Such a valve(s) typically control a flow of blood within the vein in a single direction (e.g., in a proximal direction or in a direction toward the heart). In other words, valves generally limit and/or substantially prevent a backflow of blood within the vein (e.g., in a distal direction or in a direction away from the heart).

In other instances, however, an event can trigger or otherwise can result in a valve-like response within a portion of the vein that can selectively control a flow of blood through that portion. For example, in some instances, a vasospasm of a portion of the vein can result in a constriction of a lumen defined by the portion of the vein sufficient to restrict and/or otherwise limit a flow of blood therethrough (e.g., in a proximal and/or a distal direction). In such instances, a relaxing of the portion of the vein after the vasospasm can result in a dilation of the vein and/or otherwise a return to a non-spastic arrangement, which in turn, removes the limitation on the blood flow resulting from the vasospasm. As such, the occurrence of a vasospasm along a portion of a vein can effectively result in a valve-like response (albeit in a proximal and/or distal direction) within that portion of the vein sufficient to selectively control (e.g., limit or obstruct) a flow of blood therethrough. In some instances, the presence of a catheter within the vein and/or a contact between a portion of the catheter and a portion of the vein wall can result in a vasospasm of at least a portion of the vein. In other instances, a vein, debris (e.g., thrombus), muscle response, constriction, and/or any other structure, event, and/or response can act in a valve-like function within the vein and/or can otherwise restrict a flow of blood through the vein (e.g., in a proximal and/or distal direction within the vein). By way of example, the flexing of a muscle, the bending of a joint or appendage (e.g., elbow, arm, fingers, etc.), the presence of an externally applied force (e.g., pressure applied by a blood pressure cuff, pressure applied by a medical professional's hand or finger(s), pressure applied by an ultrasound probe), coughing or valsalva resulting in a temporary reversal of blood flow, injection of substances resulting in vaso-inflammation, and/or the like. Thus, the devices and methods described herein can be configured and/or used to insert a blood draw catheter (e.g., the blood draw catheter 160) into a vein (e.g., the vein 40) and to advance the blood draw catheter to a position within the vein that is beyond and/or through any of the flow restrictions described above, thereby placing the blood draw catheter in a position within the vein that receives a substantially unrestricted flow of blood, as described in further detail herein.

In some instances, one or more of the valves V can transition between an open or closed configuration to, for example, divert a flow of blood through a branch or the like. In some instances, compartments defined between two adjacent valves in the closed configuration can result in a significantly reduced flow of blood through that compartment. In some instances, a flow of blood can enter and/or exit a compartment defined by adjacent closed valves via one or more branch vessels. The vascular system of a person can include multiple veins that can branch from the vein 40 and/or join the vein 40, thereby forming a bypass or the like that can define a flow path within which blood can flow around occlusions of the vein 40 (see e.g., FIG. 1).

The flow characteristics associated with the vein 40 are based at least in part on the arrangement of the vascular structure thereof and/or in fluid communication therewith. For example, as shown in FIG. 2, the vein 40 has a diameter D1 and each of the branches B1, B2, and B3 (collectively referred to as "branches B") has a diameter D2. In some instances, the volumetric flow rate of blood through the vein 40 can be based at least in part on the diameter D1 of the vein 40. Similarly, the volumetric flow rate of blood through the vein 40 can be based on the diameter D2 of the branches B, in which branches with a smaller diameter deliver a smaller volume of blood to the vein 40 and branches with a larger diameter deliver a larger volume of blood to the vein. Thus, when the branches B in fluid communication with the vein 40 have a larger diameter D2, the volumetric flow rate through the vein 40 is greater than when the branches B have a smaller diameter. Although the branches B1, B2, and B3 are shown in FIG. 2 as having the same diameter, it should be understood that the diameter of each branches B1, B2, or B3 can vary. As such, the vein 40 and/or compartments of the vein 40 defined between adjacent valves V can have localized areas of higher or lower volumetric flow rates.

As described above, a portion of the peripheral intravenous catheter 180 and a portion of the blood draw catheter 160 are disposed in the lumen of the vein 40. The peripheral intravenous catheter 180 (also referred to herein as "peripheral intravenous line" or simply "PIV") can be any suitable peripheral intravenous catheter such as any suitable known PIV. The PIV 180 can have any suitable length between a hub (not shown) and a distal surface of the PIV catheter. For example, the length can be between about 19 millimeters (mm) (about 0.75 inches (in)) and about 45 mm (about 1.75 in). Similarly, the PIV 180 can have any suitable diameter D3. For example, the diameter D3 can be between about 26-gauge (or about 0.45 mm) and about 14-gauge (or about 2.0 mm). In some of the embodiments described herein, the PIV 180 can be a Jelco® 1.0 in, 20-gauge catheter manufactured by Smiths Medical, St. Paul, Minn., USA (referred to herein as "Jelco® 1.0 in, 20-gauge catheter" or "Jelco® 1.0 in, 20-gauge PIV").

In use, the size of the PIV 180 is generally based, at least in part, on a size of the vein in which the PIV 180 will be disposed. For example, in some instances, the PIV 180 is inserted into a portion of the basilic vein 11 of the forearm 10 (see FIG. 1). In some such instances, a diameter of the portion of the basilic vein 11 (e.g., the diameter D1 of the vein 40) can be sufficiently large to use, for example, a 20-gauge PIV (e.g., the diameter D3 of the PIV 180). In other instances, such as when the PIV 180 is inserted into a portion of a vein of the hand (e.g., the metacarpal vein 31 of the hand 30 in FIG. 1), the diameter of the vein (e.g., the diameter D1 of the vein 40) can preclude the use of a PIV with a diameter larger than, for example, 26-gauge or 24-gauge.

In some instances, the positioning of the portion of the PIV 180 within the vein 40 results in at least a partial occlusion of the lumen of the vein 40. That is to say, the presence of the PIV 180 within the vein reduces and/or restricts a flow of blood around the PIV 180. For example, as shown in FIG. 2, the PIV 180 can be inserted into the vein 40 such that a distal end portion is disposed in a compartment defined between the valve V1 (e.g., a proximal valve) and the valve V2 (e.g., a distal valve), which in turn, receives a limited flow of blood due to the presence of the PIV 180. In some instances, the distal surface of the PIV 180 (also referred to as the "distal tip") can be distal to the branch B1 and spaced apart from the branch B1 by a distance or length L1. In other instances, the distal surface of the PIV 180 can be proximal to the branch B1. In some instances, the flow of blood through the compartment can be reduced despite the compartment receiving a flow of blood from the branch B1 (FIG. 2) and/or regardless of the position of the distal surface of the PIV 180 relative to the branch B1. In some instances, the flow of blood into the compartment can be reduced by about 10%, about 20%, about 30%, about 40%, about 50%, about 60%, about 70%, about 80%, about 90%, or about 99%. In other instances, the presence of the PIV 180 can restrict the flow of blood through the compartment by 100%. In still other instances, the presence of the PIV 180 can restrict the flow of blood through the compartment by less than 10%.

In general, peripheral intravenous catheters such as the PIV 180 are used to infuse fluids into the body and are not used to aspirate blood because of, for example, low blood return levels, debris surrounding the distal tip of the PIV, kinks in the PIV, hemolysis of blood samples, vein collapse, and/or the like. As shown in FIG. 2, however, the blood draw catheter 160 (also referred to herein as "catheter") can be inserted through a lumen defined by the PIV 180 and used to aspirate blood. The catheter 160 can be any suitable size that is based at least in part on the size of the PIV 180. For example, the catheter 160 can have a diameter that is smaller than an inner diameter of the PIV 180, thereby allowing the catheter 160 to be inserted therethrough.

The catheter 160 can be positioned at a predetermined distance or length L2 from the distal surface of the PIV 180. As described in further detail herein, the distance or length L2 between the distal tip of the PIV 180 and a distal surface of the catheter 160 can be based at least in part on information associated with the vascular structure of the vein 40 (e.g., number and position of valves, number and position of branches, diameter of the vein 40 or branches B, etc.). In some instances, the length L2 can be sufficient to dispose the distal surface of the catheter 160 in a compartment defined between the valve V2 and the valve V3. That is to say, the distal surface of the catheter 160 can be disposed in a compartment of the vein 40 that is distal to the compartment in which the distal tip of the PIV 180 is disposed, as shown in FIG. 2. In some instances, the distal surface of the catheter 160 can be disposed in a position within the vein 40 having a volumetric flow rate that is greater than a volumetric flow rate through the compartment in which the distal tip of the PIV 180 is disposed. In this manner, the catheter 160 can be used to aspirate a volume of blood.

In some instances, the distal surface of the catheter 160 can be disposed at a distance or length L3 from the branch B3, as shown in FIG. 2. In some instances, the distance or length L3 can be a "buffer zone" or the like. As described in further detail herein, in some instances, it may be desired to reduce the distance or length L3 of the buffer zone to increase a likelihood of a successful blood draw through the catheter 160. In other instances, the distance of length L3 of the buffer zone may not substantially impact the likelihood of a successful blood draw. Similarly, while the distal surface of the catheter 160 is shown in FIG. 2 as being proximal to the valve V3 in other instances the catheter 160 can be positioned such that the distal surface of the catheter 160 is distal to the valve V3. Thus, the placement of the catheter 160 within the vein 40 and relative to the PIV 180 can increase or decrease a likelihood of successful blood draw therethrough, as described in further detail herein. In some instances, for example, it can be desirable to position the distal surface of the catheter 160 between about 1.0 in and about 1.25 in from the distal tip of the PIV 180, as described in further detail herein.

While the vein 40 is shown in FIG. 2 as having a number of valves V and branches B, a catheter can be inserted through a peripheral intravenous line at least partially dwelling in a vein having any suitable anatomical features and/or structures. In general, the vascular structures of a person vary, at least slightly, from the vascular structures of other people. The varying vascular structures, in some instances, can impact the size, shape, arrangement, and/or efficacy of blood aspiration via a PIV and/or via standard phlebotomy methods. Thus, as described in further detail herein, determining characteristics of vascular structures and providing devices having a configuration based at least in part on the characteristics of the vascular structures, in some instances, can result in an increased success rate associated with blood aspiration in general, and more specifically, with blood aspiration through an indwelling PIV.

FIGS. 3-6 are schematic illustrations of a blood draw catheter 260 and a peripheral intravenous catheter 280 partially disposed within a vein 40 according to an embodiment. The blood draw catheter 260 (also referred to herein as "catheter") and the peripheral intravenous catheter 280 (also referred to herein as "peripheral intravenous line" or simply "PIV") can be any suitable catheter device or devices. For example, in some embodiments, the catheter 260 and the PIV 280 can be substantially similar to the catheter 160 and the PIV 180, respectively, described above with reference to FIG. 2. In some embodiments, the catheter 260 can be included in a fluid transfer device such as those described in further detail herein. In some embodiments, the PIV 280 can be, for example, a standard, commercially available peripheral intravenous catheter such as a Jelco® 1.0 inch, 20-gauge catheter (as described above with reference to the PIV 180). As such, the catheter 160 and the PIV 180 are not described in further detail herein.

Figure 3:
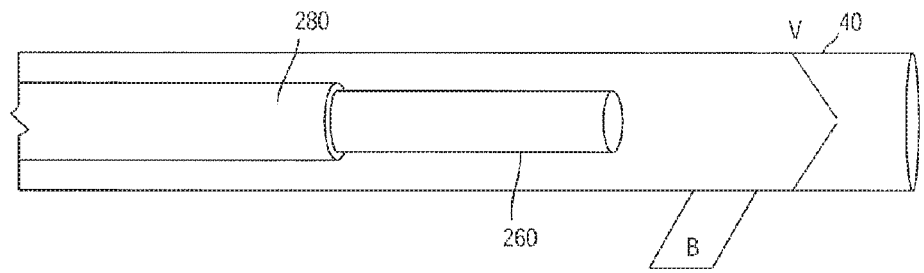

As shown in FIG. 3, in some instances, the PIV 280 can be inserted into and/or can be otherwise dwelling within a vein 40 having a branch vessel B in fluid communication with the vein 40 and a valve V formed proximally (e.g., downstream) of the branch vessel B. That is to say, the arrangement of the catheter 260, PIV 280, and vein 40 is such that the branch vessel B is between a distal end portion of the catheter 260 and the valve V. In some instances, the presence of the PIV 280 and/or catheter 260 within the vein 40 can result in a blockage and/or occlusion of the vein 40 distal to the PIV insertion point, which in some instances, can result in an at least partial reduction in volumetric flow rate of the blood therethrough. In some instances, the branch vessel B (also referred to as "branch") can provide an inlet flow of blood into the vein 40. Thus, in this arrangement, the distal end of the catheter 260 can be disposed in a portion of the vein 40 receiving a flow of blood from the branch B that is sufficient for blood aspiration through the catheter 260.

While the flow of blood through the branch B is generally an inlet flow of blood (e.g., a flow of blood from a distal position to a proximal position of the branch and/or vein 40 and/or otherwise in the direction of the heart), in some instances, the branch vessel B can receive an outlet flow of blood from the vein 40. In some such instances, a negative pressure resulting from aspiration through the catheter 260 can be sufficient to draw a volume of blood into the catheter 260 despite the outlet flow of blood from the vein 40 to the branch B. In other instances, the outlet arrangement of the branch B can result in a portion and/or compartment of the vein 40 being unsuitable for aspiration. In such instances, a nurse, technician, phlebotomist, doctor, etc. can move the catheter 260 (e.g., relative to the PIV 280 and the vein 40) to place the distal tip of the catheter 260 in a different portion and/or compartment of the vein 40 that is otherwise suitable for aspiration. Thus, relocating the catheter 260 relative to the PIV 280 can place the catheter 260 in fluid communication with a portion of the vein 40 receiving a flow of blood sufficient for aspiration through the catheter 260 while maintaining access to the vein 40 via the indwelling PIV 280. In other words, the catheter 260 can be relocated without performing a venipuncture otherwise used to access the vein 40.

Figure 4:
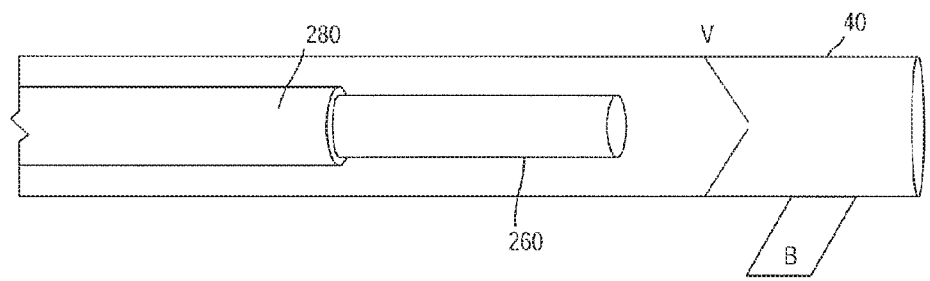

In some instances, the reduction in blood flow past the PIV 280 resulting from the at least partial occlusion of the vein 40 can be such that the success of aspirating a volume of blood is at least partially dependent on the flow of blood from or through the branch B. That is to say, in some instances, the absence of the branch B can otherwise result in a volumetric flow rate within the portion of the vein that is insufficient for blood aspiration through the catheter 260. For example, FIG. 4 illustrates the PIV 280 and the catheter 260 dwelling within a vein 40 having a valve V disposed between a distal tip of the catheter 260 and a branch vessel B. In some instances, a volumetric flow rate associated with a compartment of the vein 40 defined between, for example, a PIV insertion site and the valve V (e.g., in which the distal tip of the catheter 260 is disposed) can be insufficient for blood aspiration through the catheter 260. In other instances, the catheter 260 can be advanced relative to the PIV 280 such that at least the distal tip of the catheter 260 extends through the valve V, thereby placing the catheter 260 in fluid communication with a flow of blood, for example, from the branch B. As described above, the relocation of the catheter 260 relative to the PIV 280 can place the catheter 260 in fluid communication with a portion of the vein 40 receiving a flow of blood sufficient for aspiration through the catheter 260 while maintaining access to the vein 40 via the indwelling PIV 280.

Figure 5:
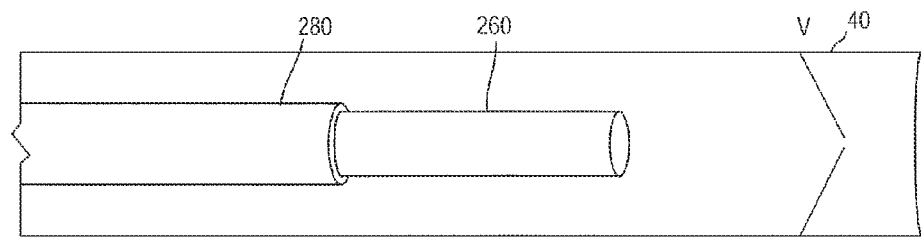

In some instances, the reduction in blood flow past the PIV 280 resulting from the at least partial occlusion of the vein 40 can be such that the success of aspirating a volume of blood is not dependent on the flow of blood from or through the branch B. For example, FIG. 5 illustrates the PIV 280 and the catheter 260 dwelling within a vein 40 having a diameter that is sufficiently large to allow blood to flow around the portion of the PIV 280 and/or catheter 260 dwelling in the vein 40. In some such instances, the vein 40 is not in fluid communication with a branch vessel that is between the catheter 260 and the valve V, yet a volumetric flow rate through that portion of the vein 40 is nonetheless sufficient for aspiration through the catheter 260. Moreover, in some such instances, because a sufficient volume of blood flows past the PIV 280, the location of the distal end of the catheter 260 relative to a distal end of the PIV 280 can be variable. That is to say, in such instances, the catheter 260 placement is not dependent on a position of a branch vessel and/or a valve V. In some instances, for example, the distal tip of the catheter 260 and the distal tip of the PIV 280 can be flush. In other instances, the catheter 260 can remain within a portion of the PIV 280 (e.g., the distal tip of the catheter 260 is proximal to the distal tip of the PIV 280, relative to the user).

Conversely, in other instances, the PIV 280 and the catheter 260 can be dwelling within a vein 40 having a relatively small diameter, as shown in FIG. 6. In such instances, the PIV 280 can substantially block or occlude the lumen of the vein 40 such that little or no flow of blood flows past the PIV 280. In such instances, a portion of the vein 40 may also lack a branch vessel and/or valve. As such, a negative pressure exerted through the catheter 260 for aspiration, in some instances, can be sufficient to collapse a portion of the vein 40. For example, the negative pressure exerted through the catheter 260 can result in at least a portion of the vein wall collapsing, which in turn, can at least partially occlude an opening of the catheter 260, as illustrated by the arrow AA in FIG. 7. In some instances, modulating a pressure and/or a rate of pressure change can limit and/or reduce a likelihood of vein collapse. Similarly, the catheter 260 and/or any suitable portion of a fluid transfer device coupled to the catheter 260 can be configured to limit, modulate, cap, and/or control a negative pressure exerted therethrough and/or can have a diameter or design configured to limit a volumetric flow rate therethrough, which in turn, can limit and/or reduce a likelihood of vein collapse.

In some instances, the catheter 260 can be moved relative to the PIV 280, for example, to place the distal end of the catheter 260 in a position within the vein 40 having a larger diameter and/or that is otherwise able to resist collapse. For example, the position within the vein 40 can be proximal to a branch vessel or valve. In other instances, the catheter 260 can be removed from the PIV 280 and can be replaced with, for example, a catheter having a smaller gauge or the like, which in turn, can result in a decrease in negative pressure associated with aspiration. In some instances, after a vein collapse (e.g., as shown in FIG. 7), the catheter 260 can be advanced within the vein 40 to move the catheter 260 through the collapsed portion, thereby disposing the opening of the catheter 260 in a non-collapsed portion of the vein 40. As described above, the relocation and/or replacement of the catheter 260 relative to the PIV 280 can allow for aspiration through the catheter 260 while maintaining access to the vein 40 via the indwelling PIV 280.

In some instances, any suitable fluid transfer device can be used to insert a catheter though an indwelling PIV to draw a volume of blood from a patient. For example, FIGS. 8-11 illustrate a fluid transfer device 300 used for phlebotomy through a peripheral intravenous line. The fluid transfer device 300 includes an introducer 310, a catheter 360, an actuator 370, and an adapter 375. The fluid transfer device 300 can be any suitable shape, size, or configuration and is configured to be coupled to, for example, a peripheral intravenous line (NV). In some embodiments, the fluid transfer device 300 can be similar to and/or substantially the same as any of those described in U.S. Patent Publication No. 2014/0364766 entitled, "Systems and Methods for Phlebotomy Through a Peripheral IV Catheter," filed Aug. 26, 2014 (referred to henceforth as the "'766 publication"), the disclosure of which is incorporated herein by reference in its entirety. As such, portions of the fluid transfer device 300 (also referred to herein as "transfer device" or "device") are not described in further detail herein.

As described above, the transfer device 300 includes the introducer 310, the catheter 360, the actuator 370, and the adapter 375. The adapter 375 can be any suitable adapter such as, for example, a Y-adapter or a T-adapter. For example, in this embodiment, the adapter 375 is a T-adapter including a first port coupled to the introducer 310, a second port coupled to a cannula (see e.g., FIG. 8), and a third port that can be coupled to the PIV (not shown). In some embodiments, the ports can be and/or can include a Luer Lok™ or the like that can fluidically seal the ports when the adapter 375 is not coupled to a device (e.g., the transfer device 300, a PIV, etc.).

The introducer 310 of the transfer device 300 includes a first member 311 and a second member 313. The introducer 310 can be any suitable shape, size, or configuration. For example, in some embodiments, the introducer 310 can be disposed in and/or can have a substantially telescopic arrangement (as shown in FIGS. 9-11). In some embodiments, the introducer 310 can have a shape that is, for example, similar to a syringe or the like. The first member 311 includes a proximal end portion and a distal end portion. The proximal end portion of the first member 311 is configured to be engaged by a user during operation (e.g., the proximal end portion includes a flange or the like). The distal end portion of the first member 311 includes and/or is otherwise coupled to a lock 350. For example, the lock 350 can be a Luer Lok™ or the like configured to couple the introducer 310 to the adapter 375 and/or an indwelling PIV (not shown in FIGS. 8-11). Moreover, the lock 350 includes a seal member 320 that defines and/or forms a substantially fluid tight seal with, for example, the first member 311. In addition, the seal member 320 receives a portion of the second member 313 and/or the catheter 360 as the second member 313 and/or the catheter 360 is advanced beyond the seal member 320 in the distal direction and maintains a substantially fluid tight seal around the portion of the second member 313 and/or the catheter 360, thereby substantially preventing a backflow of fluid into the introducer 310. The seal member 320 can be any suitable configuration such as, for example, an O-ring, a one-way valve, a diaphragm, a self-healing diaphragm, a check valve, or any other suitable seal member.

The first member 311 slidably receives at least a portion of the second member 313 and/or the actuator 370. The first member 311 defines a channel 312 that is configured to define a range of motion for the second member 313 relative to the first member 311. The channel 312 extends along a length of the first member 311 between the proximal end portion 3151 and the distal end portion 3152, as shown in FIGS. 9-11. More particularly, the channel 312 does not extend through the proximal end portion and/or the distal end portion of the first member 311 (i.e., the channel 312 does not extend the entire length of the first member 311). Thus, at least a distal end portion the channel 312 is bounded by an inner surface of the first member 311. The channel 312 can have any suitable shape and/or size. For example, in some embodiments, the channel 312 has a first cross-sectional area at or near the proximal end portion of the first member 311 and a second cross-sectional area at or near a distal end portion of the first member 311. In some embodiments, the channel 312 can be configured to fan-out, flare, and/or otherwise widen along a length of the first member 311 in the distal direction. As described in further detail herein, a portion of the second member 313 can be movably disposed in the channel 312, which in turn, defines, for example, a range of motion associated with the second member 313 relative to the first member 311.

The second member 313 of the introducer 310 includes a proximal end portion and a distal end portion. The distal end portion of the second member 313 has a protrusion 314 extending from an outer surface that is movably disposed within the channel 312 of the first member 311. The distal end portion of the second member 313 includes and/or is coupled to a guide member 330 that receives at least a portion of the catheter 360. The guide member 330 is configured to support and/or otherwise guide at least the portion of the catheter 360 as the catheter 360 is advanced through the introducer 310. For example, in some embodiments, the guide member 330 can be formed from a metal or hard plastic (e.g., with a higher durometer that the catheter 360), which can allow the guide member 330 to advance through the introducer 310, a PIV (not shown), and/or any obstruction or kink included therein. Moreover, the second member 313 can include a seal member 315 disposed in a distal position within an inner volume of the second member 313 and about a portion of the guide member 330. The seal member 315 forms a substantially fluid tight and/or substantially hermetic seal about the guide member 330. In some embodiments, the seal member 315 can be formed from an absorbent material such as POREX® or the like.

The arrangement of the introducer 310 is such that when the second member 313 is moved relative to the first member 311, the protrusion 314 is moved within the channel 312. As such, the channel 312 (and/or the portion of the inner surface defining the channel 312) defines a range of motion for the second member 313 relative to the first member 311. For example, with the channel 312 extending along the length of the first member 311, the range of motion associated with the second member 313 as defined by the channel 312 includes an axial motion (e.g., a distal and/or proximal direction) of the second member 313 within the first member 311 between its proximal position and its distal position. Similarly, the increased width associated with the second cross-sectional area can define, for example, a rotational range of motion about a longitudinal centerline of the first member 311, thereby allowing the second member 313 to at least partially rotate within and/or relative to the first member 311 (as described in detail in the '766 publication).

As shown in FIGS. 8-11, the actuator 370 of the transfer device 300 includes a proximal end portion and a distal end portion. In some instances, a user can engage the proximal end portion to manipulate at least the actuator 370 of the transfer device 300 to transition the transfer device 300 between, for example, a first configuration (FIGS. 8 and 9), a second configuration (FIG. 10), and a third configuration (FIG. 11). The proximal end portion is coupled to a secondary catheter 378 that includes a coupler 379, which in turn, can be coupled to a fluid reservoir (e.g., an evacuated container, sample reservoir, syringe, etc.). As described in further detail herein, the actuator 370 couples to the catheter 360 and places a lumen of the catheter 360 in fluid communication with a lumen of the secondary catheter 378. Thus, when the coupler 379 is coupled to the fluid reservoir, the catheter 360 is placed in fluid communication with the fluid reservoir.

The actuator 370 can have any suitable shape, size, or configuration. At least a portion of the actuator 370 can be inserted into the second member 313 and can be moved between, for example, a proximal position and a distal position (e.g., in a telescopic motion). In some embodiments, the actuator 370 can define a slot or the like configured to receive a portion of the second member 313. In such embodiments, a length of the slot can define a range of motion of the actuator 370 relative to the second member 313.

The catheter 360 of the transfer device 300 can be any suitable shape, size, or configuration. For example, in some embodiments, the catheter 360 can be about a 20-gauge catheter or the like. In other embodiments, the catheter 360 can be greater than or less than a 20-gauge catheter. Moreover, the catheter 360 can be formed of any suitable biocompatible material having any suitable stiffness and/or Shore durometer such that the catheter 360 has a desired flexibility, which in turn, can allow the catheter 360 to elastically deform without, for example, kinking or the like.

The catheter 360 has a proximal end portion and a distal end portion. The proximal end portion of the catheter 360 is coupled to the actuator 370 such that the lumen defined by the catheter 360 is in fluid communication with the secondary catheter 378. The distal end portion of the catheter 360 can be arranged in any suitable manner. For example, in some embodiments, the distal end portion of the catheter 360 can include a substantially open end-surface configured to place the lumen 3209 in fluid communication with, for example, a vein. In some embodiments, the distal end portion can include the open end-surface and any number of openings disposed on the side (e.g., circumference) of the catheter 360, as described in the '766 publication.

Figure 8:
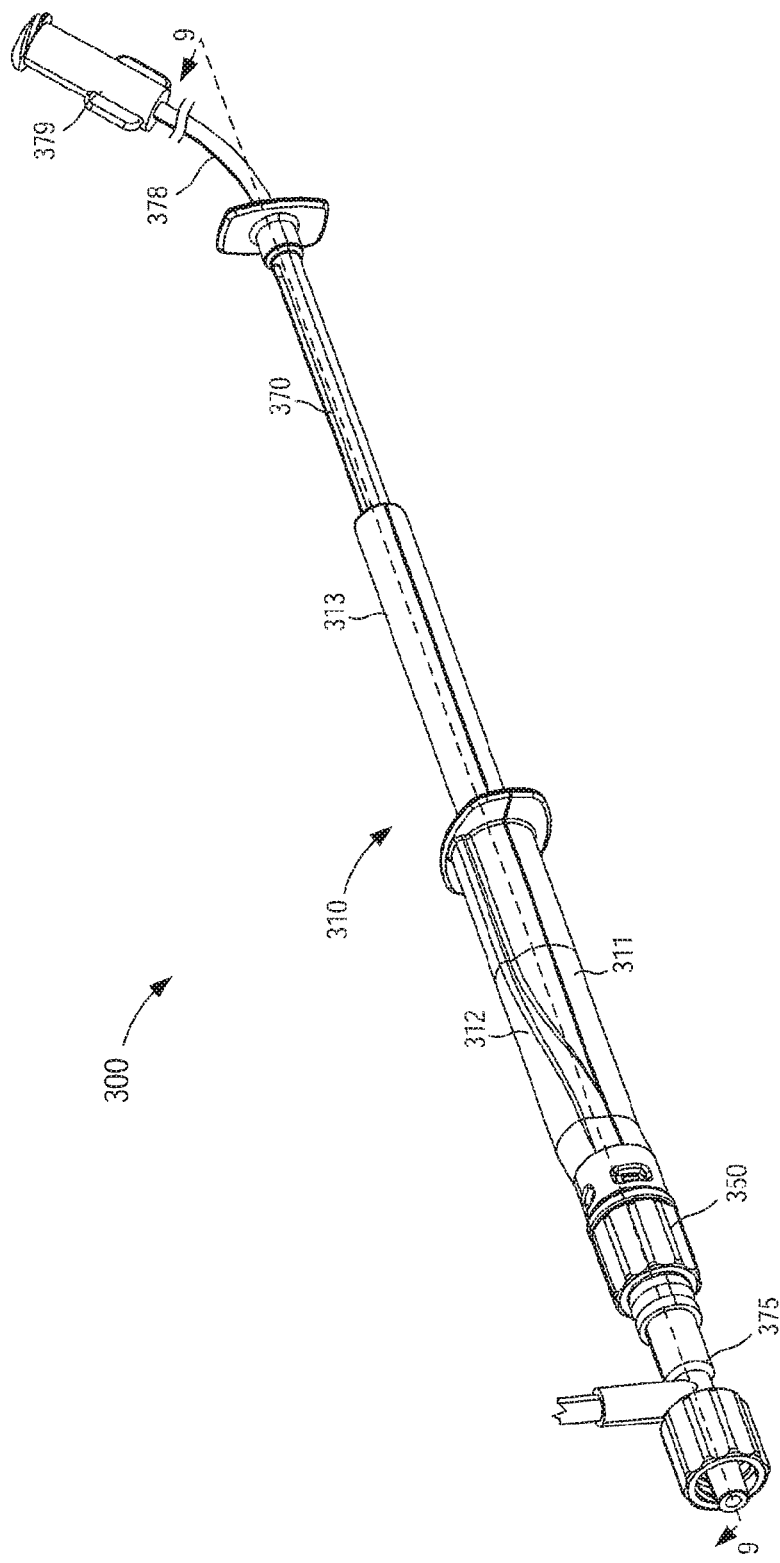
FIG. 8 is a perspective view of a fluid transfer device in a first configuration, according to an embodiment.

As shown in FIGS. 8 and 9, prior to use, the transfer device 300 can be disposed in a first configuration (e.g., an expanded configuration), in which the second member 313 is disposed in a proximal position relative to the first member 311 and the actuator 370 is disposed in a proximal position relative to the second member 313. In this manner, the guide member 330 is disposed within the first member 311 of the introducer 310 and at least the distal end portion of the catheter 360 is disposed within the guide member 330. Said another way, the catheter 360 is at least partially disposed in the introducer 310 when the transfer device 300 is in the first configuration. In some embodiments, the inner volume of the second member 313 and the inner volume of the first member can be substantially fluidically sealed such that the inner volumes are each substantially sterile. As a result, at least a portion of the catheter 360 is maintained in a substantially sterile environment prior to use.

While in the first configuration, a user (e.g., a phlebotomist) can manipulate the transfer device 300 to couple the first member 311 of the introducer 310 to the adapter 375. In other embodiments, the transfer device 300 can be pre-assembled with the adapter 375. In still other embodiments, the transfer device 300 can be used without the adapter 375. Although not shown in FIGS. 8-11, the third port of the adapter 375 can be coupled to a PIV. As a result, the introducer 310 is coupled (e.g., indirectly via the adapter 375 or directly when used without the adapter 375) to the PIV. Likewise, although not shown in FIGS. 8-11, the coupler 379 disposed at the end of the secondary catheter 378 can be coupled to a fluid reservoir or the like to place the lumen of the catheter 360 in fluid communication with the fluid reservoir.

Once coupled to the PIV and the fluid reservoir, the user can manipulate the transfer device 300 by engaging the first member 311 and the actuator 370 and exerting a force on the actuator 370. The force exerted on the actuator 370 moves the actuator 370 and the second member 313 in the distal direction relative to the first member 311, thereby placing the transfer device 300 in the second configuration, as indicated by the arrow BB in FIG. 10. More specifically, the actuator 370 moves the second member 313 from a proximal position to a distal position relative to the first member 311, while the actuator 370 remains in a relatively fixed position (e.g., its proximal position) relative to the second member 313. For example, in some embodiments, the arrangement of the first member 311, the second member 313, and/or the actuator 370 can be such that a relative movement thereby is controlled in a desired manner. Specifically, the second member 313 can be maintained substantially in the proximal position relative to the first member 311 until the force is applied (e.g., either directly or indirectly) to the second member 313 that is sufficient to move the second member 313 relative to the first member 311. In a similar manner, the actuator 370 can be maintained substantially in the proximal position relative to the second member 313 until a force is applied on the actuator 370 that is sufficient to move the actuator 370 relative to the second member 313.

As shown in FIG. 10, the actuator 370 and the second member 313 are collectively moved relative to the first member 311 in response to the applied force on the actuator 370. As such, a portion of the force moves the second member 313 within the first member 311 (e.g., the protrusion 314 within the channel 312), while the actuator 370 is retained in a substantially fixed position relative to the second member 313. Thus, a force sufficient to move the second member 313 relative to the first member 311 is less than a force sufficient to move the actuator 370 relative to the second member 313. Such an arrangement can, for example, ensure that the second member 313 is relative to the first member 311 prior to the actuator 370 being moved relative to the second member 313.

As shown in FIG. 10, the movement of the second member 313 to the distal position relative to the first member 311 advances the guide member 330 (coupled thereto) in the BB direction to a position in which at least the distal end portion of the guide member 330 is disposed in and extends past an end of the PIV. More specifically, as the second member 313 is moved to its distal position, the guide member 330 is concurrently advanced through a port or "basket" of the PIV (not shown). As described above, the guide member 330 is configured to have a stiffness and/or is formed from a material(s) with a hardness or durometer that is sufficient to pass through the port of the PIV substantially without kinking, breaking, bending, plastically deforming (e.g., permanently deforming), etc. Moreover, the guide member 330 can have a length and hardness that is sufficient to pass through any suitable PIV to dispose at least the distal end portion in a distal position relative to the end of the PIV. In some instances, the guide member 330 can be arranged such that when the second member 313 is in its distal position relative to the first member 311, the distal end portion of the guide member 330 is disposed in a vascular structure and at least partially outside of the PIV. Furthermore, with the actuator 370 maintained in a relatively fixed position relative to the second member 313, the distal end portion of the catheter 360 is maintained within the guide member 330, as shown in FIG. 10.

Once the second member 313 in its distal position, the applied force exerted on the actuator 370 can move the actuator 370 from its proximal position to its distal position relative to the second member 313. For example, the portion of the applied force that was operable in moving the second member 313 relative to the first member 311 is instead operable in moving the actuator 370 from its proximal position to its distal position relative to the second member 313, as indicated by the arrow CC in FIG. 11. The movement of the actuator 370 to its distal position advances the catheter 360 in the CC direction to a position in which at least the distal end portion of the catheter 360 is disposed in and extends past the PIV (e.g., a second position and/or a desired or predetermined position). The catheter 360 can be advanced such that the distal end portion of the catheter 360 extends beyond the distal end portion of the guide member 330 to be disposed in the vascular structure and at least partially outside of the PIV and the guide member 330 (e.g., at a predetermined position). With the catheter 360 advanced, for example, to the second position (e.g., the predetermined position), the lumen of the catheter 360 can receive a flow of bodily fluid, which can flow therethrough and into the fluid reservoir. For example, in some embodiments, the fluid reservoir can be an evacuated reservoir such as a Vacutainer® tube, which can exert a suction force through the lumen of the catheter 360. Thus, the bodily fluid (e.g., blood) is drawn through the lumen of the catheter 360 and the lumen of the secondary catheter 378 and into the fluid reservoir. In this manner, a phlebotomist can collect (e.g., draw) a given amount of blood through an existing peripheral intravenous line without the need for additional needle sticks.

As described herein, in some embodiments, the predetermined distance can be based on, for example, one or more characteristics associated the vasculature anatomy of the patient. In some instances, for example, the PIV can be a Jelco® 1.0 in, 20-gauge catheter and the catheter 360 can be advanced to a position such that a distance between the distal tip of the catheter 360 and the distal tip of the PIV is between about 0.0 mm and about 50.0 mm. In the embodiment shown in FIGS. 8-11, for example, the predetermined distance can be about 15.0 mm beyond the distal end of the PIV when the catheter 360 is in the second position. As described above with reference to FIGS. 3-7, in some instances, the successful aspiration of a volume of blood from the vein through the catheter 360 can be based at least in part on one or more characteristics associated with the vascular anatomy. For example, in some instances, disposing the distal end of the catheter 360 at about 15.0 mm from the distal end portion of the PIV can, in some instances, place the distal end of the catheter 360 in position within the vein receiving a desired volumetric flow of blood (e.g., a branch is disposed between the catheter 360 and a valve and/or any other suitable venous arrangement).

In some instances, however, the second position of the catheter 360 may be such that the distal end of the catheter 360 is disposed in a portion of the vein having a flow of blood insufficient for aspiration. As such, the user can engage the actuator 370 to move the catheter 360 in the distal direction or the proximal direction to place the distal end of the catheter 360 in a portion of the vein having a flow of blood sufficient for aspiration through the catheter 360. In other words, the predetermined distance can be any suitable distance within, for example, a predetermined range of distances (e.g., between about 0.0 mm and about 50.0 mm).

Once a desired volume of blood is transferred to, for example, a fluid reservoir such as an evacuated fluid reservoir or tube (e.g., coupled to the coupler 379), the user can retract the actuator 370, which in turn moves the catheter 360 in a proximal direction from the second position toward the first position. The user can then decouple the device 300 from the adapter 375 and/or the PIV and decouple the fluid reservoir from the coupler 379. In some instances, the device 300 can then be safely discarded.

In some instances, it may be desirable to rotate the catheter 360 relative to the first member 311, thereby rotating the distal end portion within the vascular structure (e.g., to prevent a suctioning of the distal end portion to a wall of the vascular structure). In such instances, the user can, for example, rotate the actuator 370 and the second member 313 relative to the first member 311. More specifically, manipulation of the actuator 370 by the user can result in a rotation of both the actuator 370 and the second member 313 relative to the first member 311. As described above, the channel 312 can have a cross-sectional shape and/or area at or near the proximal end portion of the first member 311 that is associated with and/or slightly larger than a size of the protrusion 314, thereby defining the rotational range of motion of the second member 313 when disposed in the proximal position (e.g., about 30 degrees, about 60 degrees, about 90 degrees, about 120 degrees, about 180 degrees, about 210 degrees, or more). In some instances, such rotation of the actuator 370 and the second member 313 can, for example, reduce a likelihood of the distal end portion of the catheter 360 forming suction against a wall of the vascular structure (e.g., a vein). In some instances, it may be desirable to rotate the second member 313 as the actuator 370 is being moved toward its distal position, as described in the '799 publication.

Figure 12:
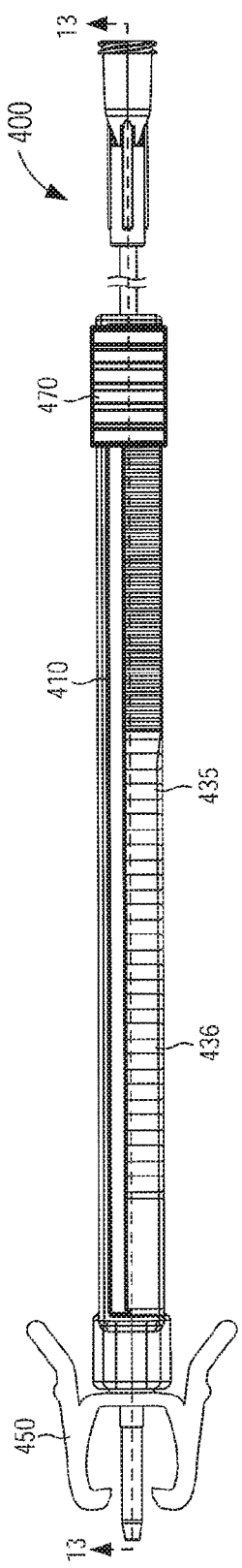
FIG. 12 is a top view of a fluid transfer device in a first configuration, according to an embodiment.
Figure 13:
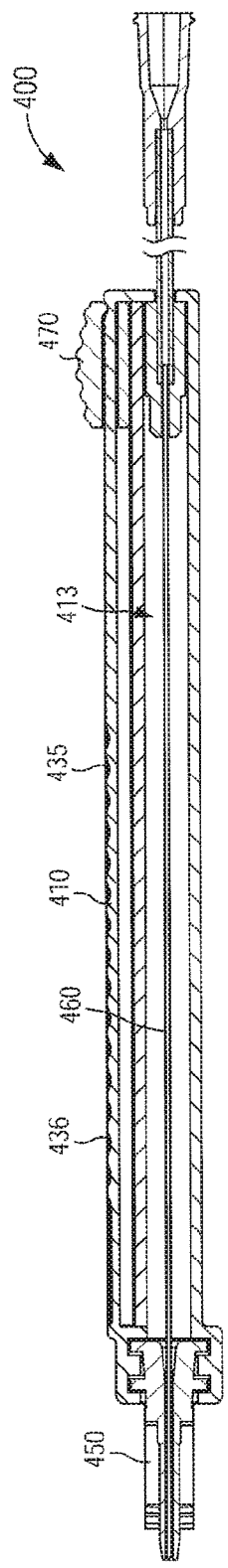
FIGS. 13 and 14 are cross-sectional views of the fluid transfer device of FIG. 12 taken along the line 13-13, in the first configuration and a second configuration, respectively.
Figure 14:
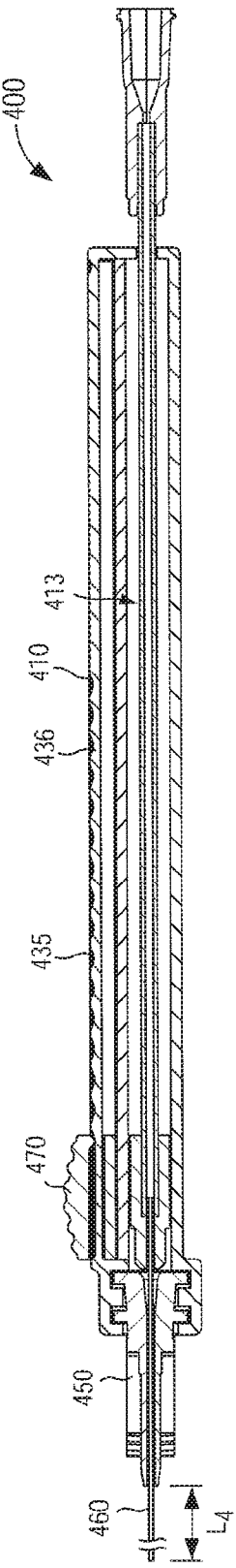

While the fluid transfer device 300 is particularly shown and described above with reference to FIGS. 8-11, in other embodiments, any suitable fluid transfer device can be used to access a vein via a PIV and to place a catheter in a desired position within the vein or within the PIV to aspirate a volume of blood from the patient. For example, FIGS. 12-14 illustrate a fluid transfer device 400 for phlebotomy through a peripheral intravenous line or catheter in a first configuration and second configuration, respectively, according to an embodiment. The fluid transfer device 400 (also referred to herein as "transfer device") is configured to couple to and/or otherwise engage an indwelling peripheral intravenous catheter (PIV) to transfer fluid from (e.g., aspiration of blood) and/or transfer fluid to (e.g., infusion of a drug or substance) a vein of a patient, as described in further detail herein. The transfer device 400 can be any suitable shape, size, and/or configuration. For example, as shown in FIGS. 12-14, the transfer device 400 includes at least an introducer 410, a catheter 460 (or cannula), and an actuator 470. In some embodiments, the transfer device 400 can be similar to and/or substantially the same as any of those described in U.S. patent application Ser. No. 15/014,834 entitled, "Devices and Methods for Fluid Transfer Through a Placed Peripheral Intravenous Catheter," filed Feb. 3, 2016 (referred to henceforth as the "'834 application"), the disclosure of which is incorporated herein by reference in its entirety. As such, some aspects of the transfer device 400 are not described in detail herein and should be considered substantially similar to such aspects of the transfer devices described in the '834 application unless explicitly expressed otherwise.

The introducer 410 of the transfer device 400 can be any suitable configuration. For example, in some embodiments, the introducer 410 can be an elongate member having a substantially circular cross-sectional shape. The introducer 410 has an outer surface 435 and defines an inner volume 413 within which at least a portion of the catheter 460 and at least a portion of the actuator 470 are movably disposed. Although not shown in FIGS. 12-14, a proximal end portion of the introducer 410 can include an opening or port configured to movably receive a portion of the catheter 460. As such, a first portion of the catheter 460 can be disposed within the inner volume 413 and a second portion of the catheter 460 can be disposed outside of the inner volume 413. A distal end portion of the introducer 410 includes and/or is coupled to a lock 450 configured to physically and fluidically couple the introducer 410 to the PIV, as described in further detail herein.

As shown in FIGS. 12-14, the outer surface 435 of the introducer 410 includes a set of ribs 436 distributed along at least a portion of the introducer 410. More particularly, each rib 436 extends widthwise along at least a portion of the introducer 410 with each rib 436 successively distributed lengthwise along at least the portion of the introducer 410. In this manner, the outer surface 435 defines alternating local minima and local maxima arranged along the portion of the length of the introducer 410, as described in detail in the '834 application. The arrangement of the transfer device 400 is such that a portion of the actuator 470 is configured to be advanced along the outer surface 435 forming the set of ribs 436 as a user moves the actuator 470 relative to the introducer 410, which in turn, vibrates the actuator 470 (and the catheter 460 coupled thereto). In some instances, this vibration can, for example, facilitate the advancing of the catheter 460 through a portion or the transfer device 400, a portion of the PIV, and/or a portion of the vasculature. Moreover, in some instances, the vibration can provide a user with a haptic, tactile, and/or audible indicator associated with a position of the catheter 460 relative to the introducer 410 and/or PIV, as described in detail in further detail herein.

As described above, the inner volume 413 is configured to receive a portion of the catheter 460 and a portion of the actuator 470, as shown in FIGS. 13 and 14. In some embodiments, an inner surface of the introducer 410 that defines the inner volume 413 can have, for example, a tortuous cross-sectional shape (not shown in FIGS. 12-14) such that an axis defined by a first portion of the inner volume 413 is parallel to and offset from an axis defined by a second portion of the inner volume 413. In such embodiments, the first portion of the inner volume 413 can be spaced apart from the second portion of the inner volume 413 without being fluidically isolated therefrom. In some embodiments, the introducer 410 can define a slot, channel, track, opening, and/or the like that is in fluid communication with the inner volume 413. In some embodiments, the tortuous cross-sectional shape of the inner volume 413 is such that the second portion cannot be viewed (e.g., is out of the line of sight) via the slot or the like in fluid communication with the first portion of the inner volume 413, which in turn, can limit and/or substantially prevent contamination of at least the catheter 460 disposed therein, as described in detail in the '834 application.

As described above, the lock 450 of the transfer device 400 is included in and/or coupled to the distal end portion of the introducer 410. The lock 450 can be any suitable shape, size, or configuration. In some embodiments, the lock 450 is substantially similar to those described in detail in the '834 application. As such, the lock 450 can selectively engage and/or contact the PIV to couple the introducer 410 thereto. In some embodiments, the shape, size, and/or arrangement of the lock 450 is such that the lock 450 forms three points of contact with the PIV 405. In some embodiments, such an arrangement can provide structural rigidity and/or support to the PIV as a portion of the lock 450 (e.g., a proboscis or the like) is inserted into a portion of the PIV as well as, structural rigidity and/or support to the catheter 460 as the catheter 460 is moved therethrough.

The catheter 460 of the transfer device 400 is movably disposed within the inner volume 413 defined by the introducer 410 (e.g., the second portion of the inner volume 413) and is coupled to the actuator 470. In some embodiments, the catheter 460 can be moved (e.g., via movement of the actuator 470) between a first position and a second position to transition the transfer device 400 between the first configuration and the second configuration, respectively. More specifically, at least a portion of the catheter 460 is disposed within the inner volume 413 and/or the lock 450 when the catheter 460 is in the first position (FIG. 13) and at least a portion of the catheter 460 extends beyond the introducer 410 and lock 450 to place a distal end of the catheter 460 in a position within the PIV or a position distal to the PIV when the catheter 460 is in the second position (FIG. 14), as described in further detail herein. As shown in FIGS. 12-14, a proximal end portion of the catheter 460 and/or a secondary catheter coupled to the actuator 470 and in fluid communication with the catheter 460 is configured to extend through the opening and/or port defined by the proximal end portion of the introducer 410. In this manner, a proximal end portion of the catheter 460 and/or the secondary catheter can be coupled to a fluid reservoir, fluid source, syringe, and/or the like, which in turn, places the catheter 460 in fluid communication therewith.

The catheter 460 can be any suitable shape, size, and/or configuration. In some embodiments, the catheter 460 can be substantially similar to the catheters described in detail in the '834 application. In some embodiments, at least a portion of the catheter 460 can have an outer diameter (e.g., between a 16-gauge and a 26-gauge) that is substantially similar to or slightly smaller than an inner diameter defined by a portion of the lock 450. In this manner, an inner surface of the portion of the lock 450 can guide the catheter 460 as the catheter 460 is moved between the first position and the second position. In some embodiments, such an arrangement can limit and/or can substantially prevent bending, deforming, and/or kinking of the catheter 460 as the catheter 460 is moved between the first position and the second position. In some embodiments, the catheter 460 can have a length that is sufficient to place a distal surface of the catheter 460 in a desired position relative to a distal surface of the PIV when the catheter 460 is in the second position, as described in further detail herein.

The actuator 470 of the transfer device 400 can be any suitable shape, size, and/or configuration. In some embodiments, the actuator 470 can be substantially similar to the actuators described in detail in the '834 application. For example, the actuator 470 can include a first portion movably disposed within the inner volume 413 and a second portion movably disposed outside of the inner volume 413 and in contact with the outer surface 435 of the introducer 410. In this manner, a user can engage the second portion of the actuator 470 and can move the actuator 470 relative to the introducer 410 to move the catheter 460 coupled to the first portion of the actuator 470 between the first position and the second position. With the second portion of the actuator 470 in contact with the outer surface 435, the actuator 470 can be moved along the set of ribs 436 when the actuator 470 is moved relative to the introducer 410, which in turn, produces a haptic, tactile, and/or audible output or feedback. In some instances, the haptic, tactile, and/or audible output and/or feedback can provide an indication to the user that is associated with a position of the distal end of the catheter 460 relative to, for example, a distal end of the PIV and/or the introducer. Although not show in FIGS. 12-14, in some embodiments, the introducer 410 and/or the actuator 470 can include indicia or the like configured to provide to the user a visual indication associated with the position of the distal end of the catheter 460. For example, in some embodiments, the introducer 410 can include a gradation or the like that can indicate a distance between, for example, a distal end of the catheter 460 and a distal tip of the PIV.

In some embodiments, the transfer device 400 can be disposed in the first configuration prior to use (e.g., shipped, stored, prepared, etc. in the first configuration). In use, a user can manipulate the transfer device 400 to couple the lock 450 to an indwelling PIV. For example, the PIV can be percutaneously inserted into any suitable vein of the forearm 10 or hand 30 described above with reference to FIG. 1. As described above, the size and/or configuration of the PIV can be based at least in part on the vein in which the PIV is inserted. For example, in some instances, a portion of the PIV can be disposed within a vein of the forearm 10 (e.g., the basilic vein 11 or the like) that is sufficiently large to receive a 20-gauge PIV. Similarly, the size and/or configuration of the transfer device 400 can be based at least in part on the size of the PIV. For example, in embodiments in which the indwelling PIV is and/or has a 20-gauge catheter, the catheter 460 of the transfer device 400 can be between, for example, 22-gauge and 26-gauge.

With the lock 450 coupled to the indwelling PIV, the user can engage the actuator 470 to move the actuator 470 relative to the introducer 410, which in turn, moves the catheter 460 from the first position (e.g., disposed within the introducer 410 and/or the lock 450) toward the second position. In some embodiments, the arrangement of the actuator 470 and the introducer 410 is such that advancing the actuator 470 relative to the introducer 410 produces a haptic output and/or feedback configured to provide and indicator to the user that is associated with position of the distal end of the catheter 460 relative to the introducer 410 and/or the PIV. For example, based on the haptic feedback or the any other suitable indicator, the user can place the catheter 460 in the second position such that the distal surface of the catheter 460 extends a desired distance beyond the distal surface of the PIV.

With the catheter 460 in the second position (e.g., with the transfer device 400 in the second configuration shown in FIG. 14), the user can establish fluid communication between a fluid reservoir, fluid source, syringe, and/or the like and the catheter 460. For example, in some embodiments, the user can couple the catheter 460 (or a secondary catheter not shown) to the fluid reservoir, fluid source, syringe, and/or the like. With the catheter 460 in fluid communication with the fluid reservoir and/or fluid source, the transfer device 400 can then transfer a fluid from the patient or transfer a fluid to the patient via the catheter 460 extending through and beyond the PIV.

As shown in FIG. 14, in some instances, the catheter 460 can be in the second position when the actuator 470 is in a distal most position. In this manner, the distal surface of the catheter 460 is positioned within the vein at a predetermined distance beyond the distal surface of the catheter 460. In some embodiments, the length of the catheter 460 can be sufficient to define a predetermined and/or desired distance or length $L_4$ between the distal surface of the catheter 460 and the distal surface of the PIV when the catheter 460 is in the second position. In some instances, placing the distal surface of the catheter 460 the predetermined and/or desired distance or length $L_4$ from the distal surface of the PIV can, for example, place the distal surface of the catheter 460 in a desired position within the vein. For example, in some instances, placing the distal surface of the catheter 460 at the predetermined and/or desired distance length $L_4$ from the distal surface of the PIV can, for example, place the distal surface of the catheter 460 in a position within a vein that is substantially free from debris (e.g., fibrin/blood clots) otherwise surrounding the distal end portion of the PIV.

In some instances, the indwelling PIV can substantially occlude at least a portion of the vein within which the PIV is disposed (e.g., either the PIV itself and/or debris forming around the PIV). As such, PIVs are often suited for delivering a fluid rather than aspirating blood. The venous system, however, is a capacitance system and thus, reroutes blood flow through a different vein (e.g., forms a bypass around the occlusion or substantial occlusion). Moreover, the alternate venous structures (i.e., branches) typically rejoin the vein in which the PIV is disposed at a given distance downstream of the PIV and thus, deliver at least portion of the flow of blood that would otherwise be flowing through the vein in which the PIV is disposed.

Thus, in some embodiments, the length of the catheter 460 and/or transfer device 400 when in the position and/or second configuration can be based at least in part on characteristics associated with the vascular structure (e.g., vein) within which the PIV and catheter 460 are disposed. For example, in some instances, the distal surface of the catheter 460 is placed within a compartment and/or portion of the vein that receives a flow of blood sufficient to aspirate a volume of the blood through the catheter 460. In some instances, the compartment and/or portion of the vein can be based on an existence of one or more valves and/or branch vessels in fluid communication vein and/or a position of the one or more valves and/or branch vessels relative to the distal surface of the PIV and/or the distal surface of the catheter 460.

In some instances, for example, the predetermined and/or desired distance can be between about 0.0 millimeters (e.g., the distal surfaces are flush) and about 100 millimeters (mm). In other embodiments, the predetermined and/or desired distance can be between about 10 mm and about 90 mm, between about 20 mm and about 80 mm, between about 30 mm and about 70 mm, between about 30 mm and about 60 mm, between about 40 mm and about 50 mm, or between any other suitable range and subranges therebetween. In some embodiments, for example, the transfer device 400 can be configured such that the actuator 470 can move about 95 mm along the introducer 410 (e.g., the transfer device 400 has a 95 mm stroke) to position the distal surface of the catheter 460 at about 40 mm beyond the distal surface of the PIV to which the transfer device 400 is coupled. In other embodiments, for example, the transfer device 400 can have a 47 mm stroke that positions the distal surface of the catheter 460 at about 20 mm beyond the distal surface of the PIV to which the transfer device 400 is coupled. In still other embodiments, the transfer device 400 can have any suitable stroke length to position the distal surface of the catheter 460 at the predetermined and/or desired distance from the distal surface of the PIV. As described in further detail herein, the stroke length and thus, the predetermined and/or desired distance and/or length $L_4$ can be based at least in part on the arrangement of the vascular structure in which PIV and catheter 460 are disposed.

Vascular Structure Analysis

As described above with reference to FIGS. 1-5, a portion of a PIV dwelling within a vein obstructs, at least partially, a lumen defined by the vein and thus, restricts a flow of blood therethrough. In addition, an amount of debris such as blood clots/thrombus or fibrin tails, etc. formed around the portion of the PIV often increases with PIV dwelling time, thereby further limiting blood flow through at least a portion of the vein. In some instances, the blood flow through the vein can be restricted to an extent that renders aspiration of blood through the PIV and/or through a catheter disposed at or near a distal end of the PIV unsuccessful or at least impractical. In addition, the obstructions within the vein and/or the restrictions of the flow can increase a turbulence of the blood flow, which in turn, can increase the likelihood of hemolysis (i.e., the shearing of red blood cells). Similarly, the application of more negative pressure through a blood draw catheter to overcome the restrictions in flow can increase a stress on or in the red blood cells that can result in hemolysis. As described herein, however, it is contemplated that vascular structures such as valves and/or branches disposed in the vein and/or in fluid communication with the vein can, for example, sufficiently mitigate the effects of the indwelling PIV, thereby allowing aspiration of blood through a catheter that gains access to the vein via the indwelling PIV as well as reducing a likelihood of hemolyzed blood samples.

As described above with reference to the devices 200 and/or 300, in some instances, advancing a blood draw catheter through an indwelling PIV such that a distal end of the catheter is disposed within, for example, a predetermined range of distances from a distal end of the PIV can place the catheter in a position relative to the vein that receives a volumetric flow of blood sufficient for blood aspiration. For example, the device 200 is configured to couple to the PIV 280 (e.g., dwelling within a vein) and to advance the catheter 260 to, for example, a distal most position (e.g., the second position) such that the distal end of the catheter 260 is disposed approximately 15.0 mm from the distal end of the PIV 280. In some instances, advancing the catheter 260 relative to the PIV 280 (e.g., by placing the catheter 260 in the second position), an average success rate (or a predicted average success rate) associated with blood aspiration through the catheter 260 increased.

In general, it is contemplated and further described herein that the increased success rate associated with blood aspiration through the catheter 260 when the catheter 260 is disposed, for example, in the second position is indicative of one or more relationships between the venous anatomy and a position of a blood draw catheter relative to the venous anatomy and/or an indwelling PIV. Accordingly, a prospective single-center study of the lower arm venous anatomy including the antecubital, forearm, and hand/wrist region was conducted. The venous anatomy of thirty-five (35) healthy adults was imaged using ultrasonic imaging and data on location and frequency of valves, the valves locations and frequency of branches or collateral vessels, and vessel diameters was recorded in areas where intravenous (IV) catheter placement is common. The first 5 subjects served as validation of study methods and ultrasound technique consistency. Data for the subsequent 30 subjects was collected and analyzed.

A nurse marked hypothetical IV insertion locations (e.g., locations that would likely be used to access a vein for aspiration) in each subject's hand/wrist, forearm, and antecubital regions, on each arm—six (6) total sites marked per subject. The nurse and/or a medical technician took 1-2 photographs of each subject's arms to document where the hypothetical IV insertion site marks were placed.

A separate ultrasound technician performed an ultrasonic imaging study capturing the information in a study worksheet. Two-hundred ten (210) vessels were imaged and the information was recorded, including:

Position of the IV mark site on anatomic diagram of arm, including distance from crease of the wrist (whether positive or negative).

Distances from each IV mark site to vein valves up to 8 centimeters (cm) centrally.

Distances from each IV mark site to vein branches or collateral vessels up to 8 cm centrally.

Vessel diameters at the IV mark site and immediately central to every vein branch or collateral vessel up to 8 cm centrally.

The data is set forth in Table 1, below:

at the hypothetical insertion site; the PIV having the length of 1.00 in (25.4 mm) would place the distal end of the PIV at about 1.00 in (25.4 mm) from the hypothetical insertion site; the PIV having the length of 1.16 in (29.46 mm) would place the distal end of the PIV at about 1.16 in (29.46 mm) from the hypothetical insertion site; and the PIV having the length of 1.25 in (31.75 mm) would place the distal end of the PIV at about 1.25 in (31.75 mm) from the hypothetical insertion site.

The use of a fluid transfer device such as, for example, the transfer devices 300 and/or 400 to aspirate a volume of blood through the indwelling PIV was considered. As described above, the length of the catheter (e.g., the catheter 360) can be based at least in part on the venous anatomy. For example, for the transfer device 300, the distal end of the catheter 360 can extend approximately 15 mm beyond a distal end of, for example, 1.16 in (29.46 mm) PIV, when the catheter 360 is in the distal most position (e.g., a second position). The transfer device 400 is configured such that the catheter 460 extends approximately 30.0 mm beyond a distal end of, for example, the 1.16 in (29.46 mm) PIV, when the catheter 460 is in the distal most position (e.g., a second position). That is to say, the distal surface of the catheter 360 is configured to extend approximately 40 mm beyond a hub of the PIV and/or beyond a hypothetical insertion point while the catheter 460 is configured to extend approximately 64.5 mm beyond the hub of the PIV and/or beyond the hypothetical insertion point. Therefore, when considering the transfer device 400, for example, the length of the distal surface of the catheter 460 from the distal tip of the PIV catheter (also referred to herein as "L") when the catheter 460 is in a distal most position and when the effective length of the PIV is 0.00 in (0.0 mm) is approximately 64.5 mm; the length L when the catheter 460 is in the distal most position and when the effective length of the PIV is 1.00 in (25.4 mm) is approximately 39.0 mm; the length L when the catheter 460 is in the distal most position and when the effective

TABLE 1

| Branch Distance and Diameter | | | | | | | |
|---|---|---|---|---|---|---|---|
| | PIV Length 0.00 in/0.00 mm | | PIV Length 1.00 in/25.4 mm | | PIV Length 1.16 in/29.46 mm | | PIV Length 1.25 in/31.75 mm |
| Length Past Tip | 64.5 | | 39 | | 35 | | 32.7 |
| Length Past Hub | 64.5 | | 64.4 | | 64.5 | | 64.5 |
| No Branches within 80.0 mm | 23 | 11% | 37 | 18% | 41 | 20% | 44 | 21% |
| Branch >= 64.5 mm | 11 | 5% | 23 | 11% | 25 | 12% | 28 | 13% |
| Branch <= 64.5 mm | 176 | 84% | 150 | 71% | 144 | 69% | 138 | 66% |
| Totals | 210 | 100% | 210 | 100% | 210 | 100% | 210 | 100% |
| Dist. <= 64.5 mm Diam. >= 1 mm | 148 | 70% | 134 | 64% | 131 | 62% | 128 | 61% |
| Dist. <= 64.5 mm Diam. < 1 mm | 28 | 13% | 16 | 8% | 13 | 6% | 10 | 5% |
| No/Unsuitable Branch | 62 | 30% | 76 | 36% | 79 | 38% | 82 | 39% |

Specifically, as shown in Table 1 and FIGS. 15-18, data associated with branch vessel characteristics relative to a hypothetical PIV having an effective length of 0.00 in (FIG. 15), an effective length of 1.00 in (FIG. 16), an effective length of 1.16 in (FIG. 17), and an effective length of 1.25 in (FIG. 18) was determined. For example, an ultrasound image of each vein was taken from the hypothetical IV insertion point to 8.0 cm (80 mm) centrally (e.g., in a proximal or downstream direction). Commonly used PIV lengths were considered, in which the PIV having the length of 0.00 in (0.00 mm) would place the distal end of the PIV length of the PIV is 1.16 in (29.46 mm) is approximately 35.0 mm; and the length L when the catheter 460 is in the distal most position and when the effective length of the PIV is 1.25 in (31.75 mm) is approximately 32.7 mm, as shown in Table 1.

An effect on blood flow and/or successful aspiration produced by branch vessels beyond 80.0 mm was not considered. For example, in some instances, a flow rate through the lumen of a catheter has an inverse relationship with the overall length of the catheter. In other words, a catheter having a given inner diameter and a first length can be associated with and/or otherwise produce a lower flow rate that is lower than a flow rate of a catheter having the same given diameter and a second length, less than the first length. Thus, in this example, a flow rate associated with a catheter length of 80.0 mm (8.0 cm or about 3.15 in) beyond the hypothetical insertion point was not considered suitable for use with, for example, a 20-gauge PIV and/or otherwise for use in this study. In other instances, however, a flow rate through a catheter having such a length or a greater length can be sufficient for blood aspiration. In some instances, the catheter 460 of the transfer device 400 can have a length that is associated with a minimal desired flow rate therethrough (e.g., a length such that the distal end of the catheter 460 is about 64.5 mm beyond a PIV hub and/or beyond an insertion point of a PIV. In other instances, a catheter having an inner diameter substantially similar to an inner diameter of the catheter 460 can have a length greater than the length of the catheter 460 while still allowing for a sufficient flow rate therethrough.

In a similar manner, and for the purposes of the study described herein, branch vessels having a diameter of 1.0 mm or less were not considered to contribute sufficient blood flow to the vein and thus, were not considered suitable. That is to say, branch vessels having a diameter of 1.0 mm or less were considered to have a volumetric flow rate of blood below a volumetric flow rate threshold. In other instances, however, a branch vessel having a diameter of 1.0 mm can provide a sufficient flow of blood to the vein, such as, for example, in pediatric cases and/or when a PIV is disposed within a vein of the hand or other small vein. Thus, while described above as being based on a size of a branch vessel, in other instances, a branch vessel having any suitable size but having a volumetric flow rate below, for example, the volumetric flow rate threshold may not be suitable.

Figure 15:
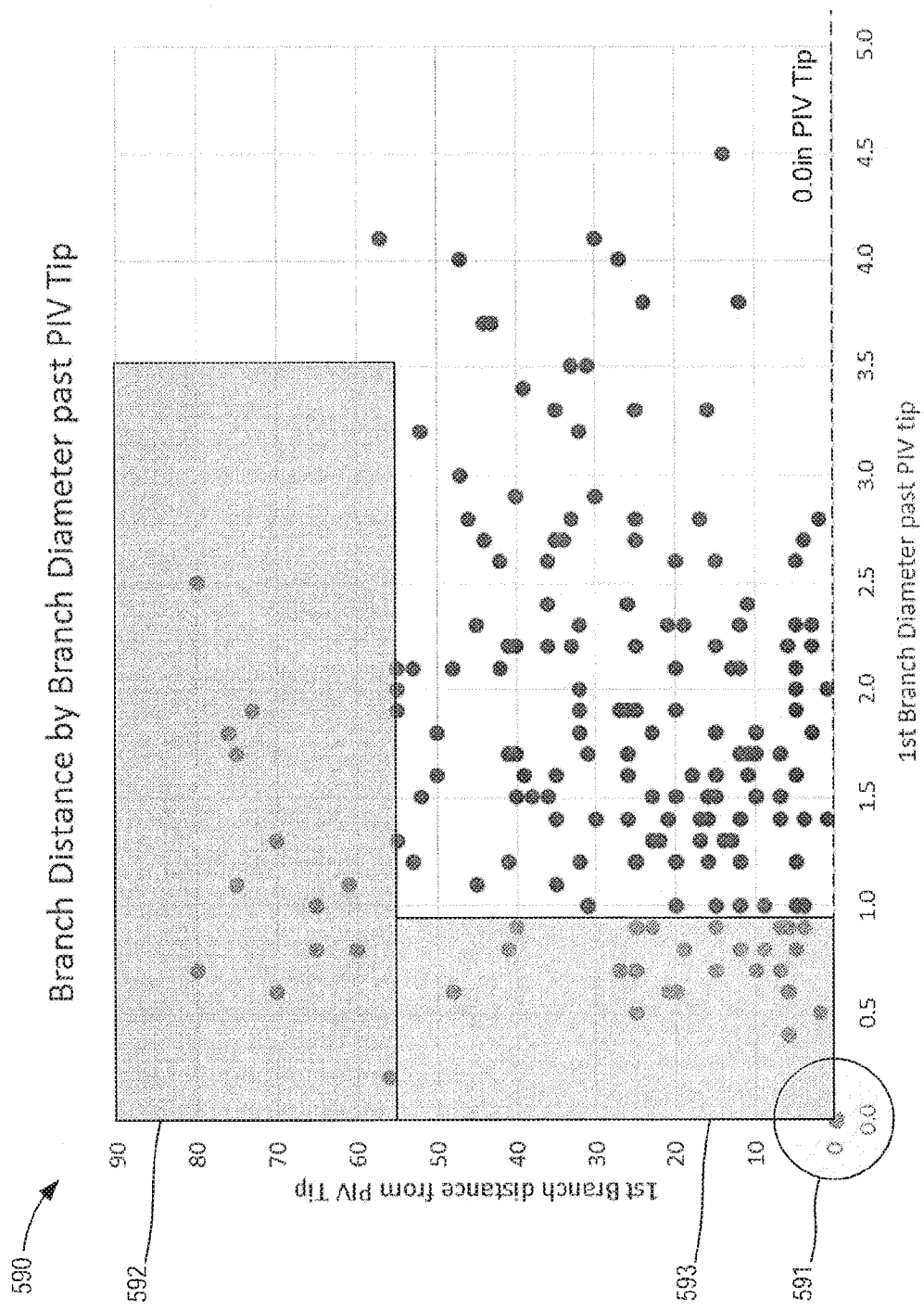
FIGS. 15-18 are graphs illustrating data associated with a diameter of a branch vessel in fluid communication with a vein and a distance from a distal surface of a peripheral intravenous catheter disposed in the vein to the branch vessel, according to various embodiments of the peripheral intravenous catheter.

FIG. 15 illustrates a graph 590 showing data associated with a distance of a first branch vessel from the distal tip of the PIV catheter and the branch vessel diameter when the effective length of the PIV is 0.00 in. In this instance, 23 veins (or 11%) were not in fluid communication with branch vessels within the 8.0 cm (80.0 mm or about 3.15 in), as indicated by region 591 in FIG. 15; 11 veins (or 5%) were in fluid communication with branch vessels beyond approximately 64.5 mm, as indicated by region 592 in FIG. 15; and 28 veins (or 13%) were in fluid communication with branch vessels within approximately 64.5 mm but with a diameter of less than 1.0 mm, as indicated by region 593 in FIG. 15. As such, for a PIV catheter having an effective length of 0.00 in (0.00 mm), 62 veins (or 30%) were not in fluid communication with a branch vessel or were in fluid communication with an unsuitable branch vessel. In other words, 138 veins (or 70%) were in fluid communication with at least one suitable branch vessel (at least as it relates to blood aspiration via an indwelling PIV catheter).

Figure 16:
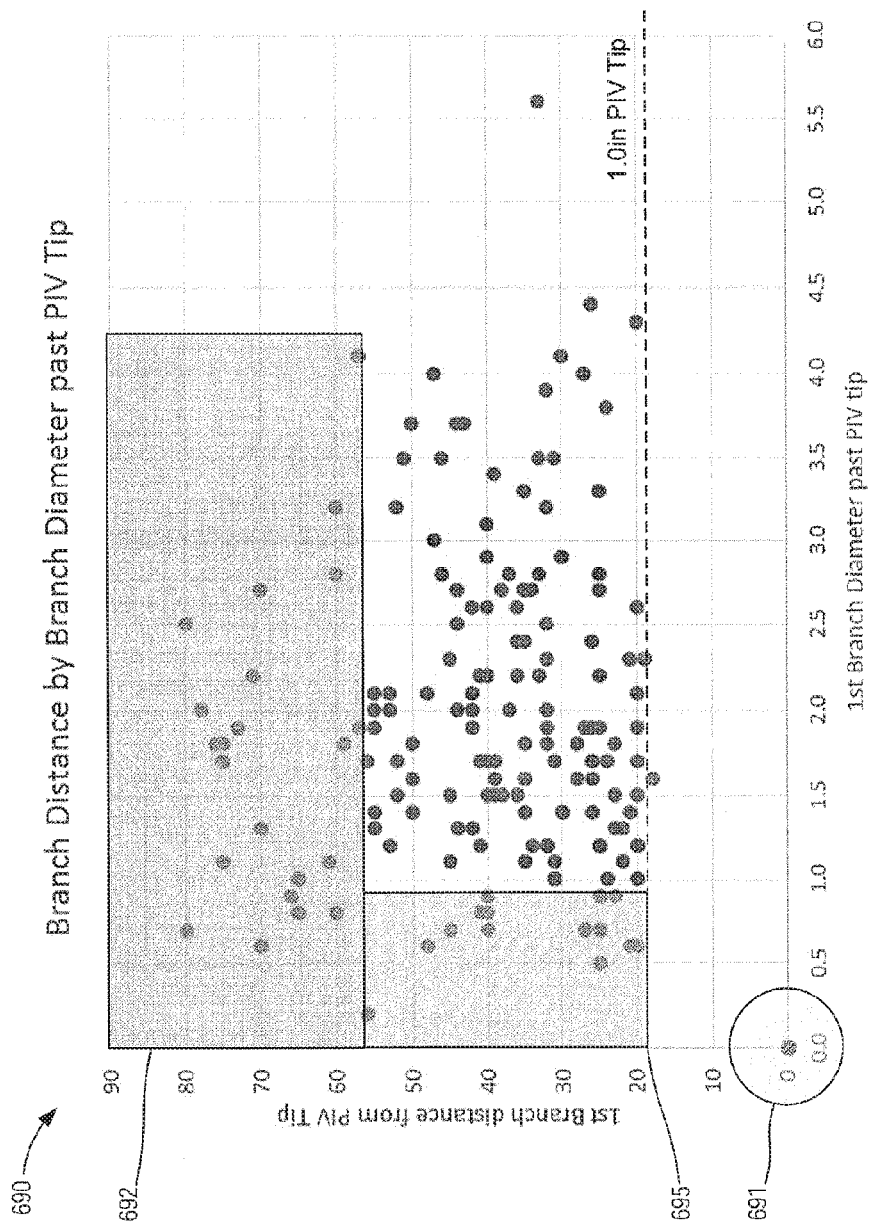

FIG. 16 illustrates a graph 690 showing data associated with a distance of a first branch vessel from the distal tip of the PIV catheter and the branch vessel diameter when the effective length of the PIV is 1.00 in. In this instance, 37 veins (or 18%) were not in fluid communication with branch vessels within the 8.0 cm (80.0 mm or about 3.15 in) from the hypothetical insertion site, 23 veins (or 11%) were in fluid communication with branch vessels beyond approximately 64.5 mm, and 16 veins (or 8%) were in fluid communication with branch vessels within approximately 64.5 mm but with a diameter of less than 1.0 mm, as indicated by regions 691, 692, and 693, respectively, in FIG. 16. As such, for a PIV catheter having an effective length of 1.00 in (25.4 mm), 76 veins (or 36%) were not in fluid communication with a branch vessel or were in fluid communication with an unsuitable branch vessel. In other words, 124 veins (or 64%) were in fluid communication with at least one suitable branch vessel (at least as it relates to blood aspiration via an indwelling PIV catheter).

Figure 17:
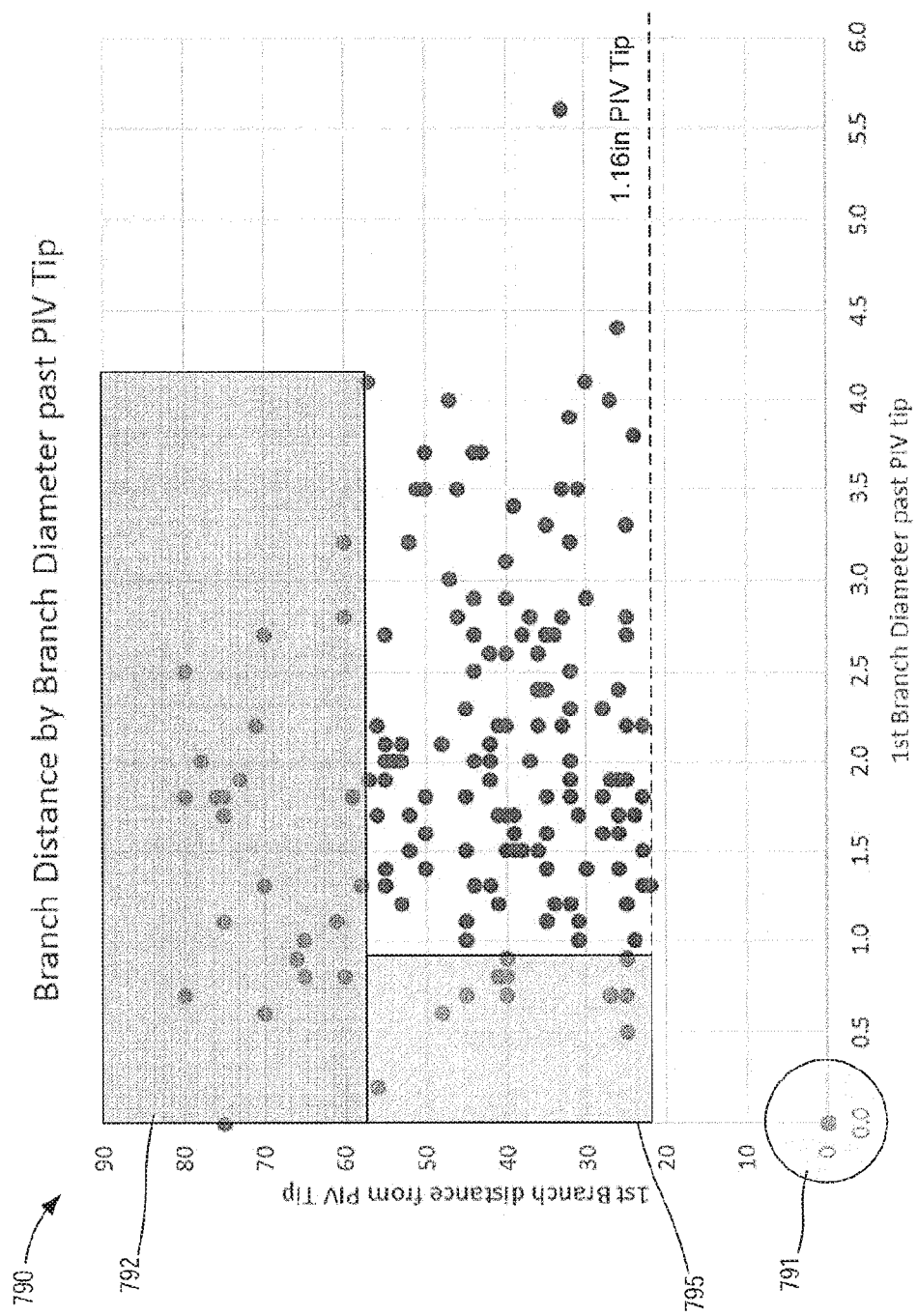

FIG. 17 illustrates a graph 790 showing data associated with a distance of a first branch vessel from the distal tip of the PIV catheter and the branch vessel diameter when the effective length of the PIV is 1.16 in. In this instance, 41 veins (or 20%) were not in fluid communication with branch vessels within the 8.0 cm (80.0 mm or about 3.15 in) from the hypothetical insertion site, as 25 veins (or 12%) were in fluid communication with branch vessels beyond approximately 64.5 mm, and 13 veins (or 6%) were in fluid communication with branch vessels within approximately 64.5 mm but with a diameter of less than 1.0 mm, as indicated by regions 791, 792, and 793, respectively, in FIG. 17. As such, for a PIV catheter having an effective length of 1.16 in (29.46 mm), 79 veins (or 38%) were not in fluid communication with a branch vessel or were in fluid communication with an unsuitable branch vessel. In other words, 121 veins (or 62%) were in fluid communication with at least one suitable branch vessel (at least as it relates to blood aspiration via an indwelling PIV catheter).

Figure 18:
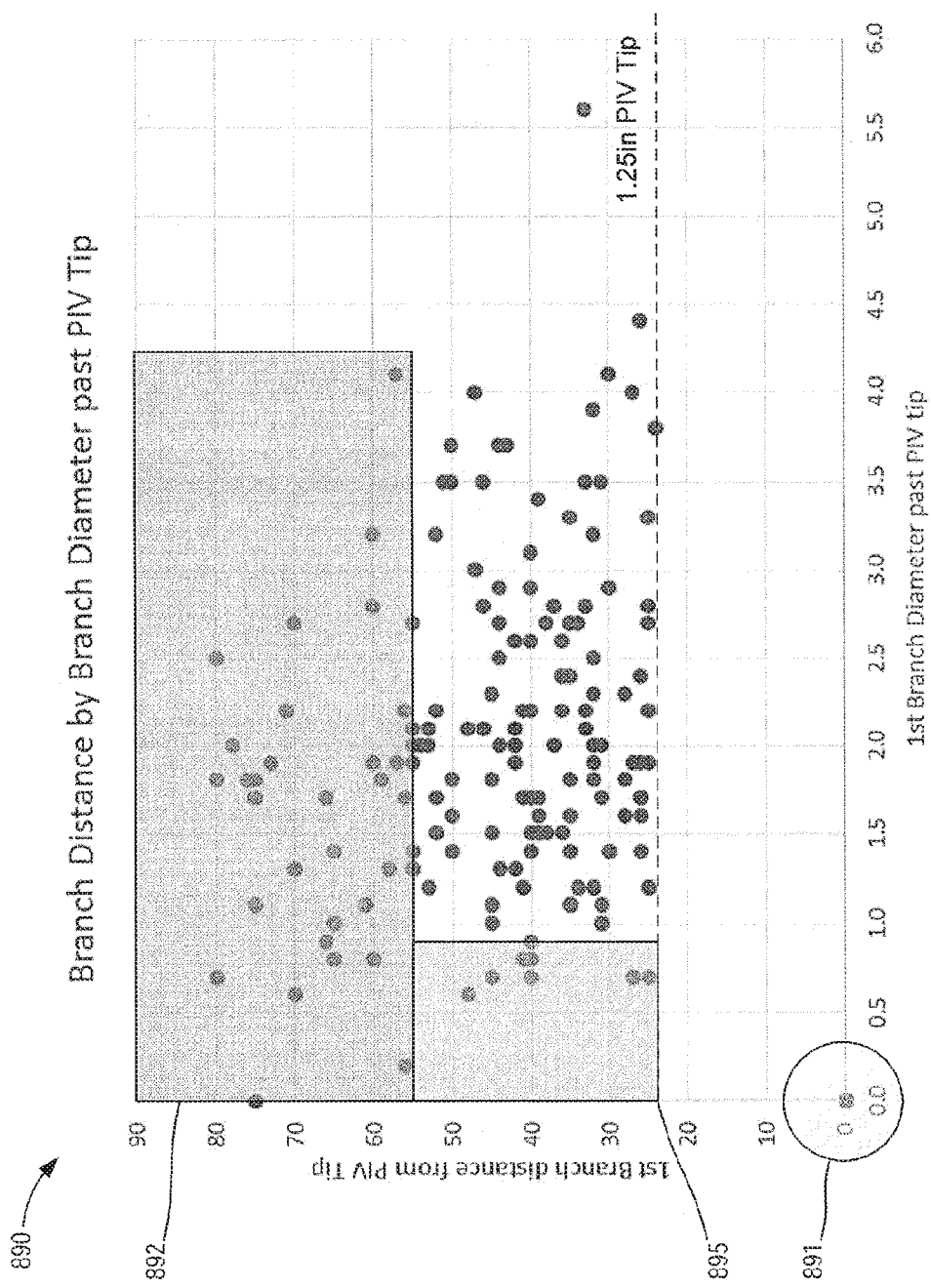

FIG. 18 illustrates a graph 890 showing data associated with a distance of a first branch vessel from the distal tip of the PIV catheter and the branch vessel diameter when the effective length of the PIV is 1.25 in. In this instance, 44 veins (or 21%) were not in fluid communication with branch vessels within the 8.0 cm (80.0 mm or about 3.15 in) from the hypothetical insertion site, 28 veins (or 13%) were in fluid communication with branch vessels beyond approximately 64.5 mm, and 10 veins (or 5%) were in fluid communication with branch vessels within approximately 64.5 mm but with a diameter of less than 1.0 mm, as indicated by regions 891, 892, and 893, respectively, in FIG. 18. As such, for a PIV catheter having an effective length of 1.25 in (31.75 mm), 82 veins (or 39%) were not in fluid communication with a branch vessel or were in fluid communication with an unsuitable branch vessel. In other words, 118 veins (or 61%) were in fluid communication with at least one suitable branch vessel (at least as it relates to blood aspiration via an indwelling PIV catheter).

The mean branch distance and branch diameter were determined and the standard deviations were calculated for effective PIV lengths of 1.00 in (25.4 mm), 1.16 in (29.46 mm), and 1.25 in (31.75 mm), as shown in Table 2 below:

TABLE 2

Mean Branch Distance and Diameter

|  | PIV Length 1.00 in/25.4 mm | | PIV Length 1.16 in/29.46 mm | | PIV Length 1.25 in/31.75 mm | |
| --- | --- | --- | --- | --- | --- | --- |
|  | Mean | Std. Dev. | Mean | Std. Dev. | Mean | Std. Dev. |
| Branch Distance | 32 mm | 20 | 34 mm | 21 | 35 mm | 22 |
| Branch Diameter | 1.6 mm | 1.1 | 1.6 mm | 1.2 | 1.6 mm | 1.2 |

Figure 19:
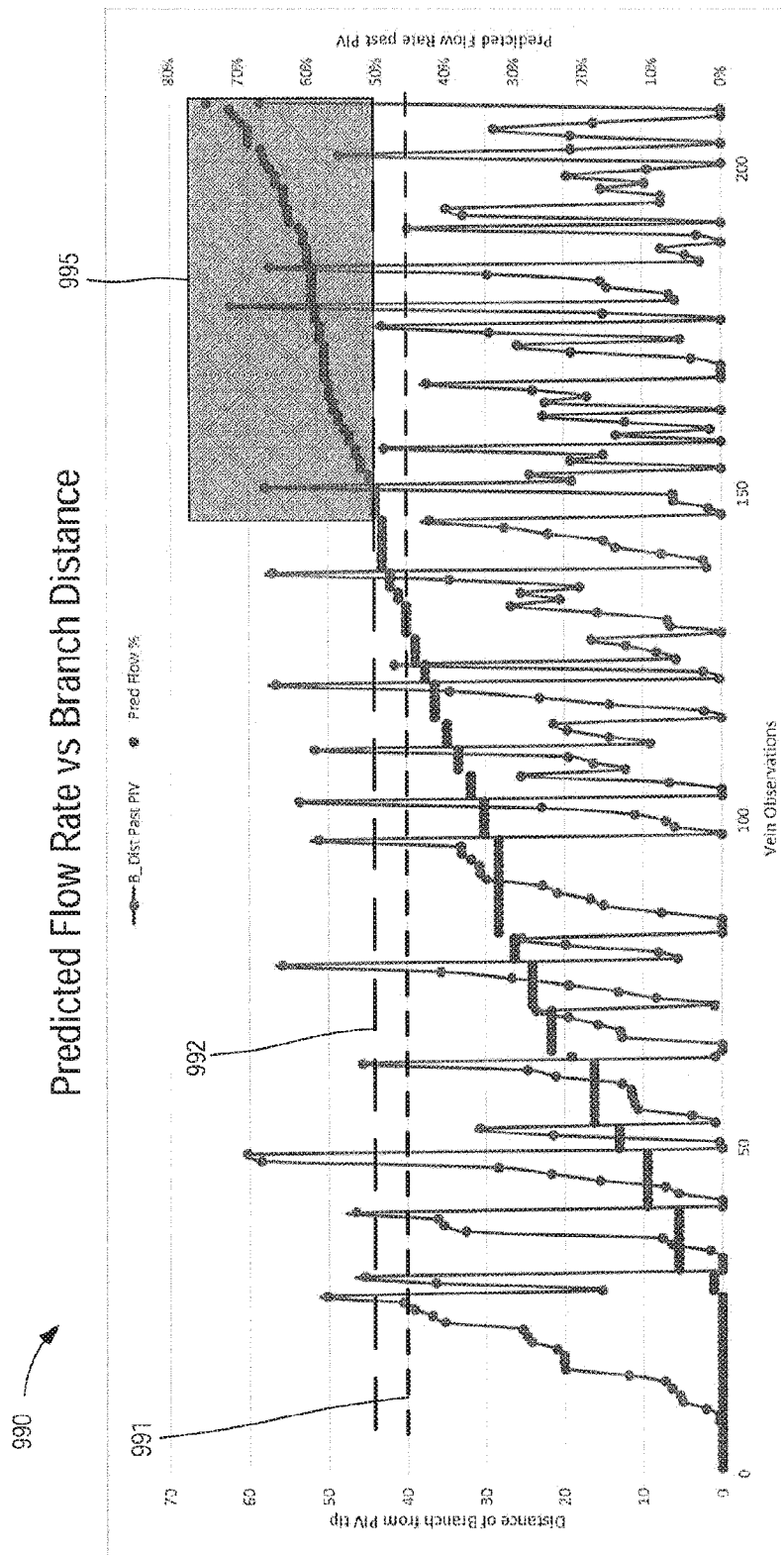
FIG. 19 is a graph illustrating data associated with a predicted flow rate (by percentage) within a portion of a vein and a distance from a distal surface of a peripheral intravenous catheter disposed in the vein to a branch vessel in fluid communication with the vein, according to an embodiment.

FIG. 19 is a graph 990 illustrating data associated with a predicted flow rate (by percentage) within a portion of the vein and a distance from the distal tip of the PIV catheter disposed therein to a branch vessel in fluid communication with the vein. In this instance, a length of 40.0 mm between a distal surface of a catheter (e.g., the catheter 460) and the distal tip of the PIV when the catheter is in the distal most position was proposed (e.g., based at least in part on a flow rate through the catheter), as indicated by line 991 in FIG. 19. Moreover, in this instance, a predicted flow rate of more than 50% through the vein was considered sufficient to support aspiration without branch vessels in fluid communication with the vein (e.g., within the 8.0 cm (80.0 mm or about 3.15 in) from the hypothetical insertion site), as indicated by line 992 and region 993 in FIG. 19.

Figure 20:
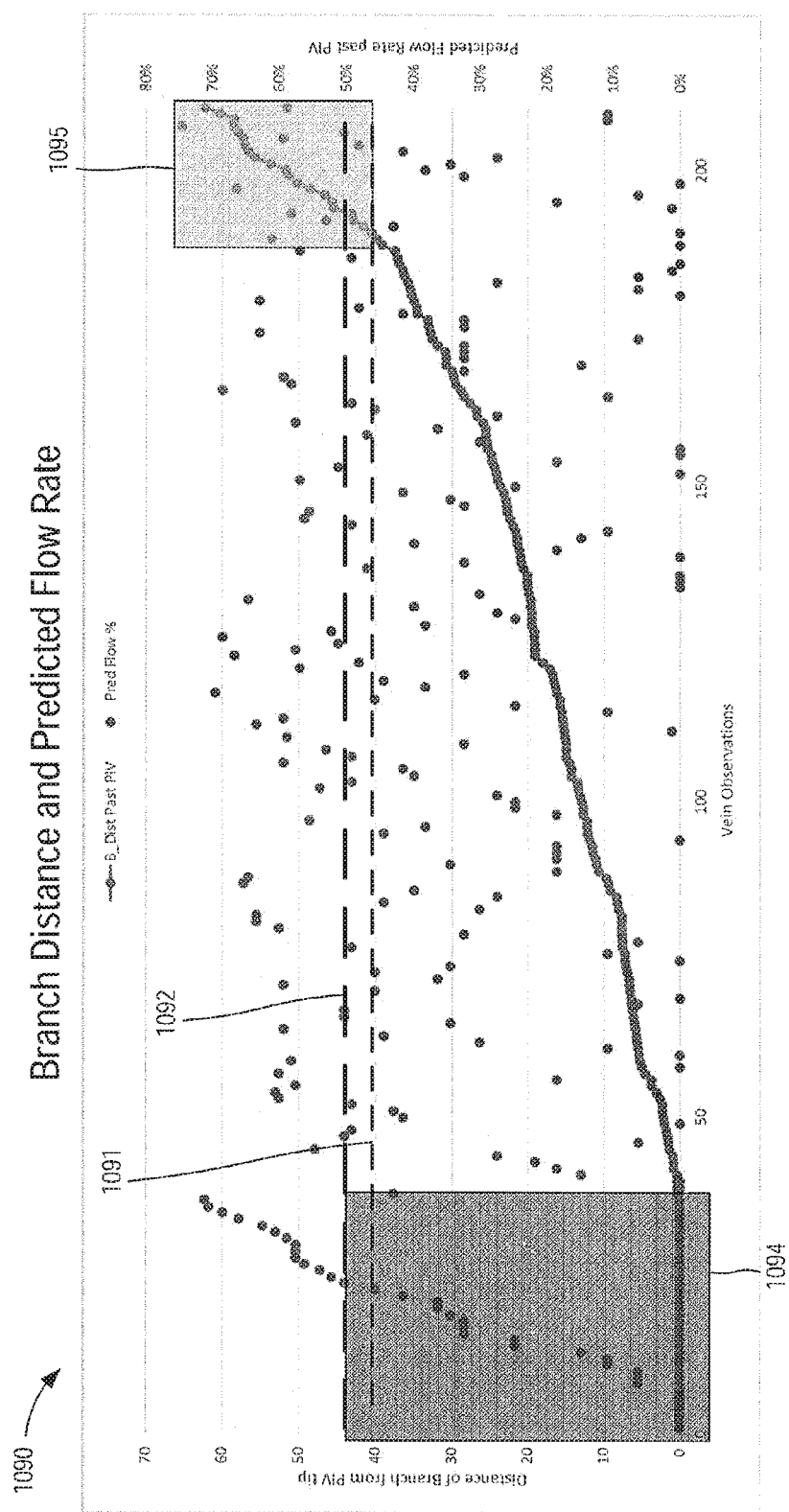
FIG. 20 is a graph illustrating data associated with a predicted flow rate (by percentage) within a portion of a vein and a distance from a distal surface of a peripheral intravenous catheter disposed in the vein to a branch vessel in fluid communication with the vein, according to an embodiment.

FIG. 20 is a graph 1090 illustrating another relationship between the predicted flow rate (by percentage) within a portion of the vein and a distance from the distal tip of the PIV catheter disposed therein to a branch vessel in fluid communication with the vein. In this instances, the length of 40.0 mm and the flow threshold of 50% were maintained (from the graph in FIG. 19), as indicated by the lines 1091 and 1092, respectively, in FIG. 20. Veins that were not in fluid communication with a branch vessel (e.g., within the 8.0 cm (80.0 mm or about 3.15 in) from the hypothetical insertion site) and that had a predicted flow rate of less than 50% are indicated by region 1094 in FIG. 20. Veins that were in fluid communication with branch vessels that were further than 40.0 mm beyond the distal tip of the PIV catheter and within the 80.0 mm from the hypothetical insertion site are indicated by region 1095 in FIG. 20.

Figure 21:
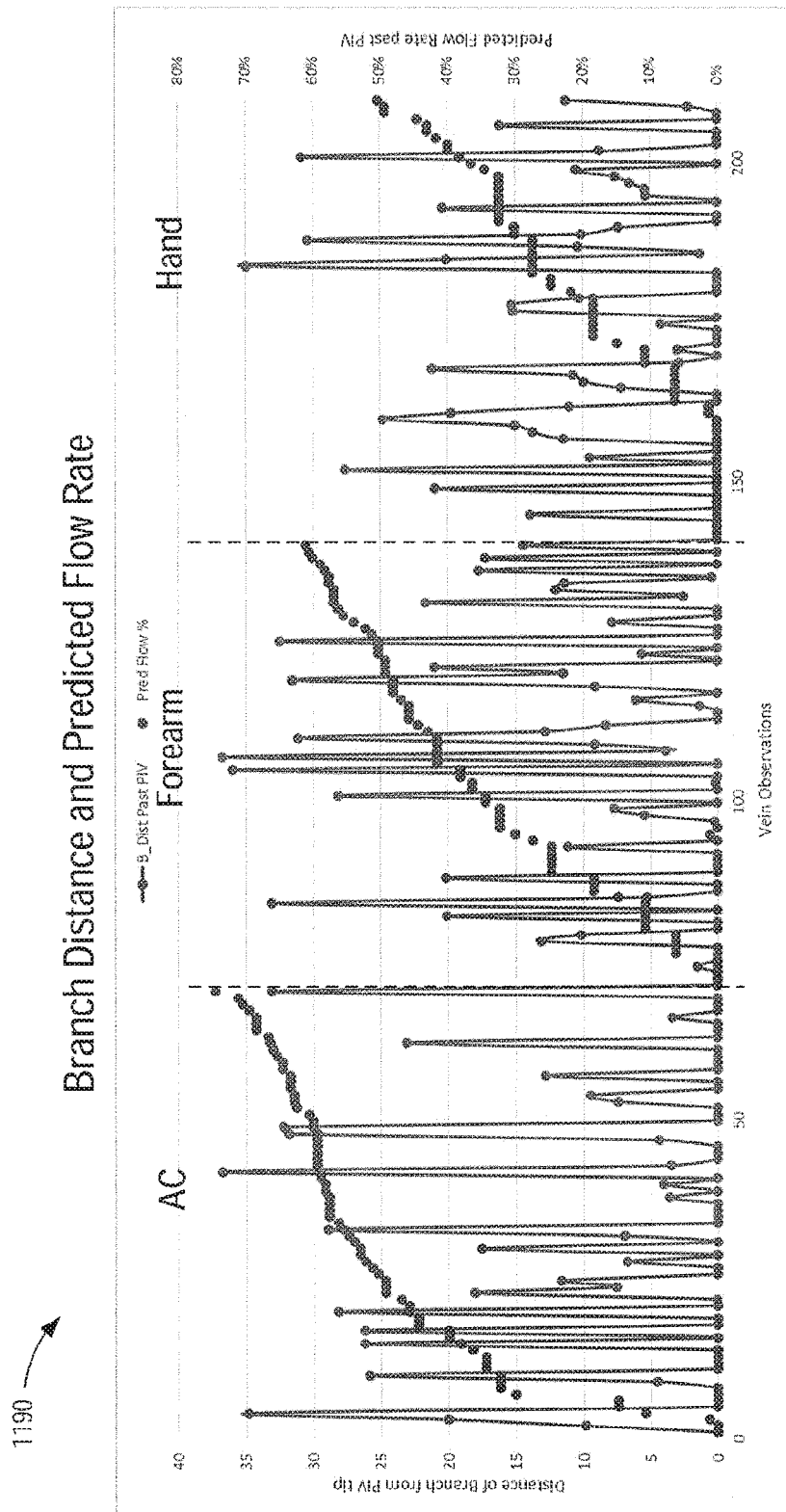
FIG. 21 is a graph illustrating data associated with a predicted flow rate (by percentage) within a portion of a vein of the hand, a portion of a vein of the forearm, and a portion of the antecubital region and a distance from a distal surface of a peripheral intravenous catheter disposed in the vein to a branch vessel in fluid communication with the vein, according to an embodiment.

FIG. 21 is a graph 1190 illustrating data associated with a predicted flow rate (by percentage) within a portion of a vein of the hand (e.g., the hand 30 in FIG. 1), a portion of a vein of the forearm (e.g., the forearm 10 in FIG. 1), and a portion of the antecubital (AC) region (e.g., an antecubital region 28 in FIG. 1) and a distance from the distal tip of the PIV catheter disposed therein to a branch vessel. As shown in the graph 1190, branches in fluid communication with the vein in the AC region were further from the distal tip of the PIV and the vein had an overall higher predicted flow rate than the vein of the forearm, which in turn, had an overall higher predicted flow rate and was in the fluid communication with branches that were further from the distal tip of the PIV than the vein of the hand. Such results were predictable based at least in part on decreasing vein diameter as the vein extends distally from the AC region to the hand.

Figure 22:
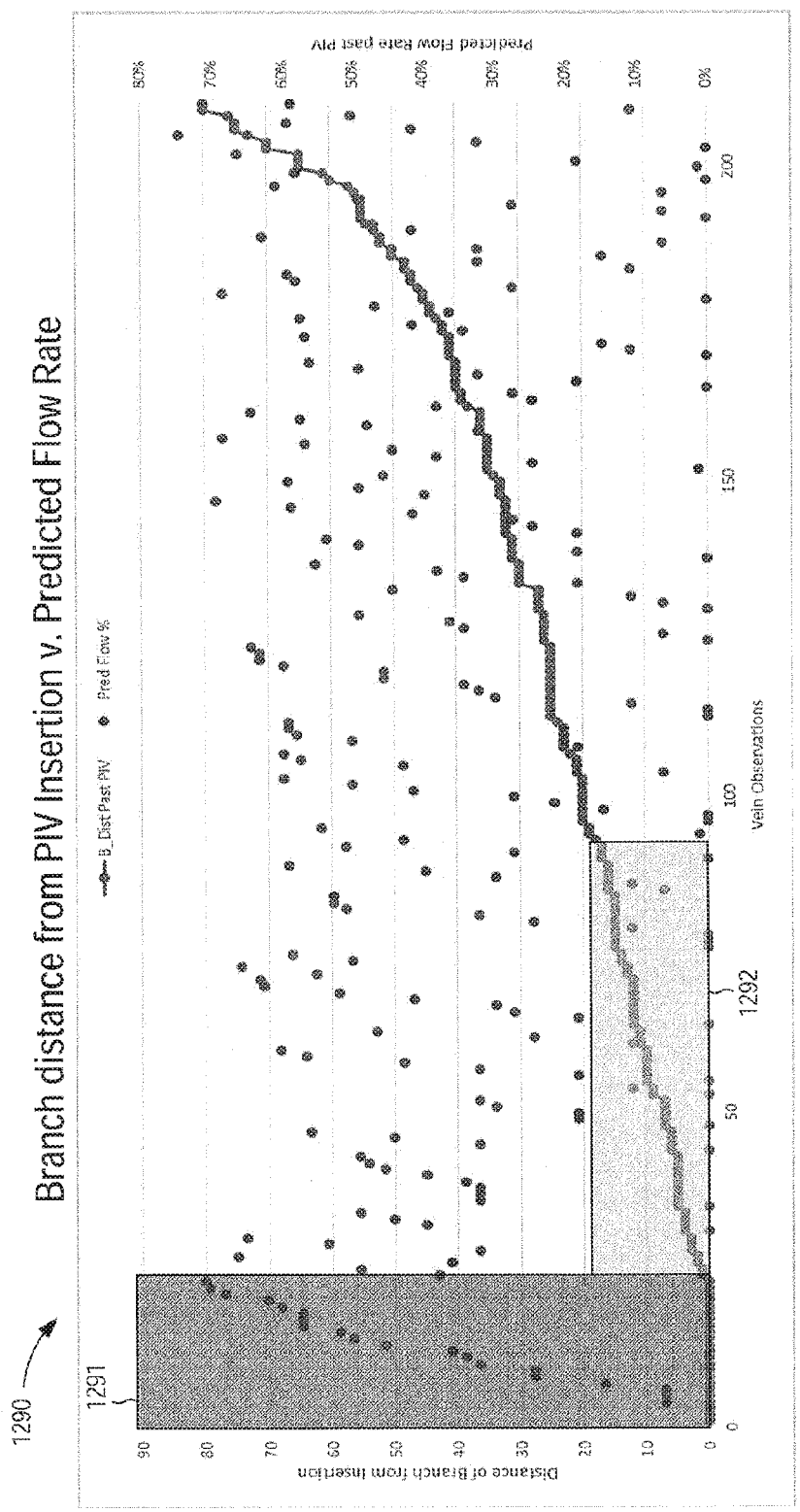
FIG. 22 is a graph illustrating data associated with a predicted flow rate (by percentage) within a portion of a vein and a distance from an insertion point of a peripheral intravenous catheter into the vein to a branch vessel in fluid communication with the vein, according to an embodiment.

FIG. 22 is a graph 1290 illustrating data associated with a predicted flow rate (by percentage) within a portion of a vein and a distance from the hypothetical insertion point of the peripheral intravenous catheter into the vein to a branch vessel in fluid communication with the vein. As described above with reference to Table 1 and the graph 590 in FIG. 15, 23 veins (or 11%) were not in fluid communication with a branch vessel within the 8.0 cm (80.0 mm or about 3.15 in) from the hypothetical insertion site, as indicated by the region 1291 in FIG. 22. Branch vessels within 1.0 in (25.4 mm) of the hypothetical point of PIV catheter insertion were found in 70 veins (or 33%), as indicated by region 1292 in FIG. 22. Moreover, 187 veins (or 89%) were in fluid communication with at least one branch vessel; 121 veins (or 58%) were in fluid communication with at least two branch vessels; and 43 veins (or 20%) were in fluid communication with a third branch vessel.

As shown in FIGS. 15-22 and described above in at least Table 1, a predicted flow rate through a vein can be based at least in part on a size and/or diameter of the vein (e.g., whether the vein is in the antecubital region, the forearm, or the hand), the existence of one or more branch vessels in fluid communication with the vein (e.g., within a predetermined distance such as, for example, 8.0 cm), the distance between the branch vessels and the distal tip of the PIV catheter, and a diameter of the branch vessels. Moreover, the success of blood aspiration via a blood draw catheter accessing a vein through an indwelling PIV catheter can be based at least in part on the venous anatomy (just described) and the distance between a distal surface of the blood draw catheter (e.g., the catheters 360 and/or 460) and the distal tip of the PIV catheter.

For example, FIGS. 23-28 are graphs illustrating data associated with a predicted rate of success for blood aspiration and a distance within a vein from a distal tip of a PIV catheter to a distal surface of the blood draw catheter (e.g., a hypothetical and/or modeled distance—no catheters were inserted into the body during the study described herein). Scenarios were modeled each of which reflected different inputs and/or characteristics and the predicted rate of success associated with each scenario was calculated, as shown below in Table 3 and Table 4, respectively:

TABLE 3

| | Inputs | | | | | |
|---|---|---|---|---|---|---|
| | 1 | 2 | 3 | 4 | 5 | 6 |
| Flow Threshold (%) | 33 | 33 | 33 | 33 | 33 | 33 |
| Applied Tourniquet | 0 | 30 | 0 | 30 | 0 | 30 |
| Diameter Change (%) | | | | | | |
| Diameter (%) | 150 | 150 | 150 | 150 | 150 | 150 |
| Insert Angle | 30 | 30 | 30 | 30 | 30 | 30 |
| PIV Exposed | 4 | 4 | 4 | 4 | 4 | 4 |
| Central Buffer | Std. | Std. | 40.0 | 40.0 | 0.0 | 0.0 |
| Peripheral Buffer | Std. | Std. | Std. | Std. | 0.0 | 0.0 |

Table 4

| | Success Rates (Percentage) | | | | | |
|---|---|---|---|---|---|---|
| | 1 | 2 | 3 | 4 | 5 | 6 |
| 15 mm | 70% | 82% | 78% | 88% | 66% | 80% |
| 25 mm | 75% | 86% | 81% | 90% | 73% | 86% |
| 30 mm | 78% | 87% | 82% | 90% | 75% | 87% |
| 35 mm | 81% | 89% | 83% | 91% | 79% | 89% |
| 40 mm | 81% | 90% | 83% | 91% | 81% | 90% |

Characteristics associated with a PIV catheter such as, for example, a Jelco® 1.0 in, 20 gauge catheter and/or characteristics associated with how such a PIV catheter is inserted into a vein were modeled (e.g., simulated, etc.). For example, as shown in Table 3, a PIV insertion angle of approximately 30° ("Insert Angle" in Table 3) was assumed and approximately 4 mm of the PIV catheter was assumed to be exposed or outside of the body ("NV Exposed" in Table 3). In these instances, a threshold diameter of branch vessels as a percentage of a diameter of the blood draw catheter was fixed at 150% ("Diameter (%)" in Table 3). As described in further detail herein, a desired length of the blood draw catheter (e.g., the catheter 360 of the device 300 and/or the catheter 460 of the device 400) can be determined based at least in part on a calculated success rate.

Figure 23:
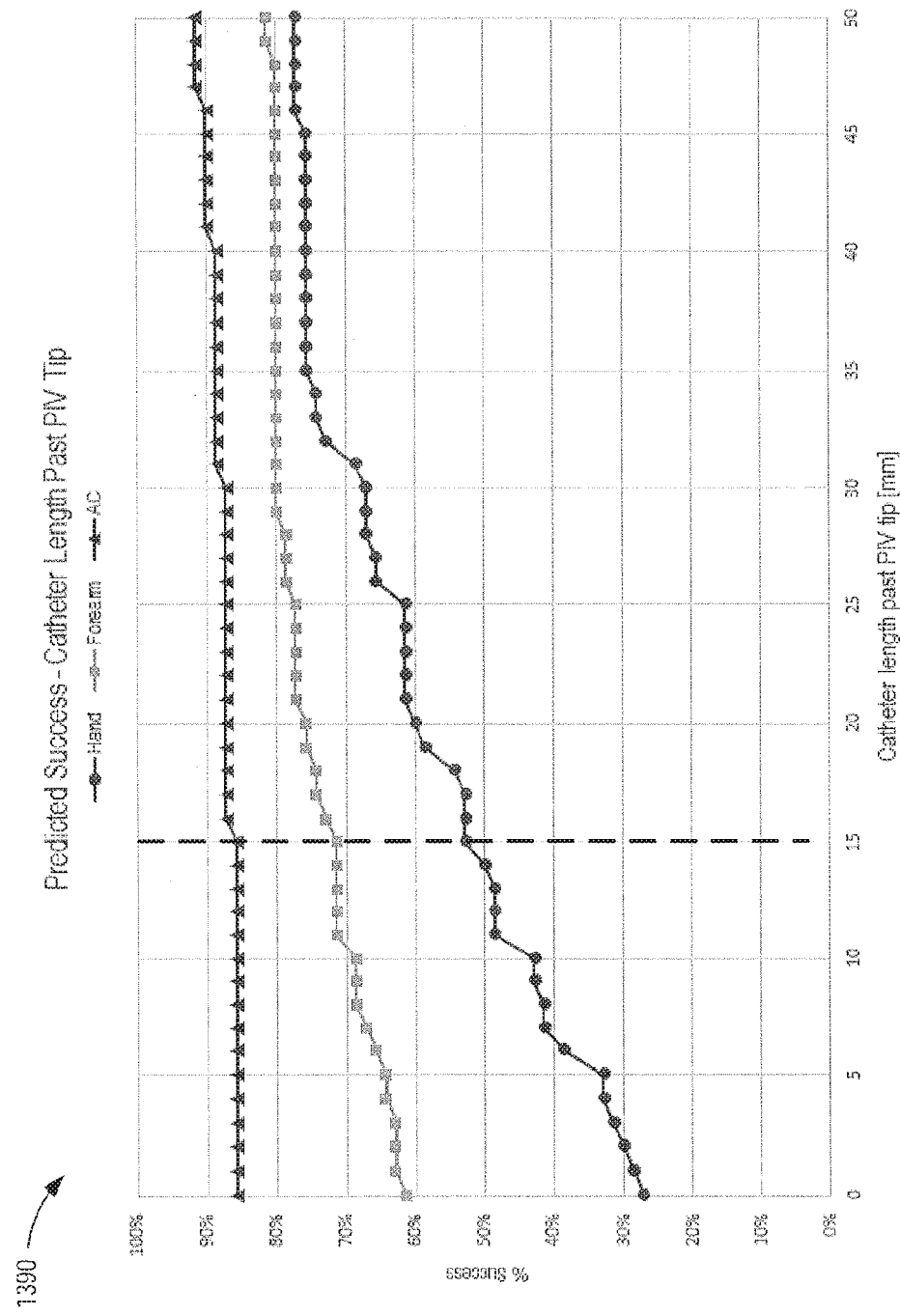
FIGS. 23-28 are graphs illustrating data associated with a distance within a vein from a distal surface of a peripheral intravenous catheter to a distal surface of a blood aspiration catheter extending therethrough and predicted success rate associated with placing the distal surface of the blood aspiration catheter in a portion of the vein having a desired set of characteristics, according to various embodiments.

FIG. 23 is a graph 1390 illustrating the predicted rate of success for blood aspiration under a first scenario (Scenario "1" in Tables 3 and 4). In this example, a flow rate of about 33% around the hypothetical indwelling PIV was assumed, as indicated by the "Flow Threshold (%)" in Table 3. In other words, a 33% occlusion of the lumen of the vein modeled. As shown in Table 3, in this example, a standard buffer size associated with a central branch and a standard buffer size associated with a peripheral branch were modeled. Specifically, the standard buffer size (or desired distance from the branch vessel) for a central branch vessel having a diameter between about 0.0 mm and about 1.0 mm was 2.5 mm; the standard buffer size for a central branch vessel having a diameter between about 1.0 mm and about 2.0 mm was 5.0 mm; the standard buffer size for a central branch vessel having a diameter between about 2.0 mm and about 3.0 mm was 10.0 mm; and the standard buffer size for a central branch vessel having a diameter greater than about 3.0 mm was 20.0 mm. Similarly, the standard buffer size for a peripheral branch vessel having a diameter between about 0.0 mm and about 1.0 mm was 1.0 mm; the standard buffer size for a peripheral branch vessel having a diameter between about 1.0 mm and about 2.0 mm was 5.0 mm; the standard buffer size for a peripheral branch vessel having a diameter between about 2.0 mm and about 3.0 mm was 5.0 mm; and the standard buffer size for a peripheral branch vessel having a diameter greater than about 3.0 mm was 5.0 mm.

As described in detail above, the device 300 can be used to aspirate a volume of blood from a vein via an indwelling PIV. In such instances, the reach of the catheter 360 beyond a distal end of an indwelling PIV catheter such as a Jelco® 1.0 in, 20-gauge PIV (e.g., a hypothetical PIV catheter in this case) is about 15 mm and is indicated in FIG. 23 by the dashed vertical line. The modeled/predicted success rates associated with blood draw through the catheter (e.g., the catheter 360) in such instances closely matched empirical results associated with actual use of the catheter for blood aspiration. The close matching of such results, for example, provides validation for the accuracy of the model and/or the assumptions associated with the model. Therefore, based at least in part on the validation of the modeled and/or predicted success rates of the catheter (e.g., the catheter 360) disposed at, for example, 15.0 mm beyond the distal end of the PIV (either empirically or hypothetical) it was determined that the model could be used to calculate predicted success rates for aspiration of blood through a hypothetical blood draw catheter based on a distance between a distal surface of the catheter and the distal tip of the PIV catheter (e.g., a hypothetical PIV catheter disposed in the vein). By comparing the predicted success rates, a desired distance between the distal surface of the catheter and the distal tip of the PIV catheter can be determined. For example, in assuming the parameters and/or characteristics shown in column 1 of Table 3, the desired length between the distal surface of the catheter and the distal tip of the PIV catheter was determined to be about 35.0 mm having a predicted overall success rate of about 81% (as indicated in Table 4).

Figure 24:
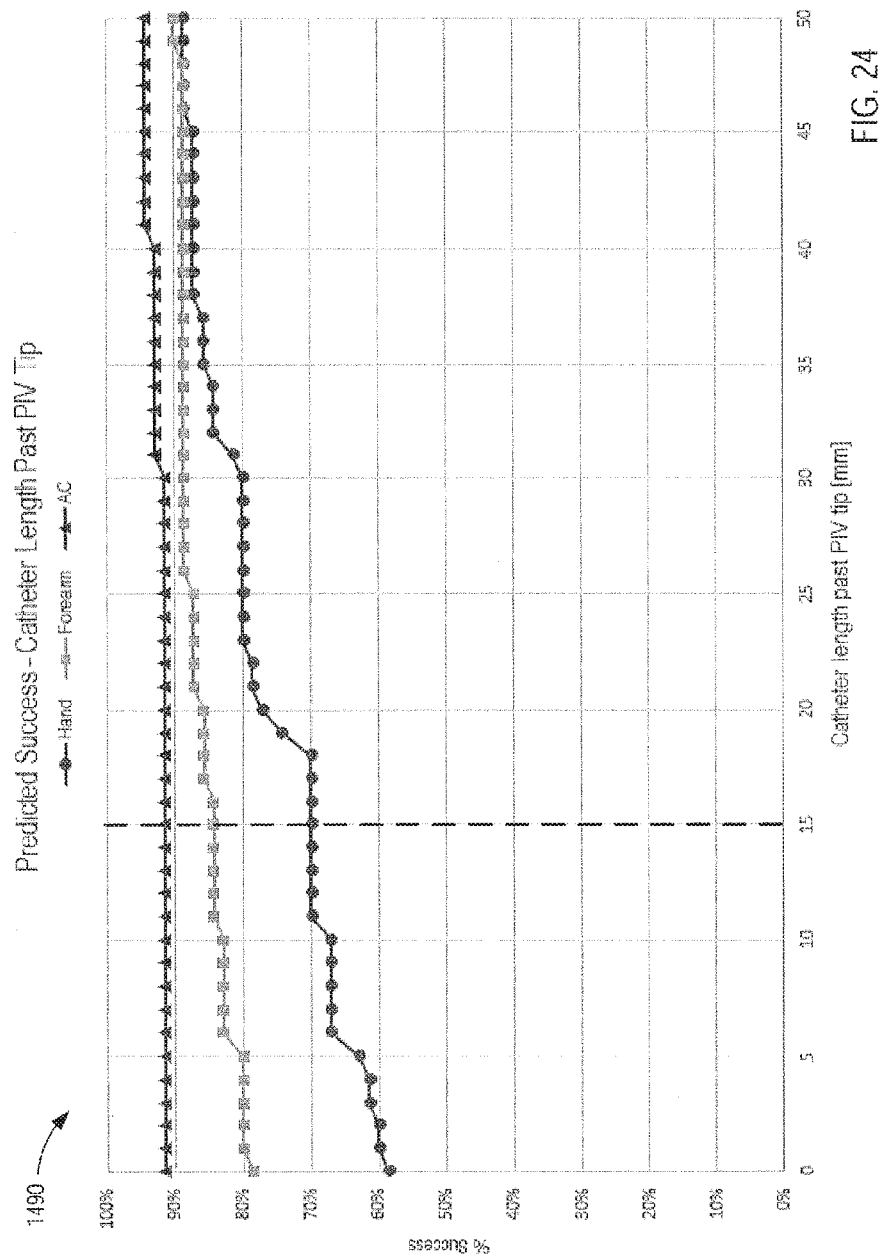

FIG. 24 is a graph 1490 illustrating the predicted rate of success for blood aspiration under a second scenario (Scenario "2" in Tables 3 and 4). In this example, the only change from scenario "1" was the application of a tourniquet proximal to the PIV catheter insertion site. In this example, the application of the tourniquet was considered to increase the size of the vein by about 30%. More specifically, the application of a tourniquet downstream of (e.g., proximal to) a PIV insertion point increases the pressure within the vein, which in turn, results in a swelling or increase in diameter of the vein. In some instances, the increase in the diameter of the vein can be based at least in part on the gender of the subject. For example, in some instances, the application of a tourniquet on a male subject can increase a diameter of a vein, for example, by about 25%, while the application of a tourniquet on a female subject can increase a diameter of a vein, for example, by about 45%. In some instances, the increase in diameter of the vein can be based at least in part on a diameter of the vein without the application of a tourniquet. When the application of a tourniquet is considered, for example, to result in a percentage increase in area of a vein, the percentage increase in area is substantially the same for males and females. That is to say, an area increase of a vein resulting from an application of a tourniquet is substantially independent of gender (e.g., is independent of common differences in the size of veins between males and females). In other words, the resultant change on the vein diameter results in an equivalent change in pressure or volume, thus a smaller vein diameter distends to a larger percentage of diameter than a vein having a larger diameter; however, the resultant change in the cross sectional area is substantially equal. As shown in Tables 3 and 4, in this instance, the percentage of increase in the area of the vein was assumed and/or modeled at 30%. Thus, with all other inputs remaining the same, the predicted success rates for aspiration of blood through the blood draw catheter were calculated based on a distance between a distal surface of the catheter and the distal tip of the PIV catheter, as shown in Table 4 and the graph 1490 in FIG. 24. By comparing the predicted success rates, a desired distance between the distal surface of the catheter and the distal tip of the PIV catheter was determined to be about 35.0 mm having a predicted overall success rate of about 89% (as indicated in Table 4).

Figure 25:
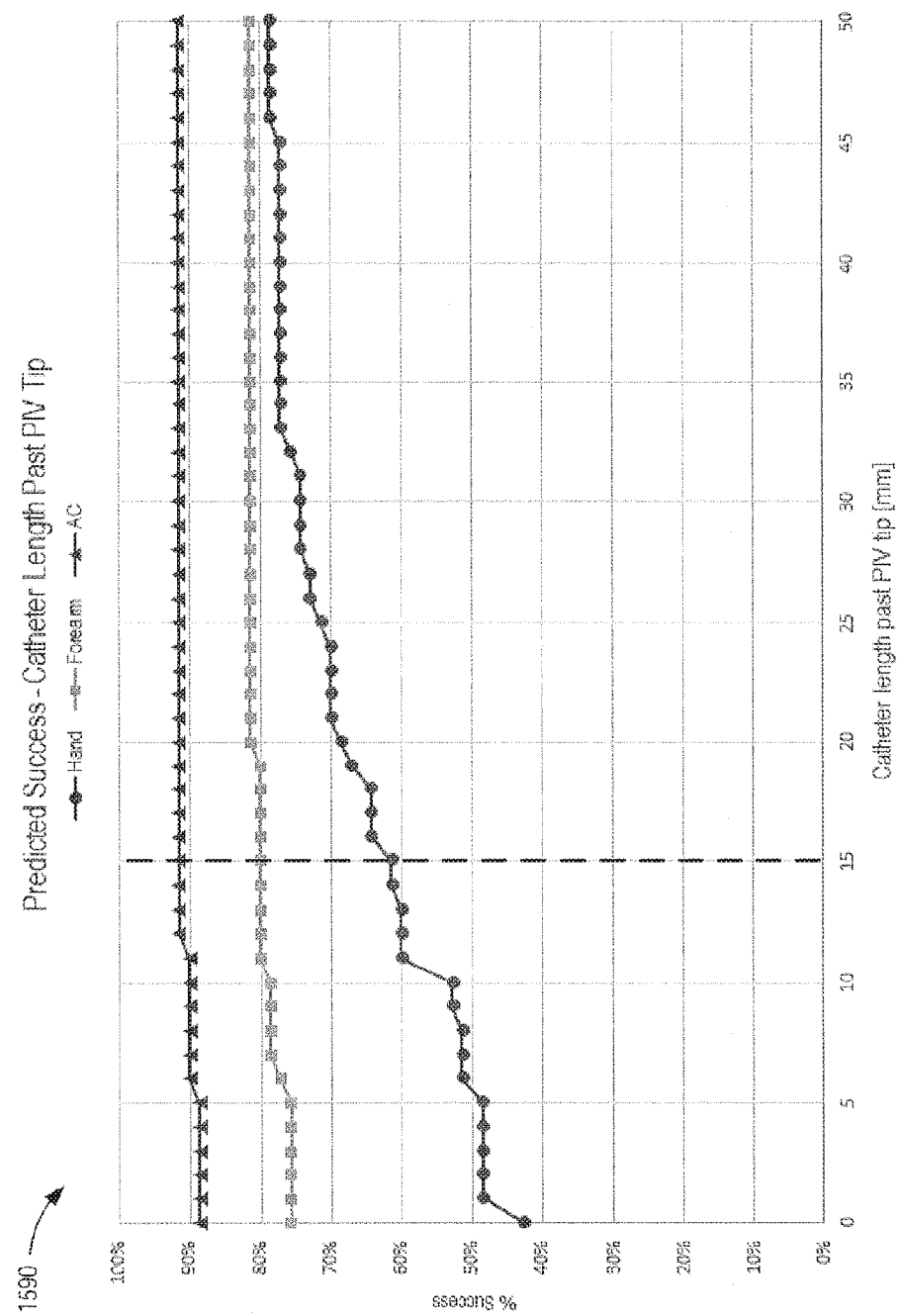

FIG. 25 is a graph 1590 illustrating the predicted rate of success for blood aspiration under a third scenario (Scenario "3" in Tables 3 and 4). In this example, the only change from scenario "1" was the assumption that the distal surface of the catheter reached, for example, a central branch vessel or the buffer zone. Specifically, as shown in Table 3, the buffer zone for the central branch was set to 40.0 mm. In other words, the distal end of the catheter can be about 40.0 mm from the central branch while remaining within the "buffer zone" and/or otherwise by being in fluid communication with a vein having a positive effect on a volumetric flow rate through at least a portion of the vein. Thus, by comparing the predicted success rates, a desired distance between the distal surface of the catheter and the distal tip of the PIV catheter was determined to be about 25.0 mm having a predicted overall success rate of about 81%, as indicated in Table 4.

Figure 26:
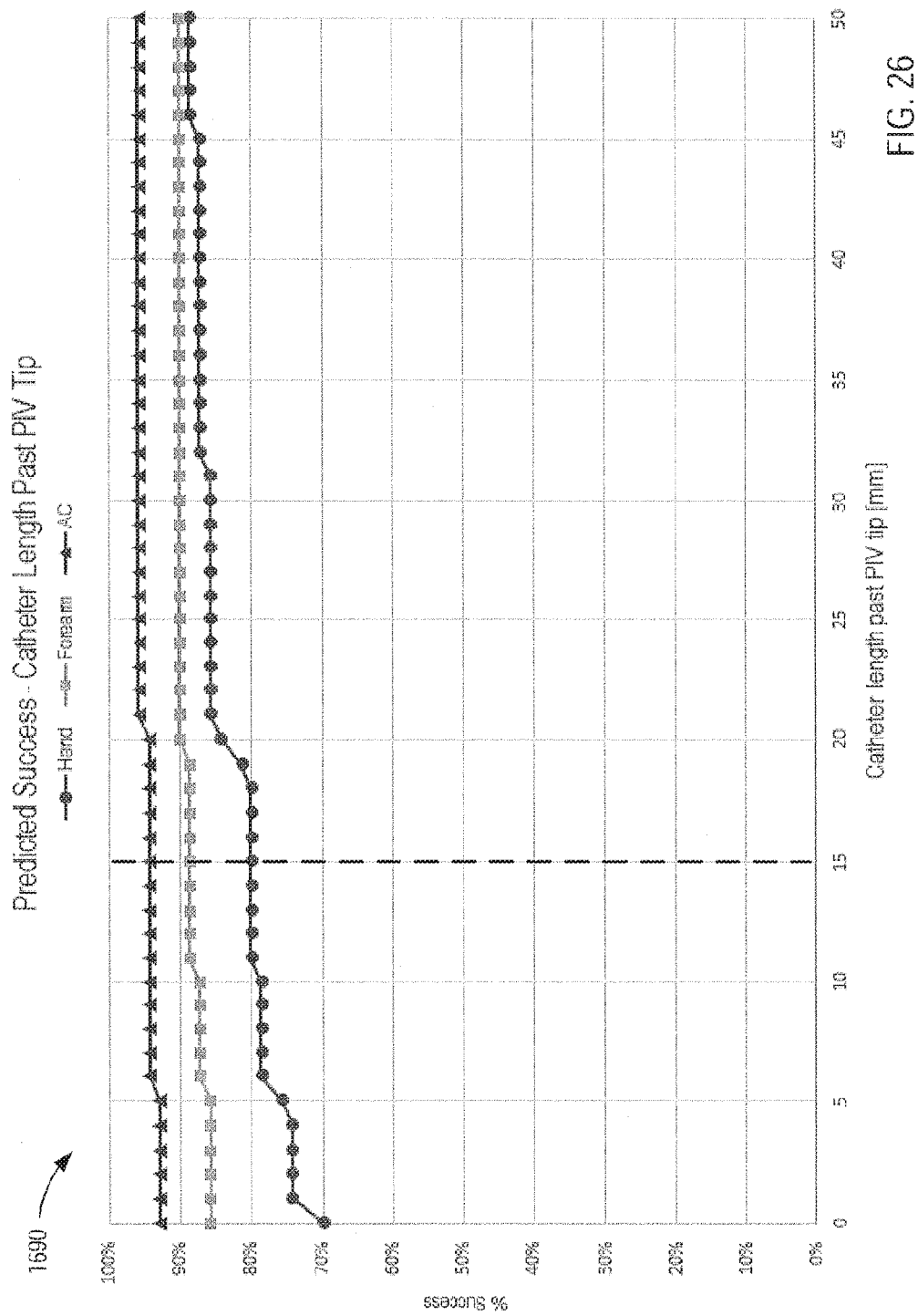

FIG. 26 is a graph 1690 illustrating the predicted rate of success for blood aspiration under a fourth scenario (Scenario "4" in Tables 3 and 4). In this example, the only change from scenario "3" was the application of a tourniquet proximal to the PIV catheter insertion site—assuming an increase in the size of the vein by about 30%, as described above. Thus, by comparing the predicted success rates, a desired distance between the distal surface of the catheter and the distal tip of the PIV catheter was determined to be about 25.0 mm having a predicted overall success rate of about 90%, as indicated in Table 4.

Figure 27:
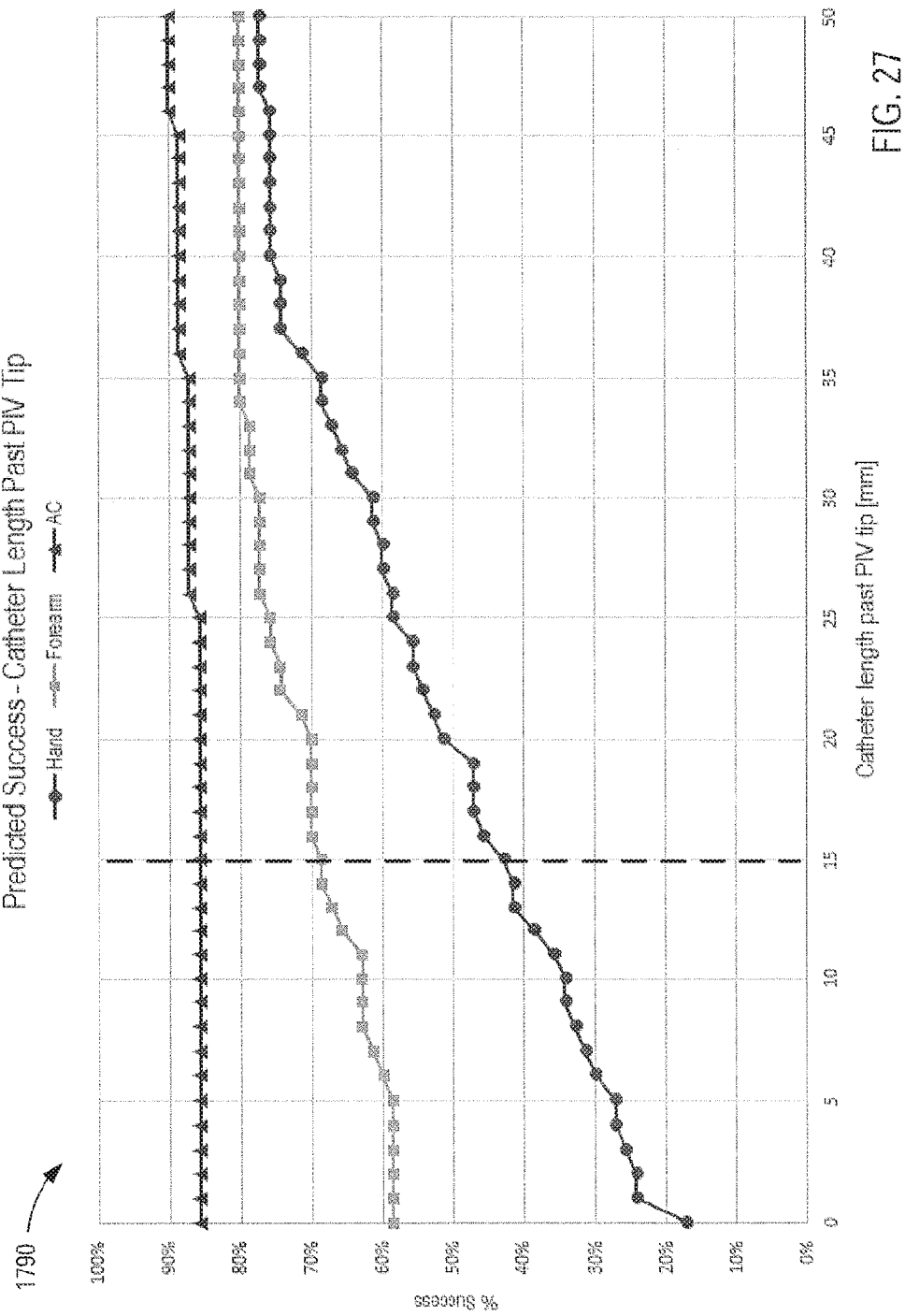

FIG. 27 is a graph 1790 illustrating the predicted rate of success for blood aspiration under a fifth scenario (Scenario "5" in Tables 3 and 4). In this example, the only change from scenario "1" and/or "3" was the buffer zone associated with both central branches and peripheral branches was decreased to 0.0 mm. That is to say, all assumptions associated with one or more buffer zones surrounding a branch vessel were set to zero. Said another way, in this instance, a branch vessel can affect the likelihood of a successful blood draw through a catheter when a distal end of the catheter is disposed at or proximal to (e.g., beyond) the branch vessel. Thus, by comparing the predicted success rates, a desired distance between the distal surface of the catheter and the distal tip of the PIV catheter was determined to be about 35.0 mm having a predicted overall success rate of about 79%, as indicated in Table 4.

Figure 28:
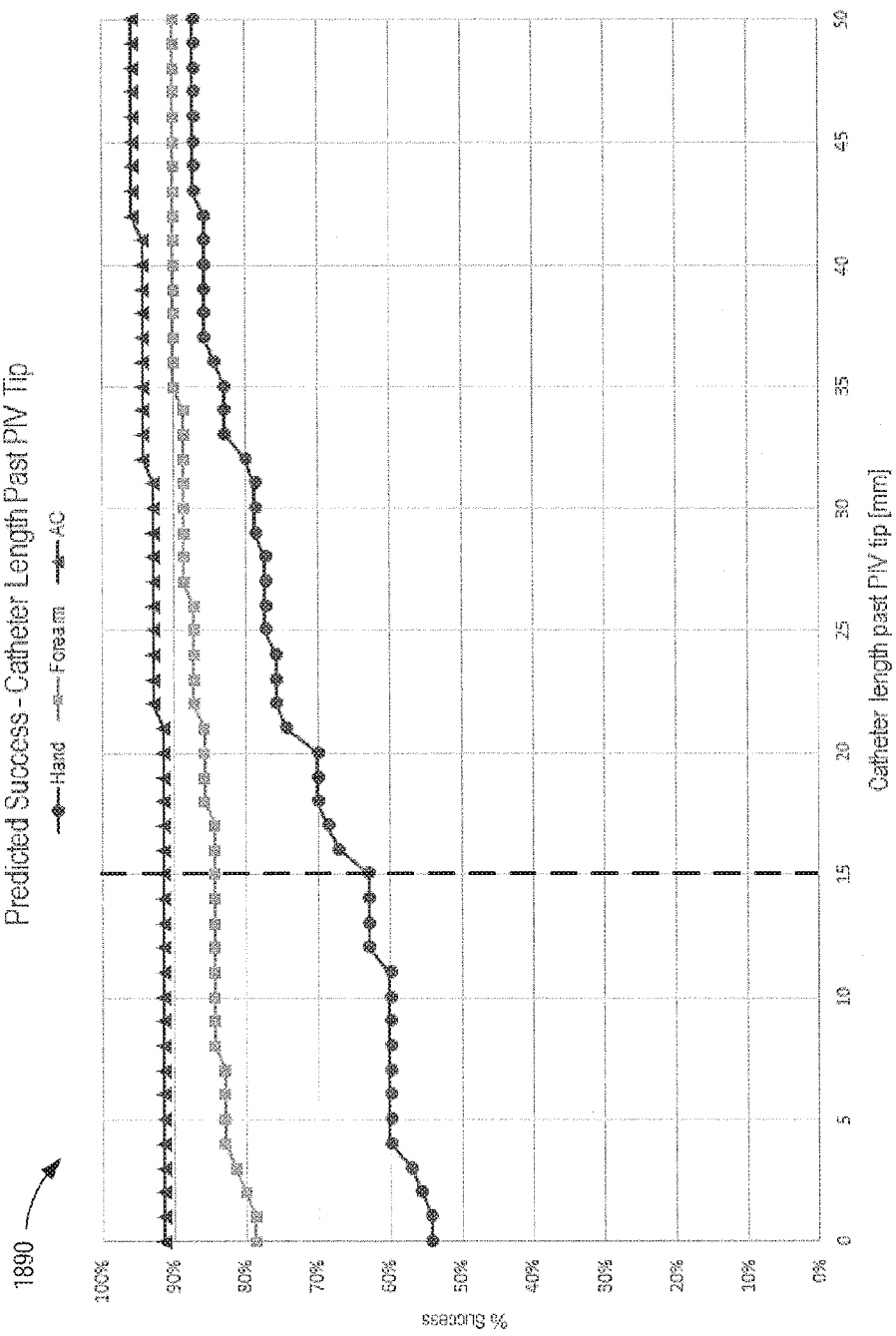

FIG. 28 is a graph 2490 illustrating the predicted rate of success for blood aspiration under a sixth scenario (Scenario "6" in Tables 3 and 4). In this example, the only change from scenario "5" was the application of a tourniquet proximal to the PIV catheter insertion site—assuming an increase in the size of the vein by about 30%, as described above. Thus, by comparing the predicted success rates, a desired distance between the distal surface of the catheter and the distal tip of the PIV catheter was determined to be about 35.0 mm having a predicted overall success rate of about 89%, as indicated in Table 4.

With the predicted success rates calculated for scenarios 1-6, an overall desired distance between a distal surface of a catheter and a distal tip of a PIV catheter dwelling within a vein was determined to be about 30.0 mm. In other words, blood aspiration via a blood draw catheter using an indwelling PIV catheter is more likely to be successful when the distal surface of the catheter (e.g., the catheter 460 of the device 400) is disposed at a distance of about 30.0 mm from the distal tip of the indwelling PIV catheter. While some predicted success rates continued to increase with an increase in distance beyond, for example, 30.0 mm, it was determined that 30.0 mm was desired based on diminishing returns associated with increased lengths of the catheter. Moreover, in some instances, a flow rate through a catheter can be inversely proportional to a length of the catheter. Thus, providing a catheter with a length that places the distal end of the catheter at about 30.0 mm beyond the distal tip of the indwelling PIV can, for example, balance a benefit of potential increase in flow rate through the vein at a further distance with a decreased flow rate through the catheter.

While the transfer device 300 is described above as being configured to place the distal end of the catheter 360 approximately 15.0 mm beyond a distal end of a PIV (e.g., a 1.0 in PIV such as a Jelco® 1.0 in, 20-gauge PIV) when the catheter 360 is in a distal most position, and the transfer device 400 is described above as being configured to place the distal end of the catheter 460 approximately 30.0 mm beyond a distal end of a PIV (e.g., a 1.0 in PIV) when the catheter 460 is in a distal most position, it should be understood, that the catheter 360 and the catheter 460 can be placed in any suitable position proximal or distal to the distal end of the PIV within the 15.0 mm and the 30.0 mm, respectively. For instance, a user may manipulate the transfer device 400 by advancing the catheter 460 (or the transfer device 300 by advancing the catheter 360) relative to an indwelling 1.0 in PIV to its distal most position. If, however, blood draw is unsuccessful and/or a flow of blood through the catheter 460 is below a desired threshold, the user can, for example, move the catheter 460 in a proximal direction relative to the PIV to place the catheter 460 in a position within the vein receiving a desired flow of blood, as described above with reference to, for example, FIGS. 2-6.

Figure 29:
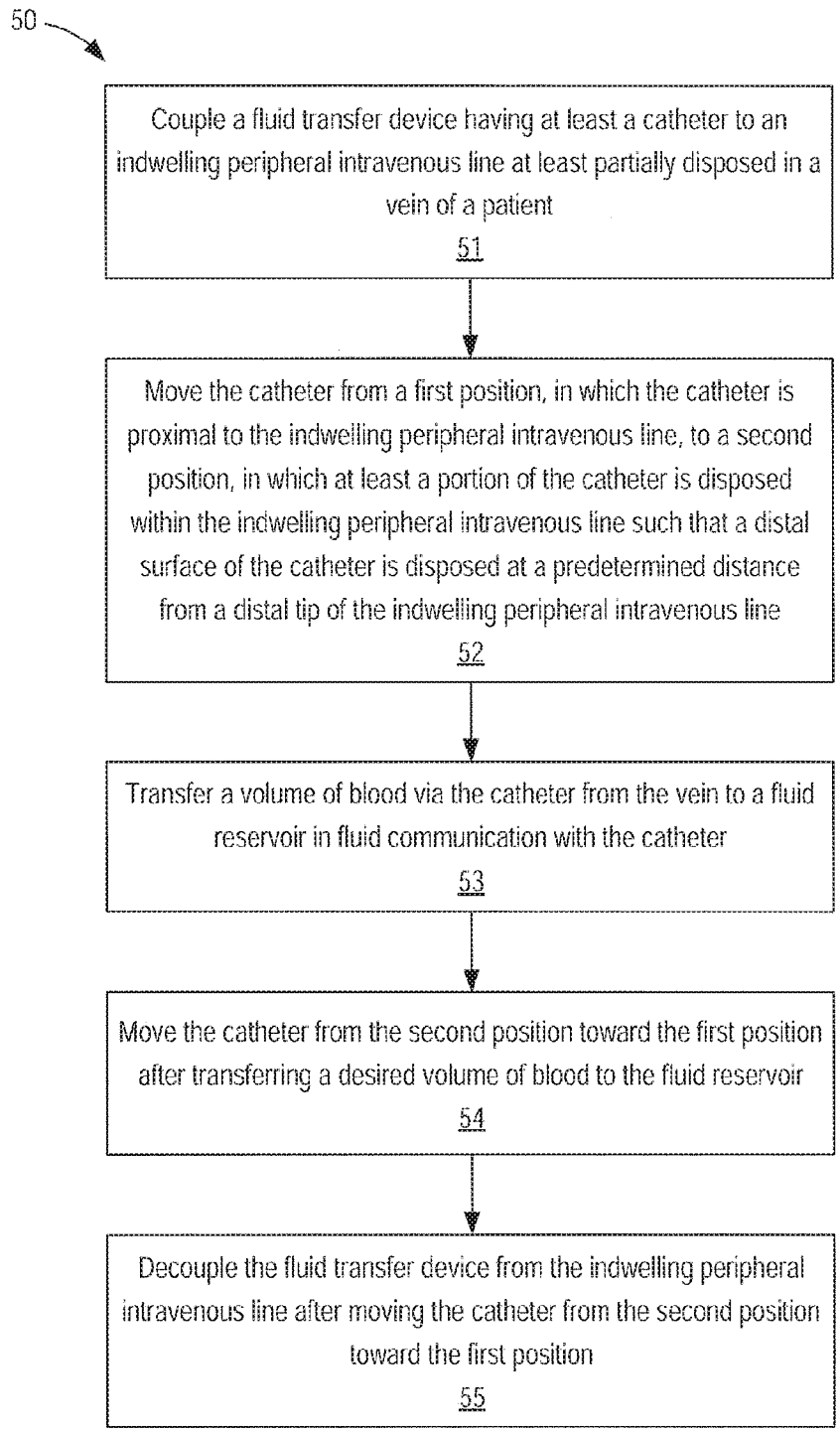
FIG. 29 is a flowchart illustrating a method of using a fluid transfer device to place a catheter within a vein, via an indwelling peripheral intravenous catheter, at a position suitable for blood aspiration, according to an embodiment.

FIG. 29 is a flowchart illustrating a method 50 of using a fluid transfer device to place a catheter within a vein, via an indwelling peripheral intravenous catheter, at a position suitable for blood aspiration, according to an embodiment. The method 50 includes coupling the fluid transfer device to an indwelling peripheral intravenous line (PIV) at least partially disposed in a vein of a patient, at 51. The fluid transfer device can be any suitable device configured for fluid transfer through a PIV. For example, in some embodiments, the fluid transfer device can be substantially similar to the fluid transfer devices 300 and/or 400 described above with reference to FIGS. 8-11 and FIGS. 12-14, respectively. In some embodiments, the fluid transfer device can be substantially similar to any of the fluid transfer devices described in the '834 application incorporated by reference above. In other embodiments, the fluid transfer device can include only a catheter or other suitable fluid conduit. As such, the fluid transfer device can include at least an introducer defining a lumen, a catheter movably disposed in the lumen of the introducer, and an actuator coupled to the catheter. As described above with reference to the transfer device 400, the lumen (or inner volume) of the introducer can have a tortuous cross-sectional shape configured to isolate, at least partially, the catheter disposed in the introducer from a volume outside of the introducer.

With the fluid transfer device coupled to the PIV (and/or an adapter coupled to the PIV), the catheter is moved from a first position, in which the catheter is proximal to the indwelling PIV, to a second position, in which at least a portion of the catheter is disposed within the indwelling PIV such that a distal surface of the catheter is disposed at a predetermined distance from a distal tip of the indwelling PIV, at 52. As described above with reference to the fluid transfer device 400 shown in FIGS. 12-14, the introducer can have an outer surface that defines a set of ribs or the like configured to be in contact with a portion of the actuator such that moving the actuator relative to the introducer advances the portion of the actuator along the ribs. In some embodiments, the movement of the actuator along the ribs can produce a vibration of the actuator, which in turn, can produce, for example, a haptic, tactile, and/or audible output. In some instances, the haptic, tactile, and/or audible output can provide to a user an indication associated with a position of a distal end portion of the catheter as the actuator moves the catheter from the first position toward the second position (as described in detail in the '894 application incorporated by reference above). In some embodiments, the introducer can include indicia or the like that can indicate to the user the relative position of the distal end portion of the catheter (e.g., relative to a distal end portion of the PIV).

As described above with reference to the transfer device 400, the actuator is configured to move the catheter to the second position such that the distal surface of the catheter is placed at the predetermined distance from the distal tip of the indwelling PIV. As described in detail above, the predetermined distance can be based at least in part on the venous anatomy of the vein in which the PIV and catheter are disposed. For example, in some instances, the predetermined distance is based at least in part on the existence and/or position of one or more valves within the vein and/or one or more branch vessels in fluid communication with the vein. In some instances, the method 50 can optionally include, for example, determining the venous anatomy associated with the vein prior to coupling the fluid transfer device to the indwelling peripheral intravenous line. This determining of the venous anatomy can be based on, for example, ultrasonic imaging, venogram, or fluoroscopy and/or the like. Thus, based on data associated with the venous anatomy, the distal surface of the catheter can be placed at the predetermined distance from the distal tip of the indwelling PIV. More particularly, the predetermined distance can be a position within the vein and/or relative to the PIV that is associated with a desired likelihood for successful aspiration of a volume of blood through the catheter.

As described in detail above, in some instances, the predetermined distance can be such that the distal surface of the catheter is disposed within the vein at a desired distance (e.g., a buffer zone) from a branch vessel in fluid communication with the vein. In some instances, the predetermined distance can be such that at least one of a valve or a branch vessel is in a position along the vein that is between the distal tip of the indwelling PIV and the distal surface of the catheter. That is to say, the distal tip of the PIV can be in a position relative to the vein that is distal to (e.g., upstream of) the valve and/or branch vessel and the distal surface of the catheter can be in a position relative to the vein that is proximal to (e.g., downstream of) the valve and/or branch vessel. As such, the distal surface of the catheter can be placed in a position within the vein that receives a desired volumetric flow rate of blood that is suitable for blood aspiration through the catheter and that would otherwise be reduced by obstructions within the vein (e.g., debris such as fibrin or the like) resulting from the indwelling portion of the PIV.

In some embodiments, the predetermined distance can be such that the distal surface of the catheter is in a distal position relative to the distal tip of the indwelling PIV. Similarly stated, the distal surface can be in a position along and/or relative to the vein that is proximal to a position along and/or relative to the vein of the distal tip of the indwelling PIV. Said yet another way, the distal surface of the catheter can be in a position within the vein that is downstream of a position within the vein of the distal tip of the indwelling PIV. As described in detail above, in some embodiments, the predetermined distance can be within a predetermined range of distances between, for example, about 0.0 mm and about 50.0 mm. For example, in some embodiments, the predetermined distance can be 30.0 mm. In some embodiments, the haptic, tactile, audible, and/or visual indication resulting from the movement of the actuator relative to the introducer can be associated with and/or otherwise indicate a distance between the distal surface of the catheter and the distal tip of the indwelling PIV. Thus, when a user determines the distal surface of the catheter is placed at the predetermined distance from the distal tip of the PIV, the user can stop moving the actuator relative to the introducer regardless of whether the actuator is in, for example, a distal most position relative to the introducer.

With the catheter in the second position and/or with the distal surface of the catheter being disposed at the predetermined distance from the distal tip of the PIV, a volume of blood is transferred via the catheter from the vein to a fluid reservoir in fluid communication with the catheter, at 53. The fluid reservoir can be any suitable fluid reservoir such as, for example, a negative pressure container or an evacuated container, a syringe, a sample bottle, and/or the like. In some instances, the method 50 can include establishing fluid communication between the catheter and the fluid reservoir. In other instances, the fluid communication between the catheter and the fluid reservoir can be pre-established (e.g., pre-assembled and/or assembled in a separate process or the like). Thus, with the distal surface of the catheter being disposed within the vein at a position in which a volumetric flow rate is not substantially restricted by obstructions otherwise resulting from the indwelling portion of the PIV catheter, a volume of blood can be transferred from the vein, through the catheter (and thus, the PIV), and into the fluid reservoir.

The method 50 includes moving the catheter from the second position toward the first position after a desired volume of blood is transferred to the fluid reservoir, at 54. In some instances, an actuator can be moved to move the catheter toward the first position and/or to place the catheter substantially in the first position. In other instances, the actuator can be moved to place the catheter in a third position (e.g., a storage or disposal position). The fluid transfer device is decoupled from the indwelling PIV after the catheter is moved from the second position toward the first position, at 55. Moreover, the fluid reservoir can be removed from fluid communication with the catheter (e.g., decoupled or the like) prior to the catheter being moved toward the first position, after the catheter is moved toward the first position, or after the fluid transfer device is decoupled from the indwelling PIV. With the fluid transfer device decoupled from the indwelling PIV, the fluid transfer device can be safely discarded. In this manner, the fluid transfer device can be used to aspirate a volume of blood from a vein that is accessed via an indwelling peripheral intravenous catheter.

While the distal surface of the catheter is described above as being disposed at the predetermined distance from the distal tip of the PIV when the distal surface of the catheter is in a distal most position relative thereto, in other embodiments, the predetermined distance can be a distance between the distal surface of the catheter and the distal tip of the PIV when the distal surface of the catheter is in a proximal position relative to the distal tip of the PIV. For example, in some instances in which the vein is in fluid communication with a branch vessel that is beyond a reach of the catheter (e.g., downstream of the catheter when the catheter is fully advanced relative to the introducer), it may be desirable to advance the catheter to the second position in which the distal surface of the catheter is disposed within the PIV catheter. More particularly, in some such instances, the distal surface of the catheter can be disposed at the predetermined distance from the distal tip of the PIV when the distal surface of the catheter is distal to, for example, a hub of the PIV but proximal to, for example, the distal tip of the PIV. As such, the catheter can be in the second position when the distal surface of the catheter is in a distal position relative to one or more kinks otherwise formed in the PIV catheter. In other instances, the catheter can be in the second position when the distal surface of the catheter is substantially flush with the distal tip of the PIV (e.g., the predetermined distance is about 0.0 mm). Thus, in some instances, the predetermined distance between the distal tip of the PIV and the distal end or surface of the catheter can be, for example, a predetermined range of distances that includes a distance in a proximal direction (e.g., a negative distance) and a distance in a distal direction (e.g., a positive distance), as described in the '834 application incorporated by reference above. Moreover, by passing the catheter through at least a portion of the PIV, the catheter can be configured to "unkink" at least a portion of the PIV whether the distal surface of the catheter is in a proximal position relative to the distal tip of the PIV or a distal position relative to the distal tip of the PIV. In other instances, advancing the catheter to a position such that the distal end of the catheter is distal to the distal tip of the PIV can, for example, remove debris such as fibrin, clots, etc. from the distal tip of the PIV, which in turn, may be sufficient to allow for successful blood draw through the catheter.

The embodiments described herein can be used to transfer fluid from a patient or to the patient by accessing a vein via an indwelling PIV. In some instances, the embodiments described herein can be used to aspirate a volume of blood efficiently while maintaining the integrity of the sample. While extracting blood, the transfer device 300 and/or 400, for example, can be configured to receive and/or produce a substantially laminar (e.g., non-turbulent or low turbulent) flow of blood through the transfer device 300 and/or 400, respectively, to reduce and/or substantially prevent hemolysis of the blood as the blood flows through the transfer device 300 and/or 400, respectively.

As described above, the transfer device 300 and/or 400, for example, can be manipulated to place the distal surface of the catheter 360 and/or 460, respectively, at a predetermined and/or desired distance from a distal surface of the PIV. In some instances, for example, the predetermined and/or desired distance can be based at least in part on the venous anatomy (e.g., the existence of one or more valves and/or branch vessels), as described in detail above with reference to the vascular structure analysis. Specifically, in some instances, the predetermined and/or desired distance can be about 5.0 mm, about 10.0 mm, about 15.0 mm, about 20.0 mm, about 25.0 mm, about 30.0 mm, about 35.0 mm, about 40.0 mm, about 45.0 mm, about 50.0 mm, and/or any suitable distance or fraction of a distance therebetween. In other instances, a predetermined and/or desired distance can be zero. That is to say, in some instances, it may be desirable to position the distal surface of the catheter 260 substantially flush to and/or with the distal tip of the PIV catheter. Moreover, in some instances, the predetermined and/or desired distance can be proximal to the distal tip of the PIV catheter (e.g., the distal end of the blood draw catheter is disposed within the PIV catheter) or the predetermined and/or desired distance can be distal to the distal tip of the PIV catheter (e.g., the distal end of the blood draw catheter is disposed outside of the PIV catheter and within, for example, a vein). As described above, it should be understood that when referring to a predetermined and/or desired distance, such a distance can be, for example, within a predetermined and/or desired range of distances. In some instances, the predetermined and/or desired range of distances can be based at least in part on the venous anatomy and/or one or more characteristics associated with an indwelling PIV such as, for example, a PIV length.

Although the predetermined and/or desired distance is described above as being a positive distance, that is, the distal surface of the catheter 360 and/or 460 is flush with or distal to the distal tip of the PIV catheter, in other embodiments, a predetermined and/or desired distance can be associated with a distal surface of a catheter (e.g., the catheter 360 of the transfer device 300 or the catheter 460 of the transfer device 400) being in a proximal position relative to the distal tip of the PIV catheter (e.g., a negative distance). For example, in some instances, the predetermined and/or desired distance can be between about 0.0 mm (e.g., the distal surfaces are flush) to about −50 mm, between about −10 mm and about −40 mm, between about −20 mm and about −30 mm, or between any other suitable range or subranges therebetween. In some instances, the predetermined and/or desired distance can be less than −50 mm (e.g., the distal surface of the catheter 360 and/or 460 is more than 50 mm proximal to the distal surface of the PIV). In some instances, the catheter 360 and/or 460, for example, can be placed in the second position such that a distal end portion of the catheter 360 and/or 460 remains within the PIV in a position distal to, for example, a kink or the like. For example, an indwelling PIV can have one or more portions that are kinked and/or bent (e.g., a portion of the PIV where the PIV catheter couples to a hub). In such instances, the predetermined and/or desired distance can be such that the distal surface of the catheter 360 and/or 460 is distal to the portion of the PIV that forms the kink while remaining within the PIV, which in turn, can result in a fluid flow path being sufficiently unrestricted to allow blood aspiration therethrough, as described in the '834 application incorporated by reference herein.

Although not shown in FIGS. 8-11 and/or 12-14, the transfer device 300 and/or 400, respectively, can be coupled to any suitable PIV while still being configured to place the distal surface of the catheter 360 and/or 460, respectively, at the predetermined and/or desired distance relative to the distal tip of the PIV catheter. In some instances, use of a PIV can include coupling the PIV to an IV extension set and/or an adapter (e.g., a single port adapter, a Y-adapter, a T-adapter, or the like). Thus, while the transfer devices 300 and/or 400 are described herein as being coupled to a PIV, it should be understood that the transfer devices 300 and/or 400 can be coupled to either a PIV or an adapter coupled thereto based on the situation and/or configuration. The transfer devices 300 and/or 400 can be configured to couple to any suitable commercially available PIV, adapter, and/or extension set. For example, the lock 450 of the transfer device 400 can have a size, shape, and/or configuration that can allow the lock 450 to be coupled to various PIVs, adapters, and/or extension sets, as described in detail in the '834 application incorporated by reference above. Moreover, the catheter 460 can have a length that is sufficient to place the distal surface of the catheter 460 at a desired position relative to the distal tip of the PIV when the catheter 460 is in the second position regardless of the lock 450 coupling to an adapter (e.g., IV extension set) or directly to the PIV.

The embodiments described herein can be used in a variety of settings (ER, in-patient, etc.). The following scenario of withdrawing a sample volume of blood from a patient is provided by way of example. In some instances, a peripheral intravenous (PIV) line and/or catheter is inserted into a vein of a patient following standard guidelines and an extension set and/or adapter is attached. The PIV catheter can remain within the vein for an extended period and can provide access to the vein for the transfer of fluids (e.g., saline, blood, drug compounds, etc.) to the patient. That is to say, after placement, the PIV is an indwelling PIV catheter. When it is time to draw a volume blood, a user (e.g., nurse, physician, phlebotomist, and/or the like) can stop the transfer of fluid to the patient, if it is transferring fluid, for approximately 1-5 minutes to allow the fluid to disperse from the PIV insertion site. To draw the blood sample, the user attaches a transfer device (e.g., the transfer device 400) to a port and/or suitable portion of the extension set and/or adapter and transitions the transfer device from a first configuration (e.g., a storage configuration as shown in FIGS. 12 and 13) to a second configuration, in which a portion of a catheter included in the transfer device extends through the peripheral IV and into the vein (e.g., as shown in FIG. 14).

As described in detail above with reference to the transfer device 400, a distal surface of the catheter can be disposed at a predetermined and/or desired distance from a distal tip of the PIV catheter when the transfer device is in the second configuration to place the catheter in fluid communication with a portion of the vein that receives an unobstructed and/or uninhibited flow of blood. For example, the distal surface of the catheter can be in a distal position relative to the distal tip of the PIV catheter and at least one branch vessel, valve, and/or the like in fluid communication with the vein. Once the catheter is in the desired position, the user can attach one or more negative pressure collection containers, tubes, and/or syringes to the transfer device to extract a volume of blood. In some instances, the volume of blood can be a first volume of blood that can be discarded and/or at least temporarily stored apart from a subsequent sample volume of blood (e.g., typically a volume of about 1-3 milliliters (mL) but up to 8-10 mL of blood can be a "waste" or "pre-sample" volume). In some instance, the waste volume can include contaminants, non-dispersed residual fluids, and/or the like. After the collection of the waste volume, the user can couple, for example, one or more negative pressure containers (e.g., sample containers) to the transfer device to collect a desired blood sample volume. Once the sample volume is collected, the transfer device can be transitioned from the second configuration toward the first configuration and/or a third configuration (e.g., a "used" configuration). The transfer device can then be decoupled from the extension set and/or adapter and safely discarded. In some instances, after collecting the sample volume but prior to transitioning the transfer device from the second configuration, the waste or pre-sample volume, for example, can be reinfused into the vein via the transfer device.

While various embodiments are described above, it should be understood that they have been presented by way of example only, and not limitation. Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments as discussed above.

Figure 30:
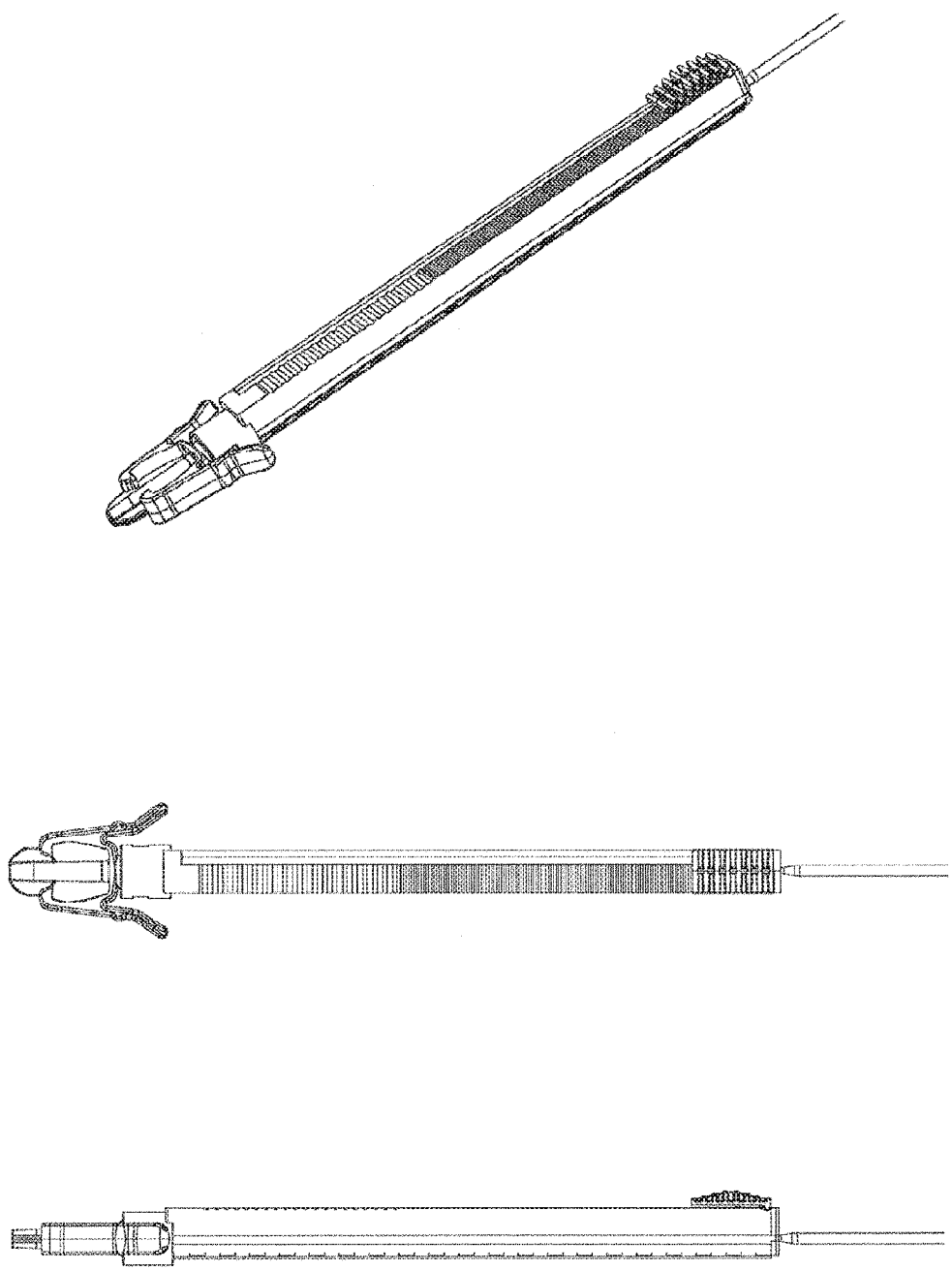
FIGS. 30-43 illustrate various aesthetic and/or industrial designs of a fluid transfer device each according to a different embodiment.
Figure 31:
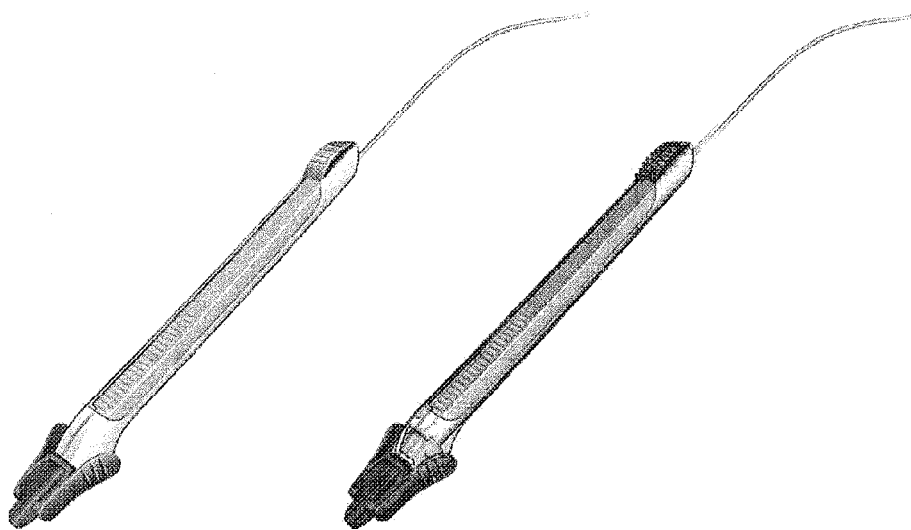
Figure 32:
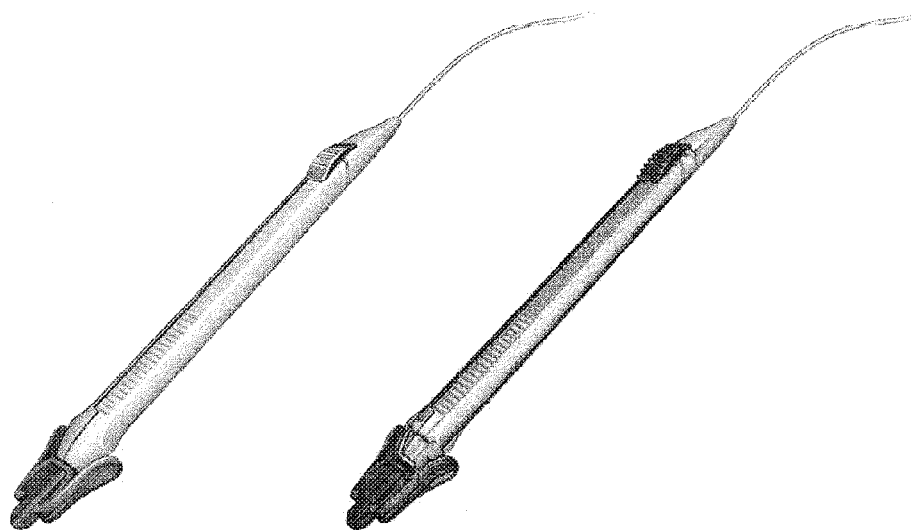
Figure 33:
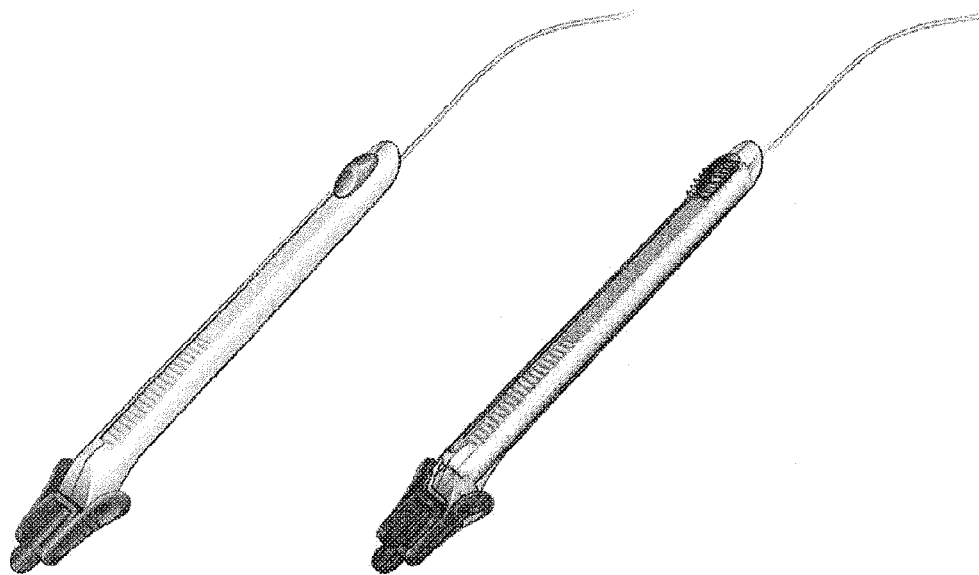
Figure 34:
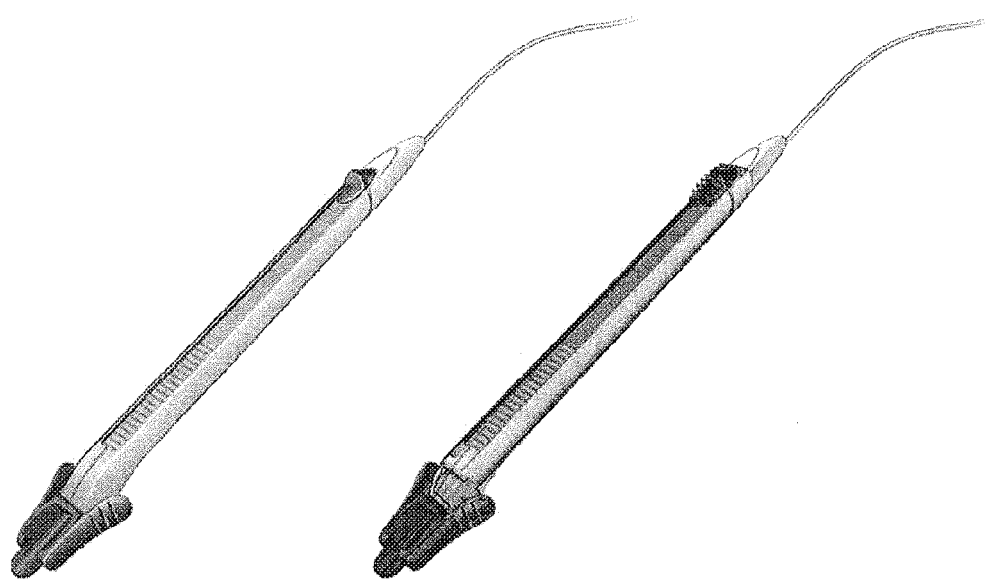
Figure 35:
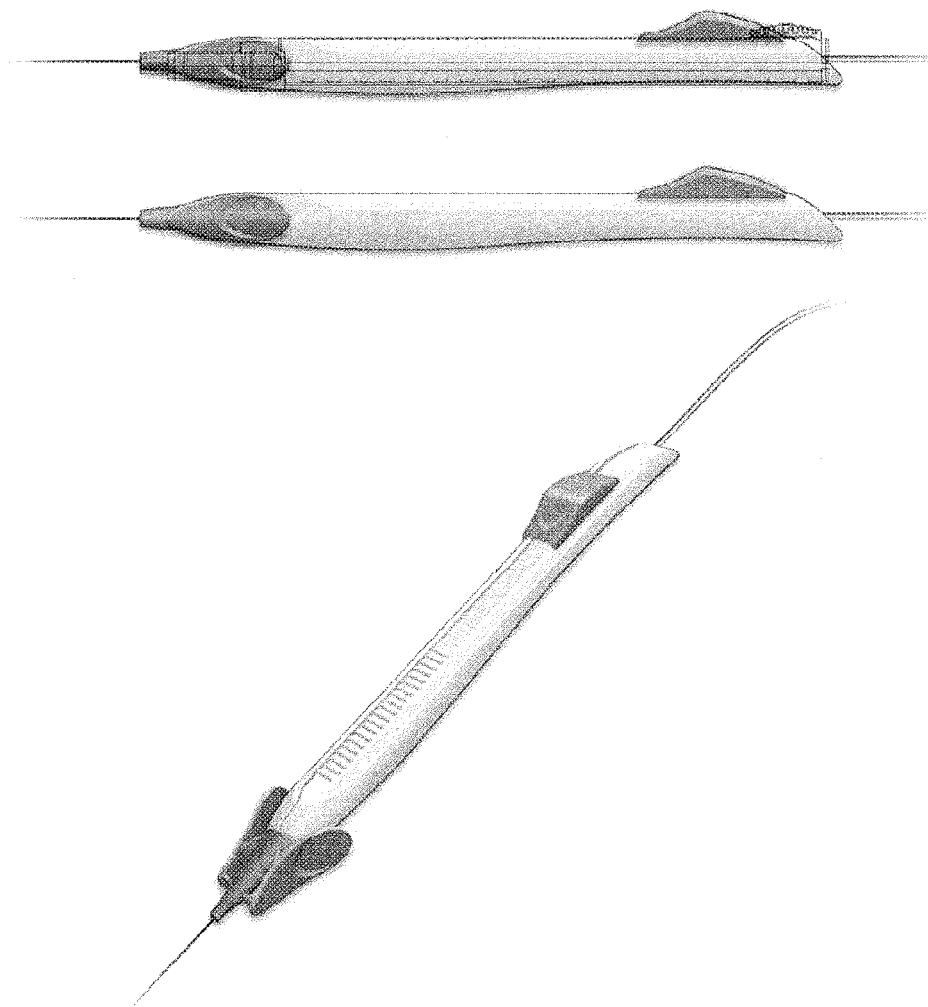
Figure 36:
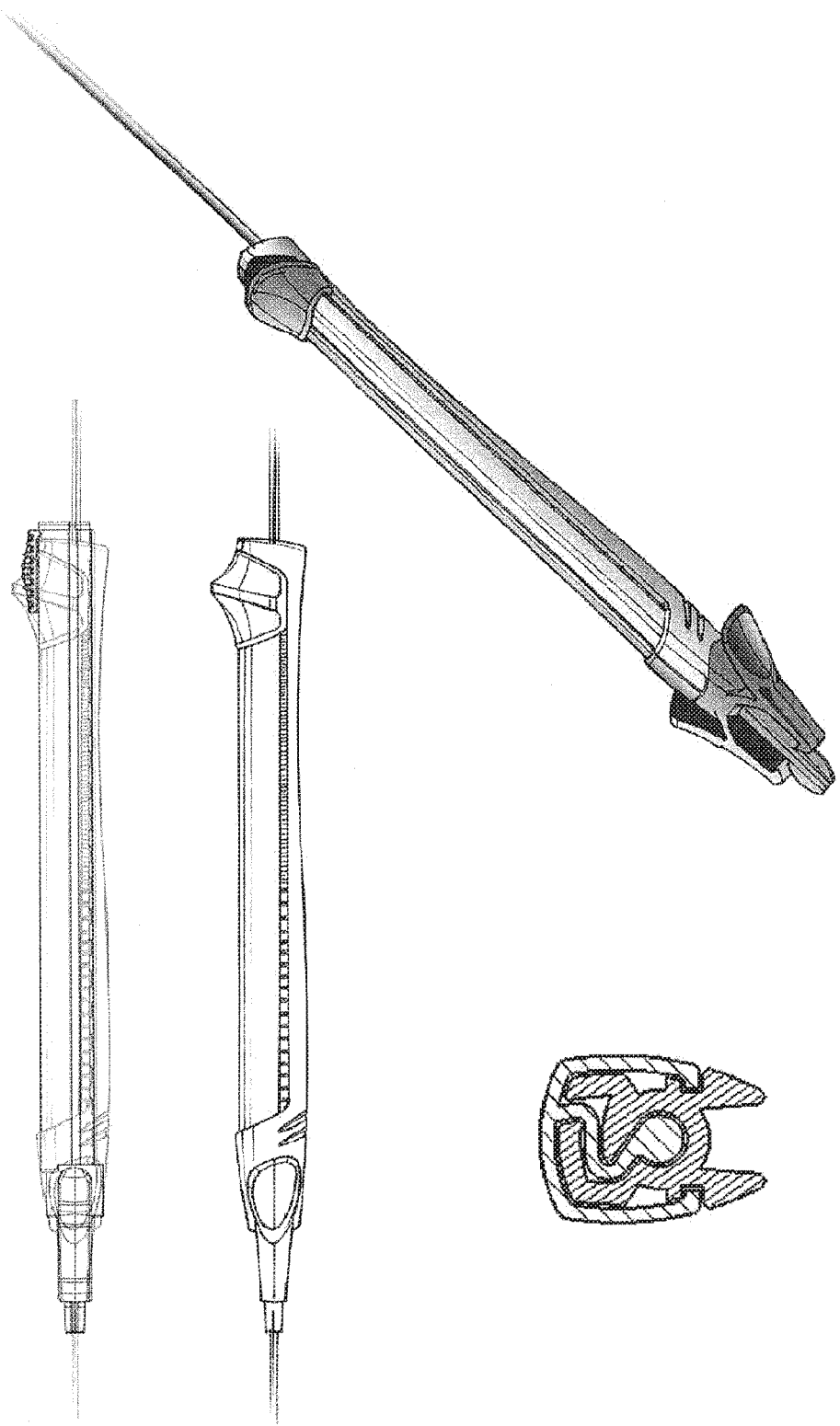
Figure 37:
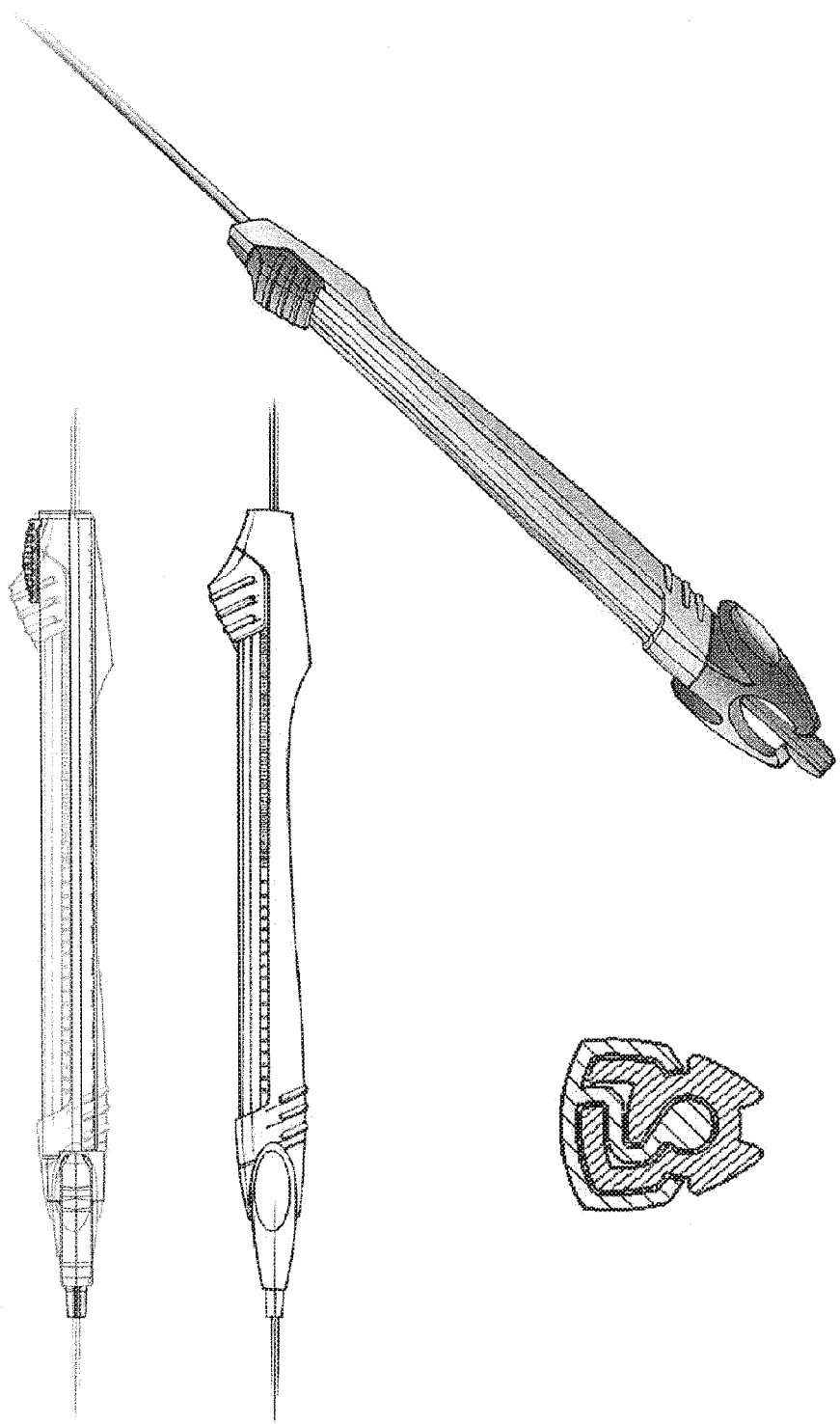
Figure 38:
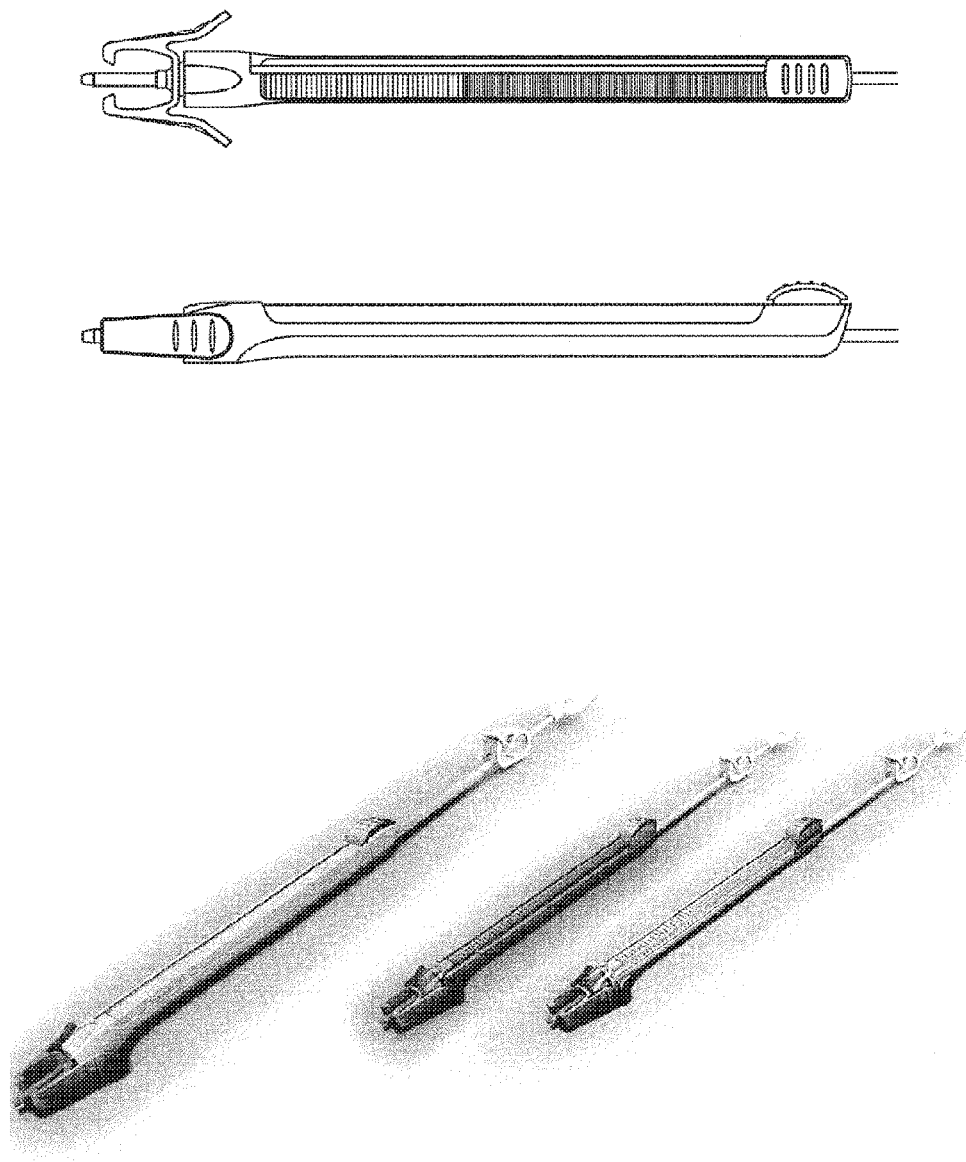
Figure 39:
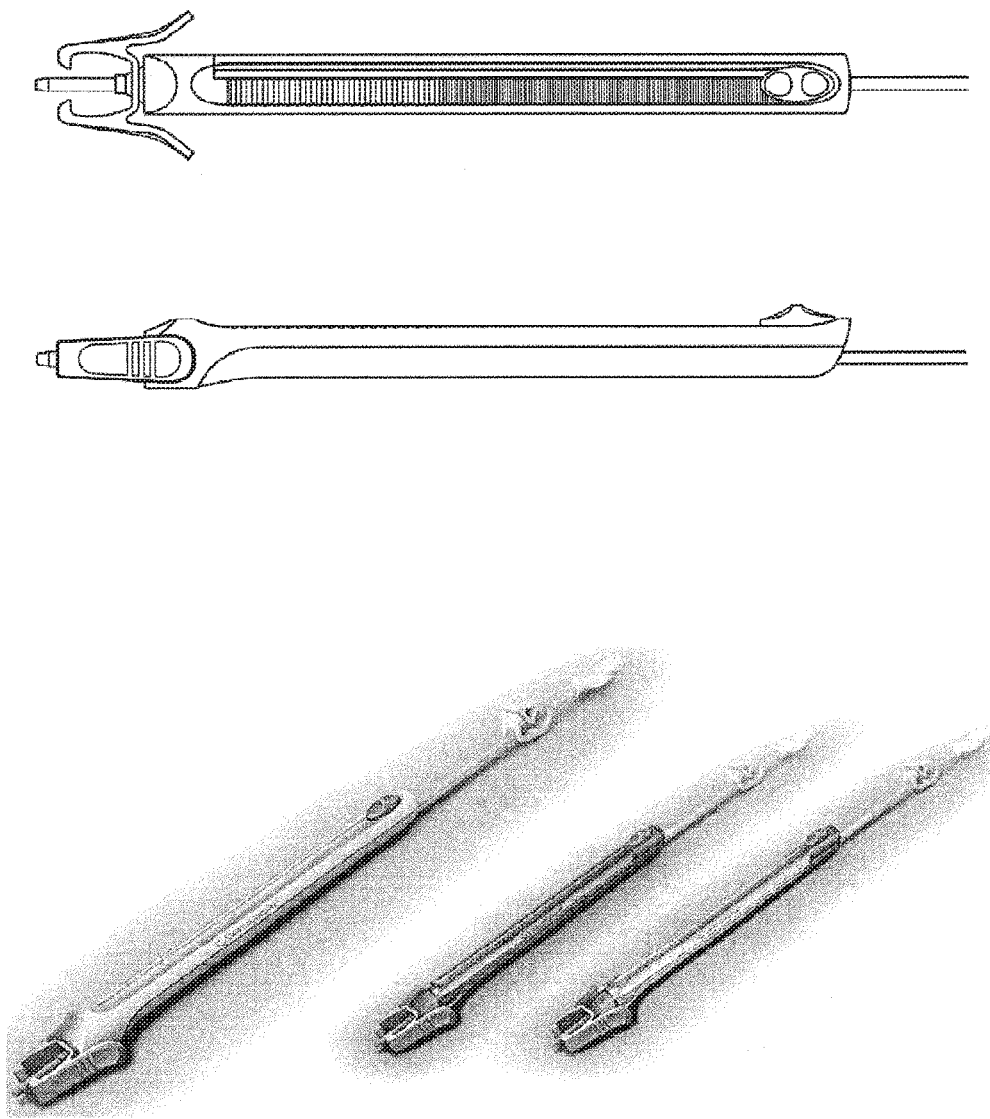
Figure 40:
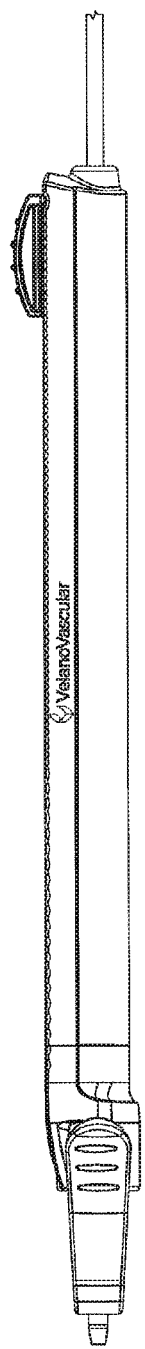
Figure 41:
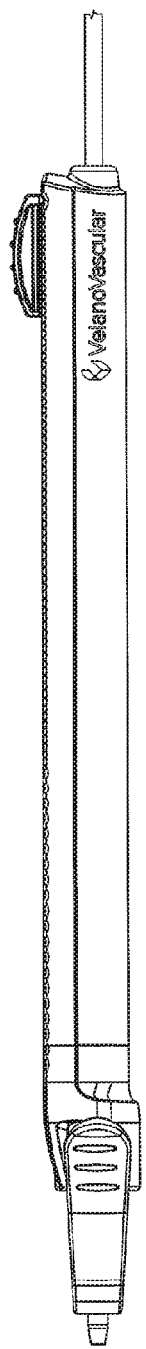
Figure 42:
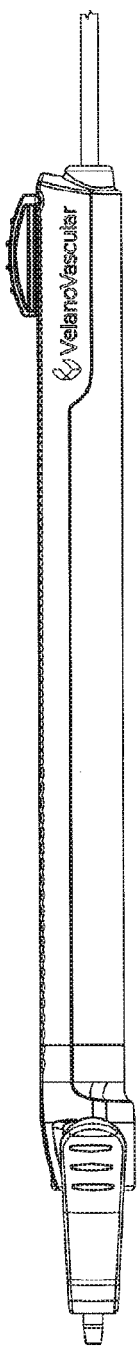
Figure 43:
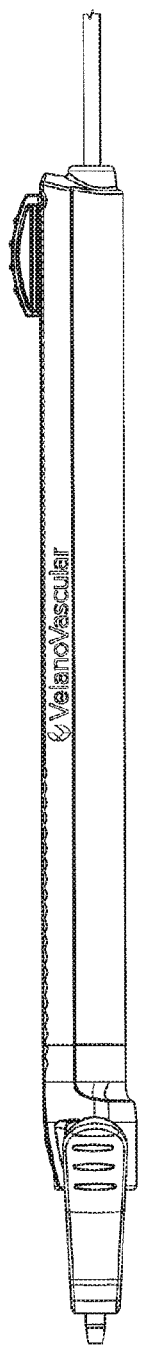
Figure 44:
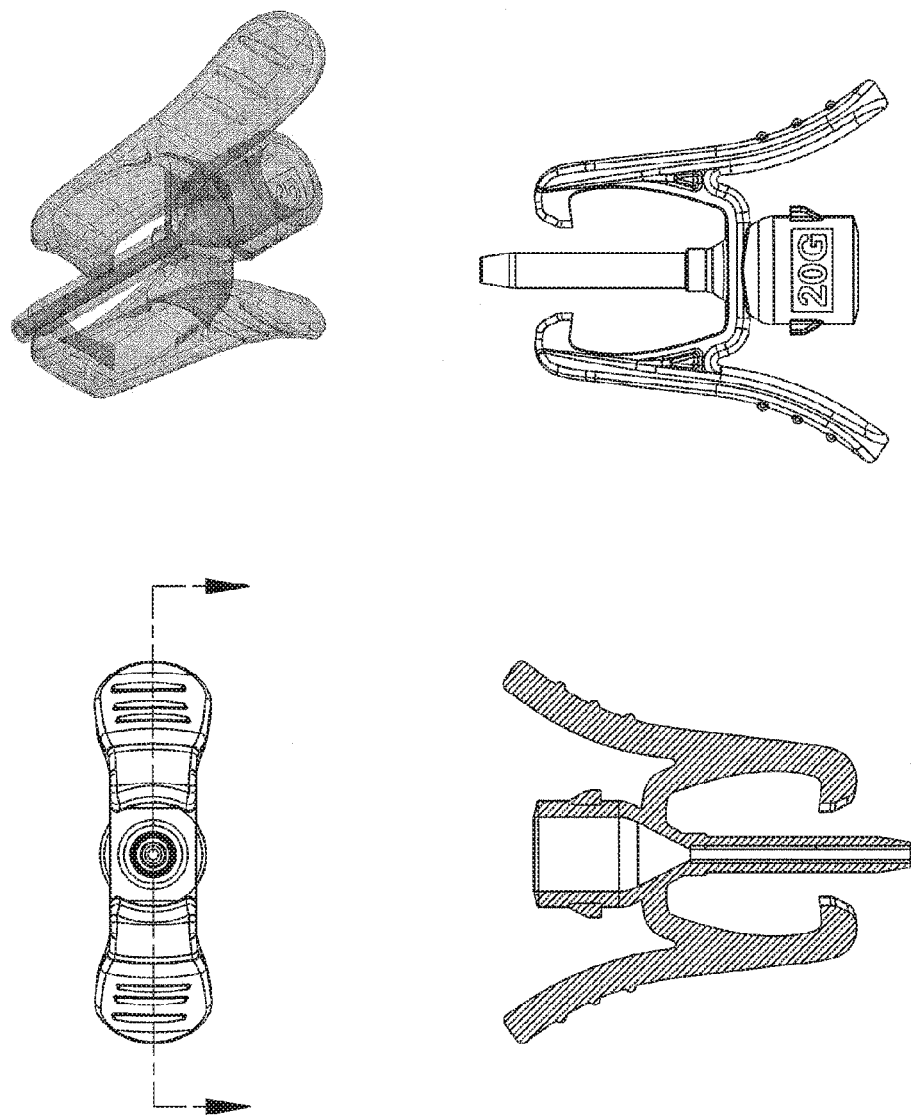
FIGS. 44 and 45 are various views of a locking mechanism configured for use with a fluid transfer device each according to a different embodiment.
Figure 45:
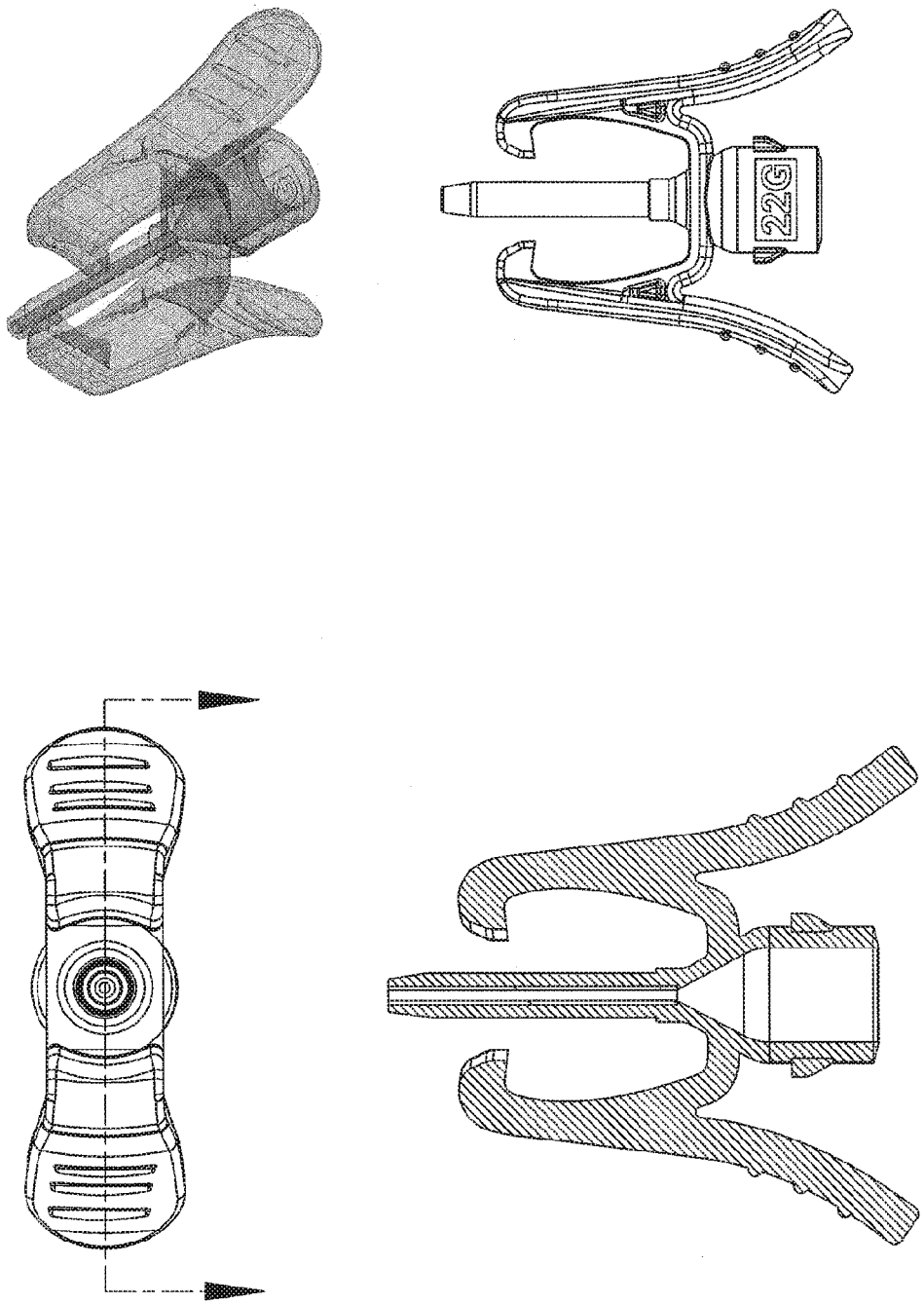
Figure 46:
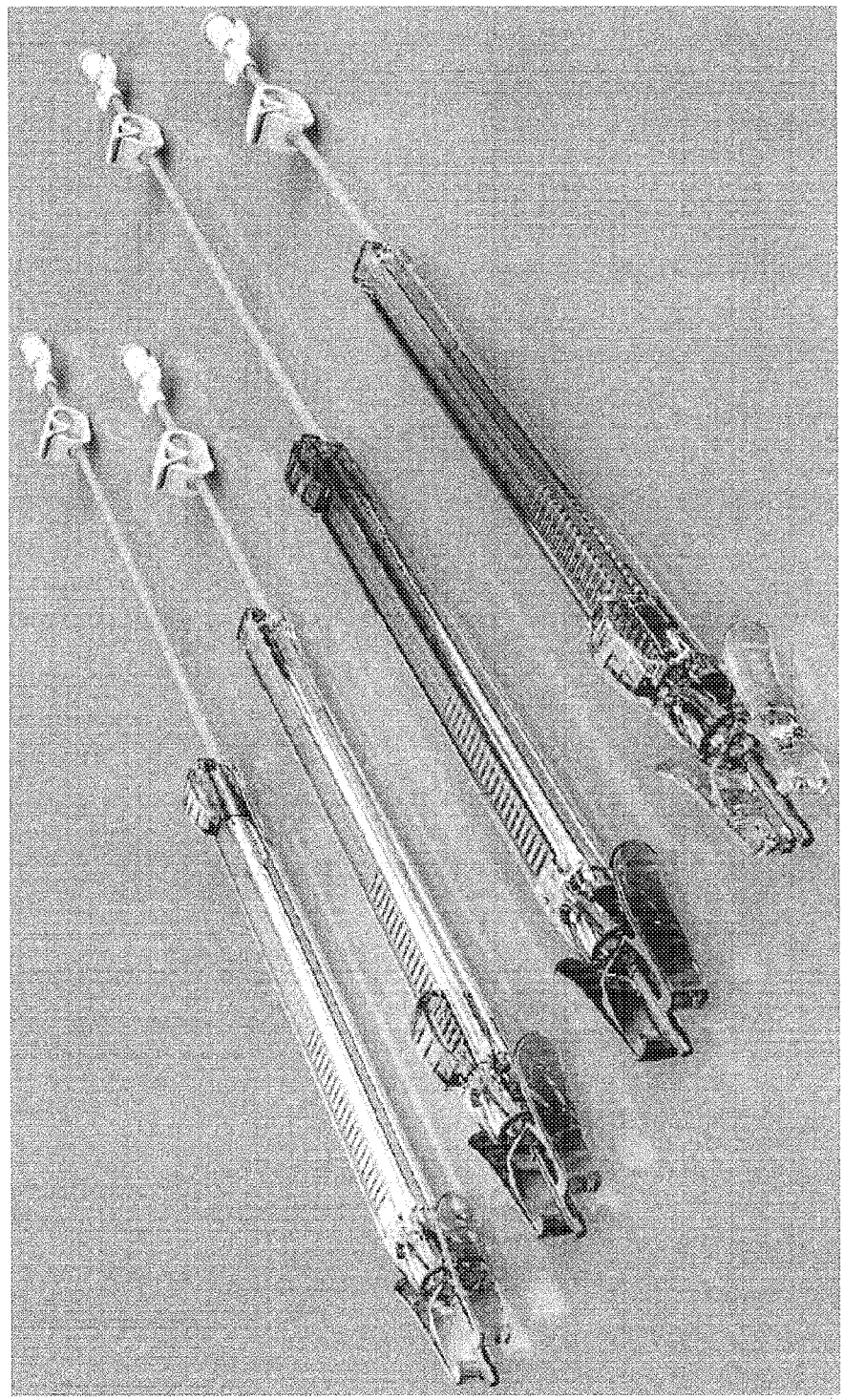
FIGS. 46-61 illustrate various fluid transfer devices each with a different color and/or labeling scheme according to particular embodiments.
Figure 47:
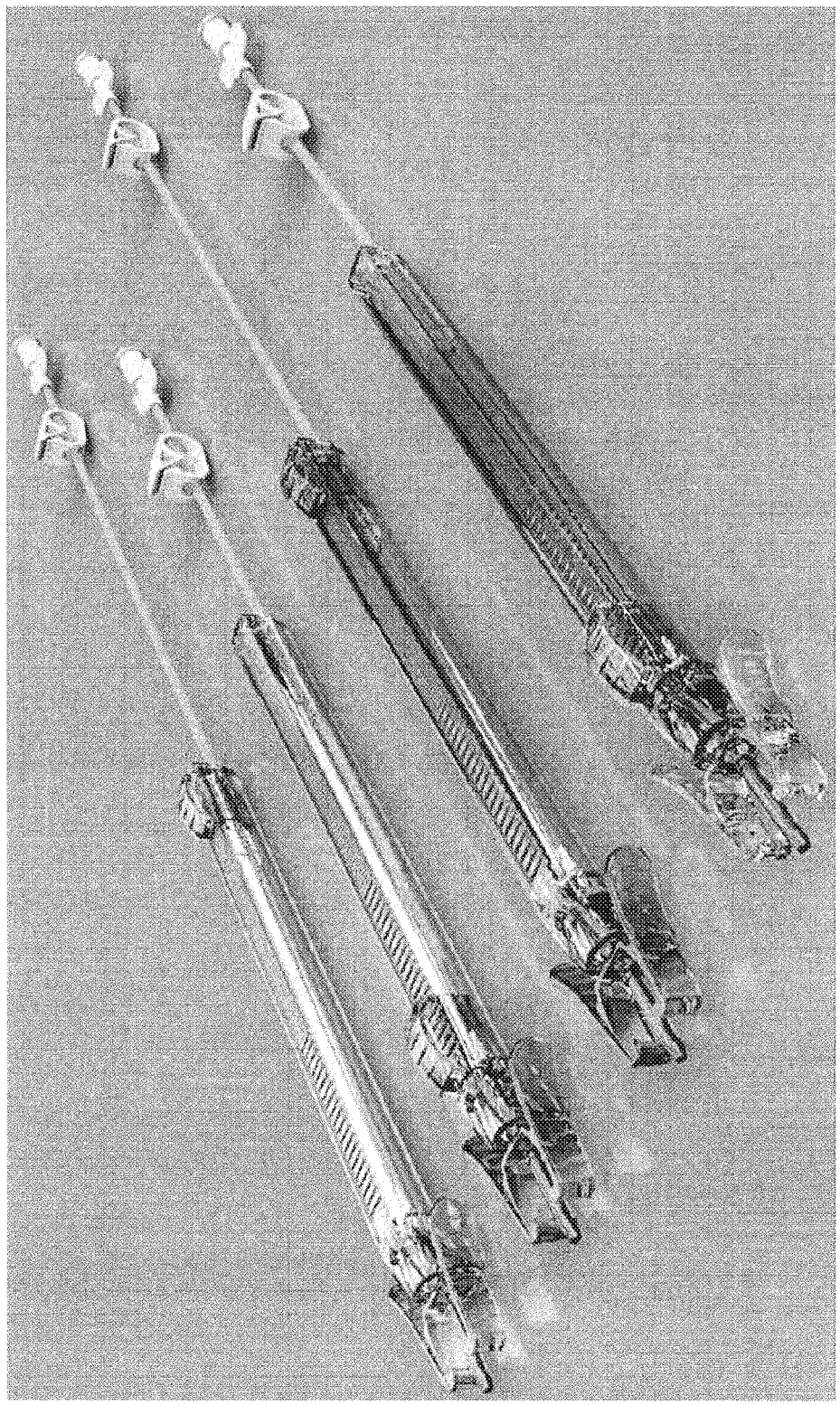
Figure 48:
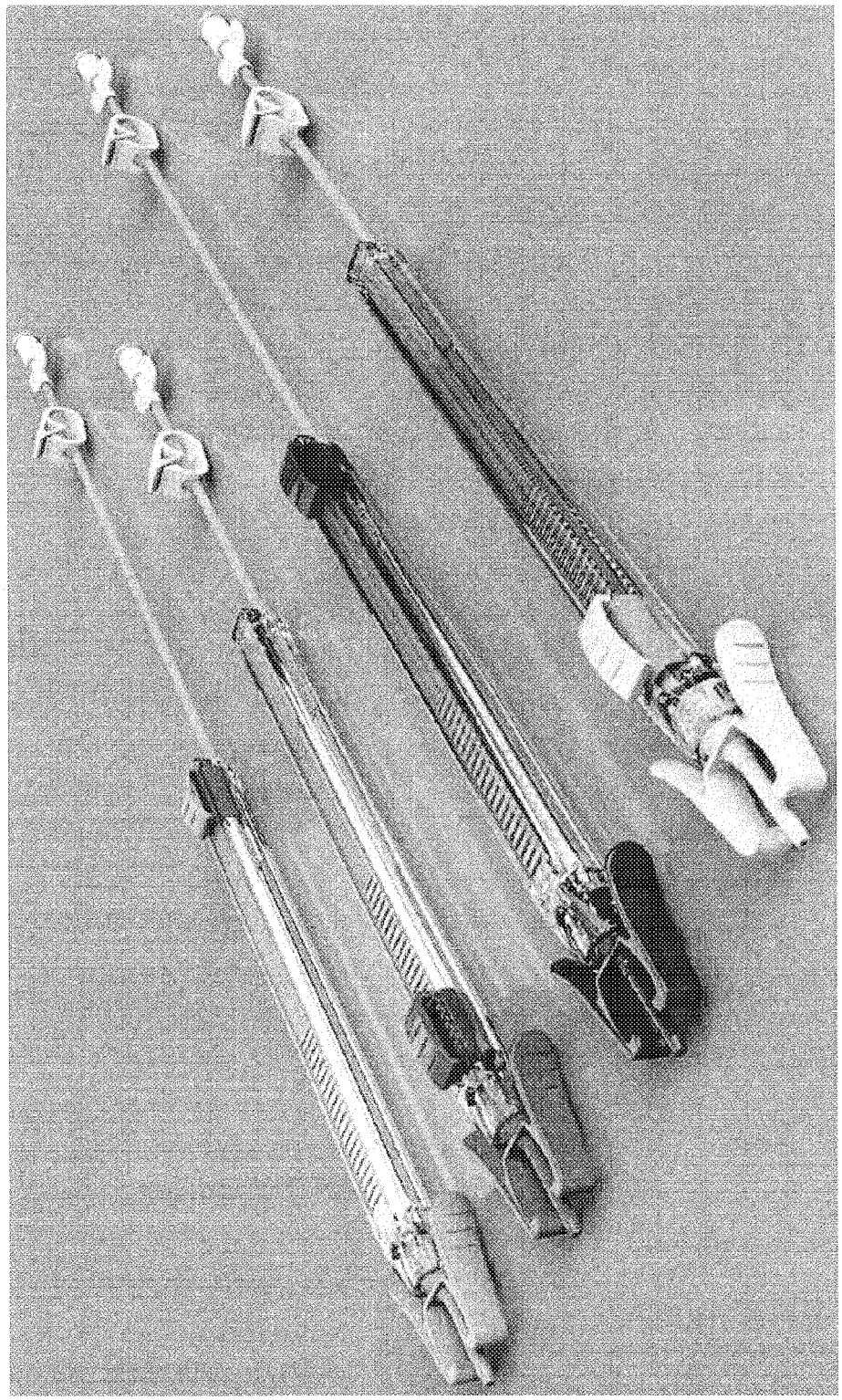
Figure 49:
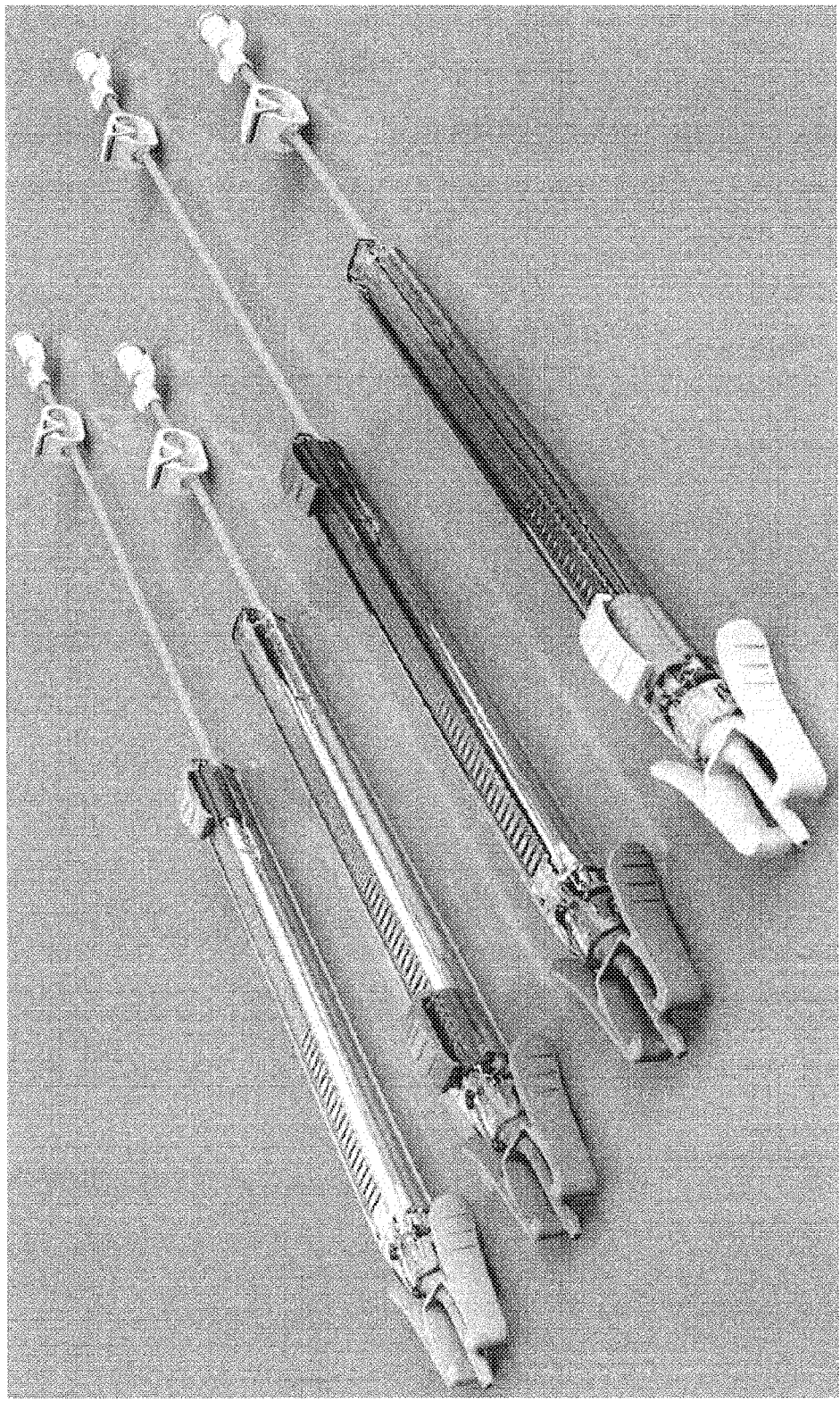
Figure 61:
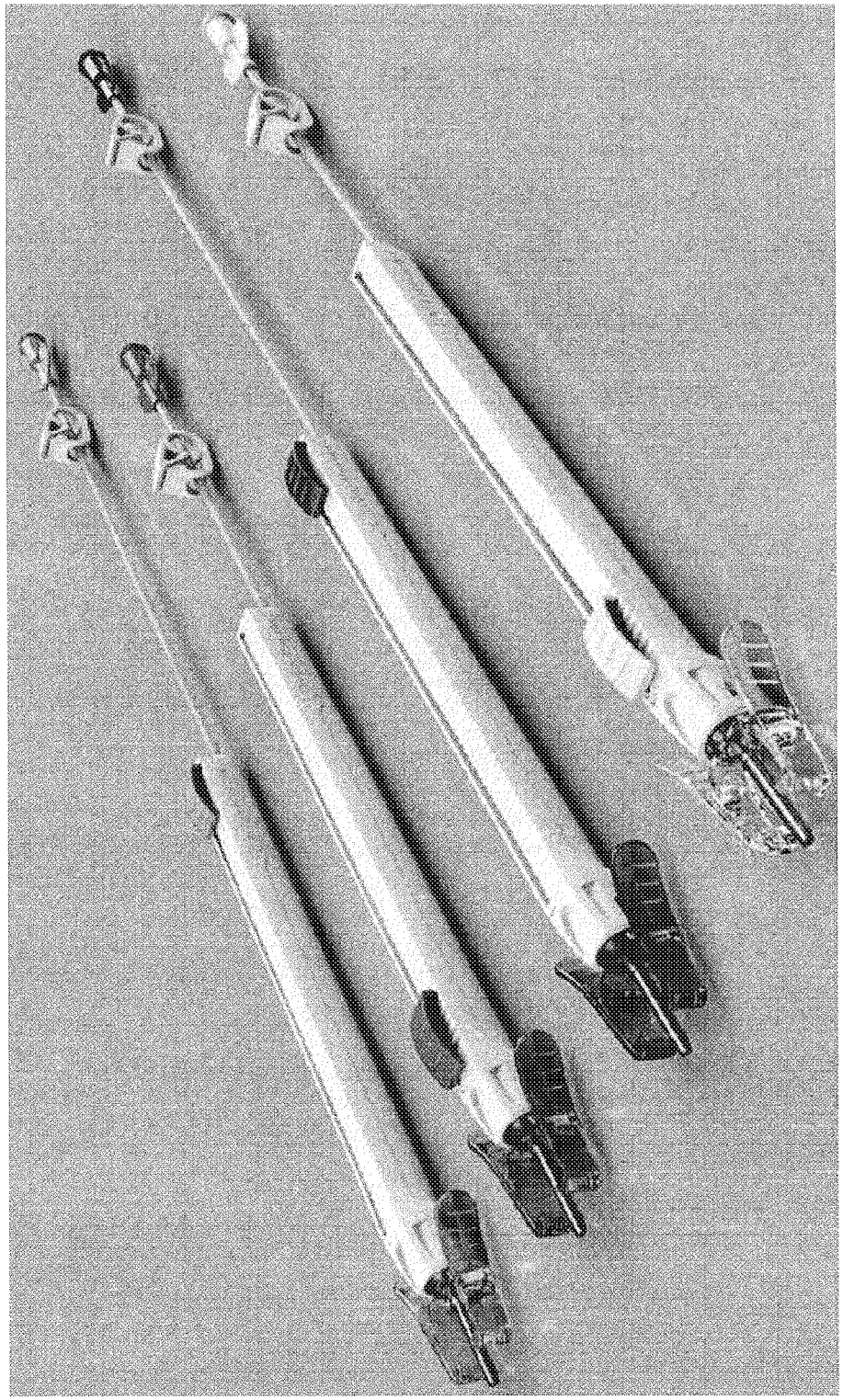

For example, FIGS. 30-61 illustrate various transfer device configurations, each according to an embodiment. Each of the embodiments shown in FIGS. 30 and 61 can be substantially similar in form and/or function to, for example, the transfer device 400 described above with reference to FIGS. 12-14. As shown, for example, in FIGS. 30-39 a transfer device that is substantially similar in at least function to the transfer device 400 can have any suitable configuration and/or arrangement that can enhance and/or increase an aesthetic appeal and/or the ergonomics of the transfer device. In some embodiments, a transfer device that is substantially similar in at least function to the transfer device 400 can have a design configured to display indicia such as instructions for use, company name, size and/or compatibility (e.g., "20-gauge," "22-gauge," and/or the like, as shown in FIGS. 40-43. Similarly, as shown in FIGS. 44 and 45, a lock mechanism, coupler, clip, and/or any other suitable portion can be configured to display indicia and/or otherwise provide an indication to a user of, for example, an intended use of the transfer device.

In some embodiments, any portion of the transfer devices (e.g., including transfer devices 300 and 400 described above) can have a color or the like configured to provide an indication of the intended use of the transfer device. In some embodiments, the color of at least a portion of any transfer device described herein can be according to an industry standard, a U.S. Food and Drug Administration (FDA) rule or standard, and/or the like. For example, in some embodiments, any suitable portion of the transfer devices described herein can be shaded and/or colored yellow, indicating a 24-gauge catheter is included therein; blue, indicating a 22-gauge catheter is included therein; pink, illustrating a 20-gauge catheter is included therein; green, illustrating a 18-gauge catheter is included therein; and/or any other suitable color coding.

Figure 50:
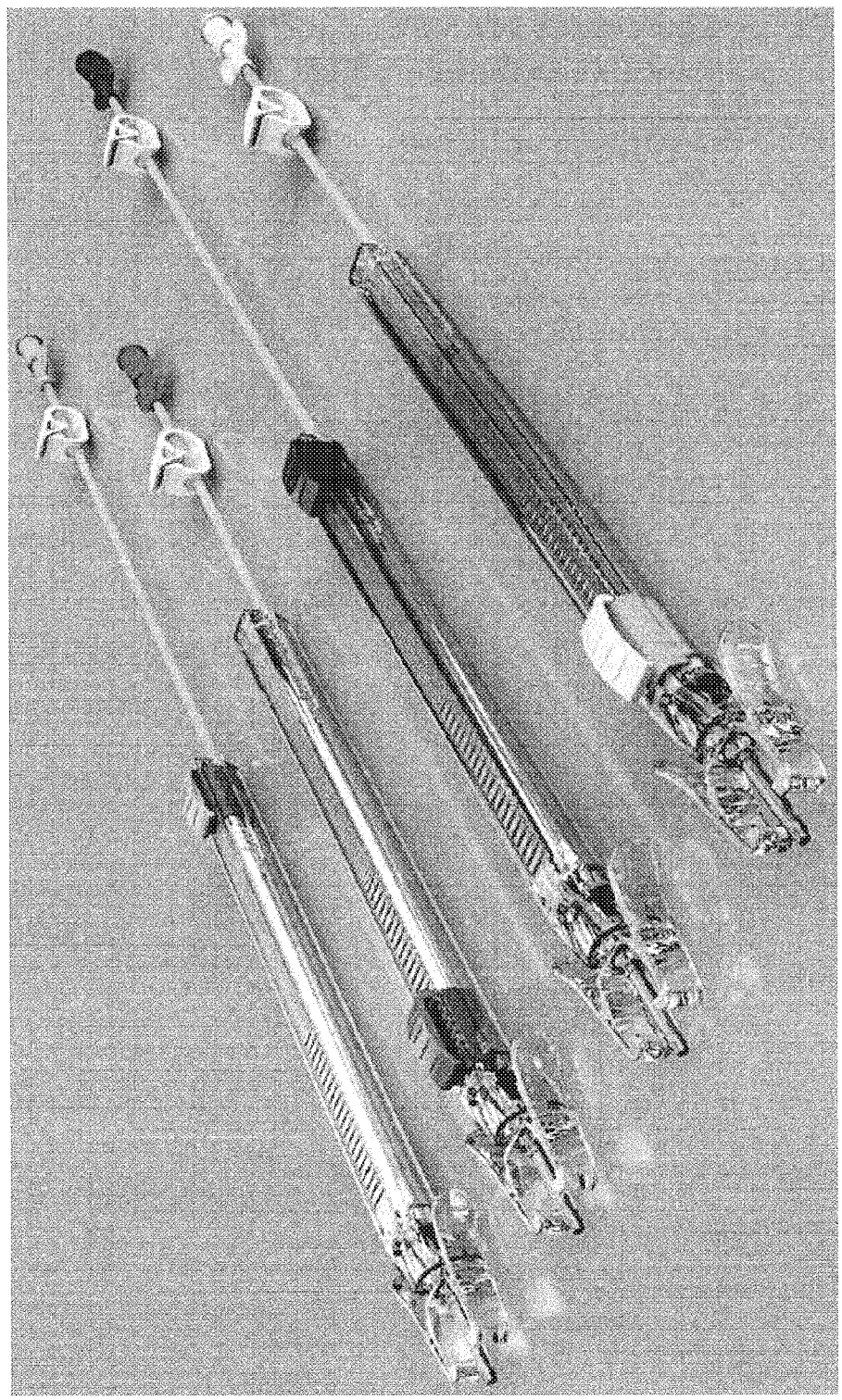
Figure 51:
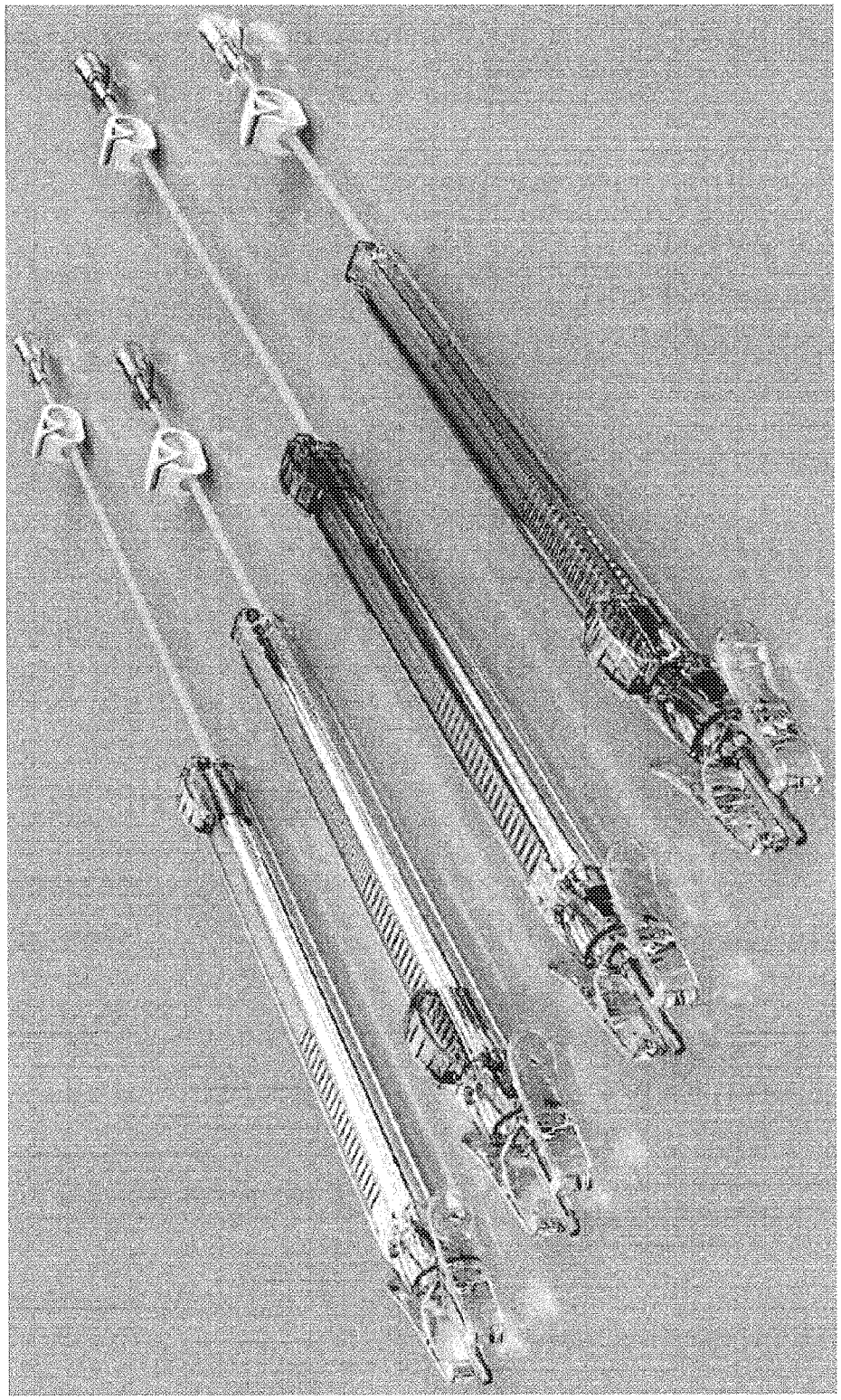
Figure 52:
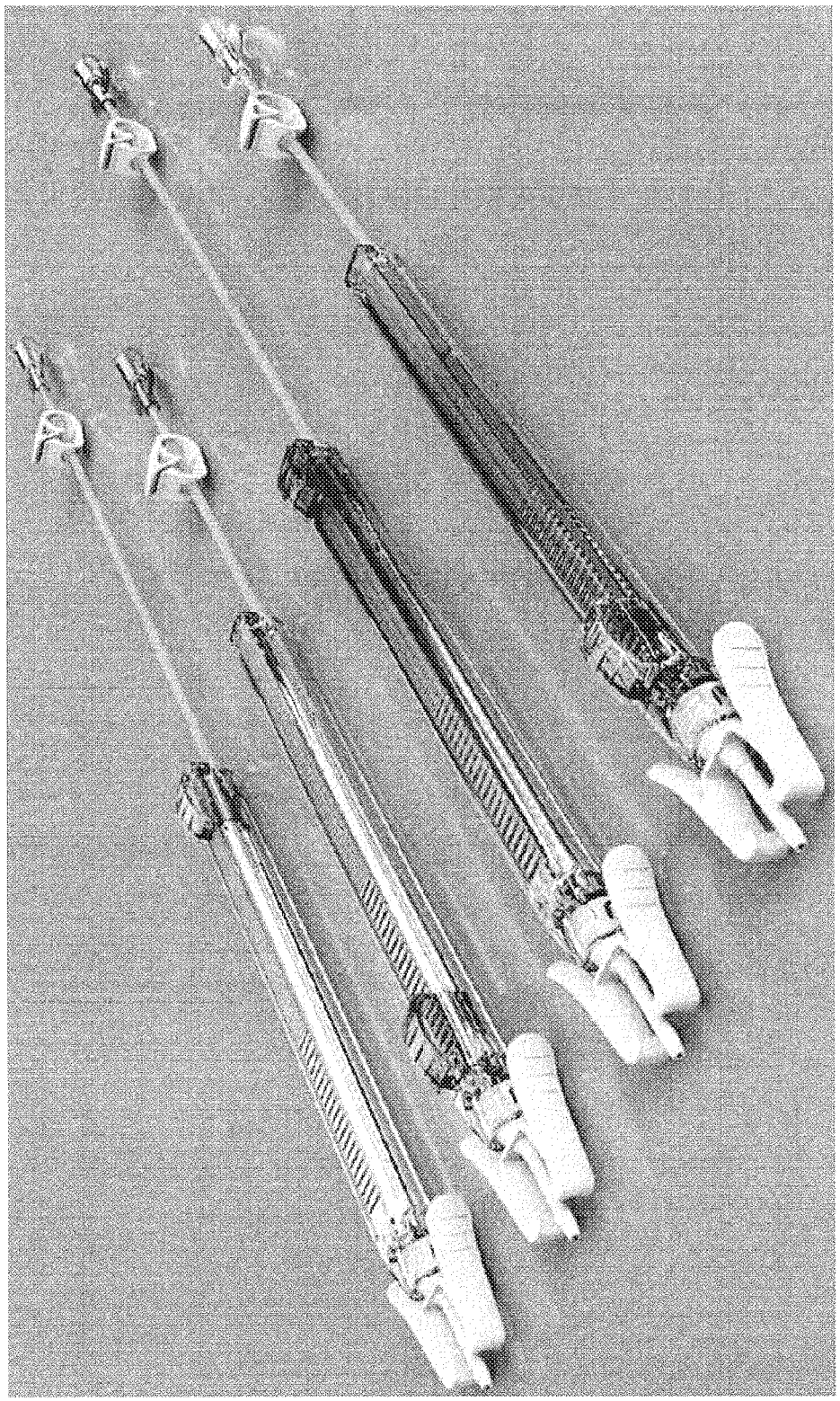
Figure 53:
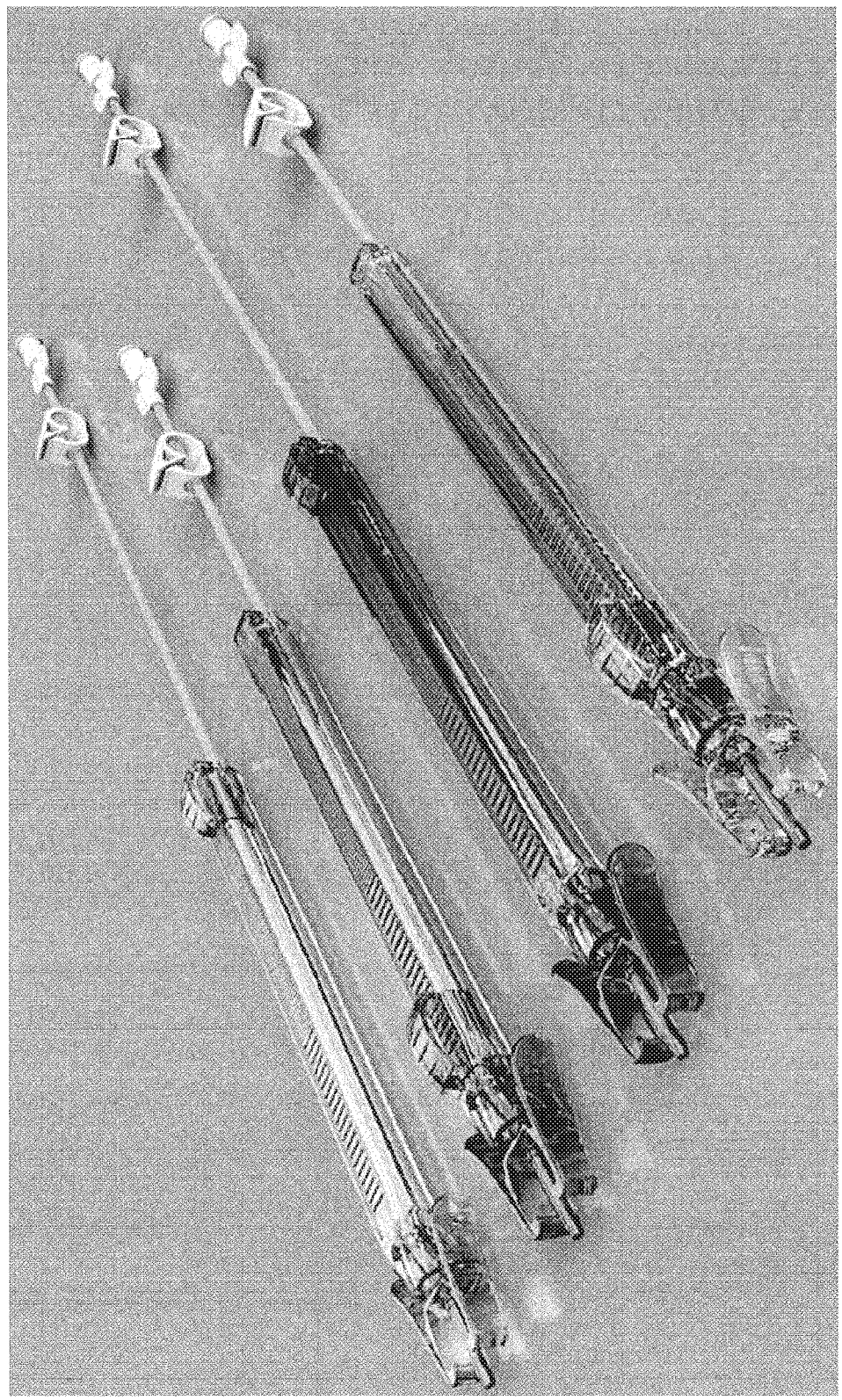
Figure 54:
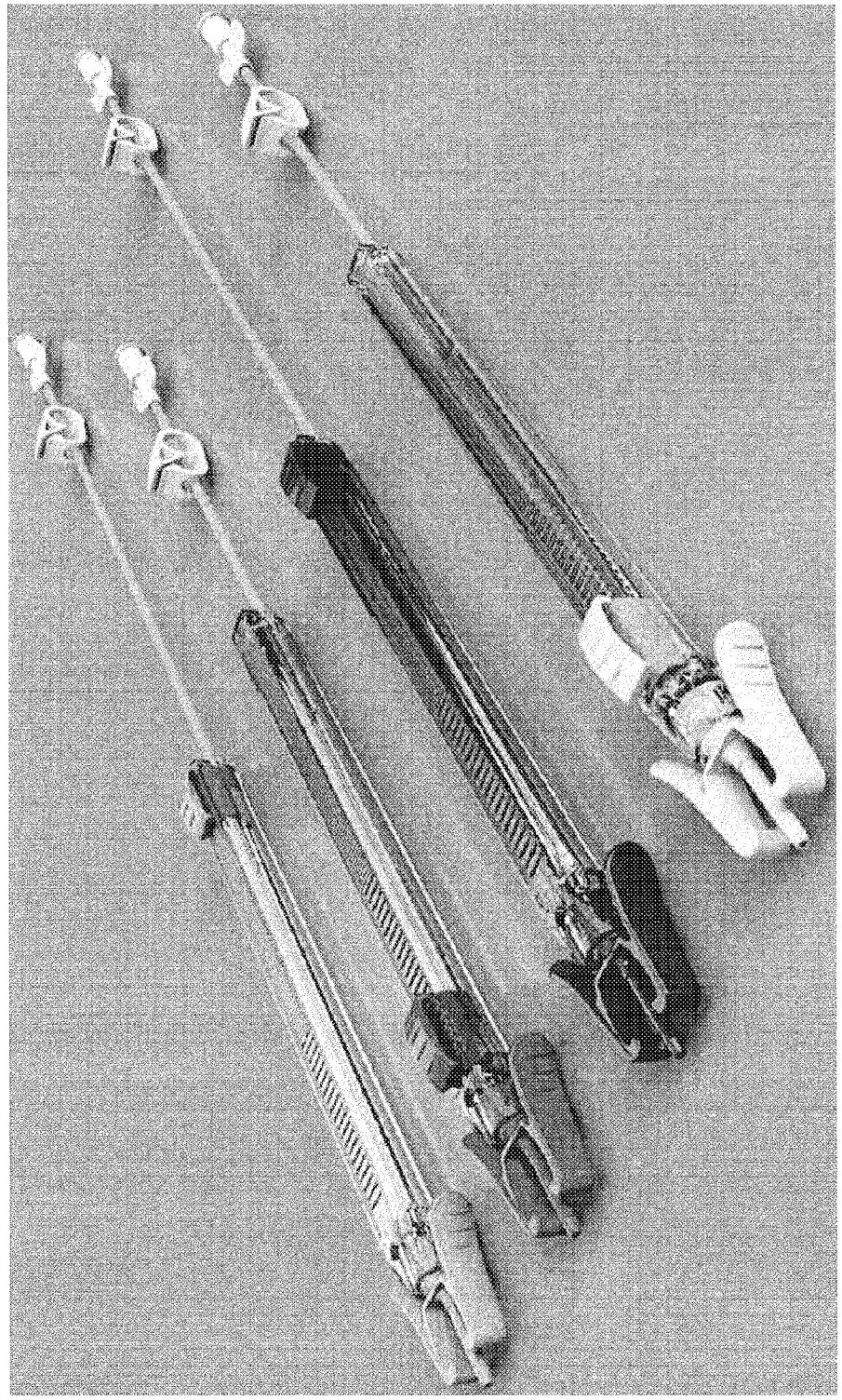
Figure 55:
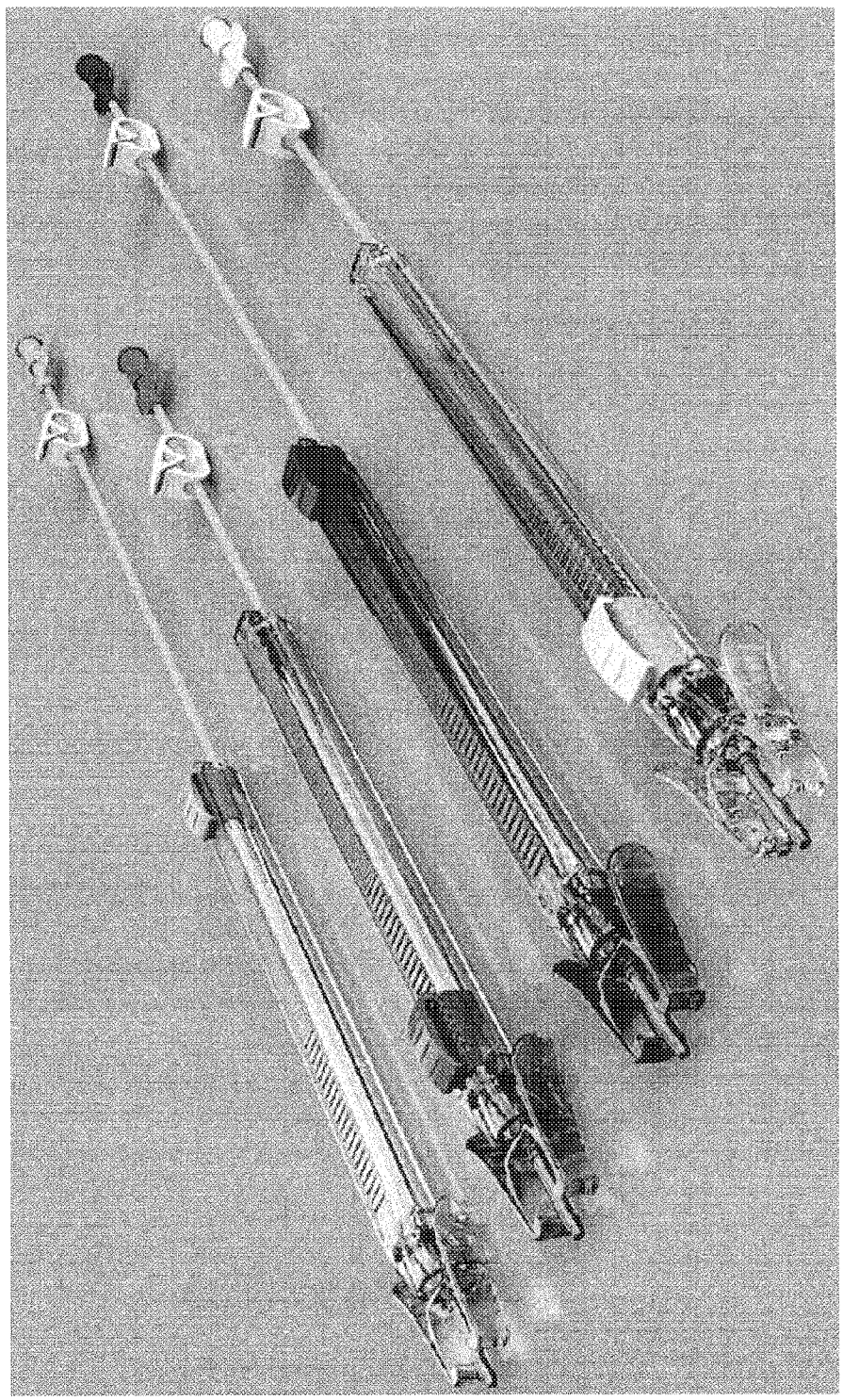
Figure 56:
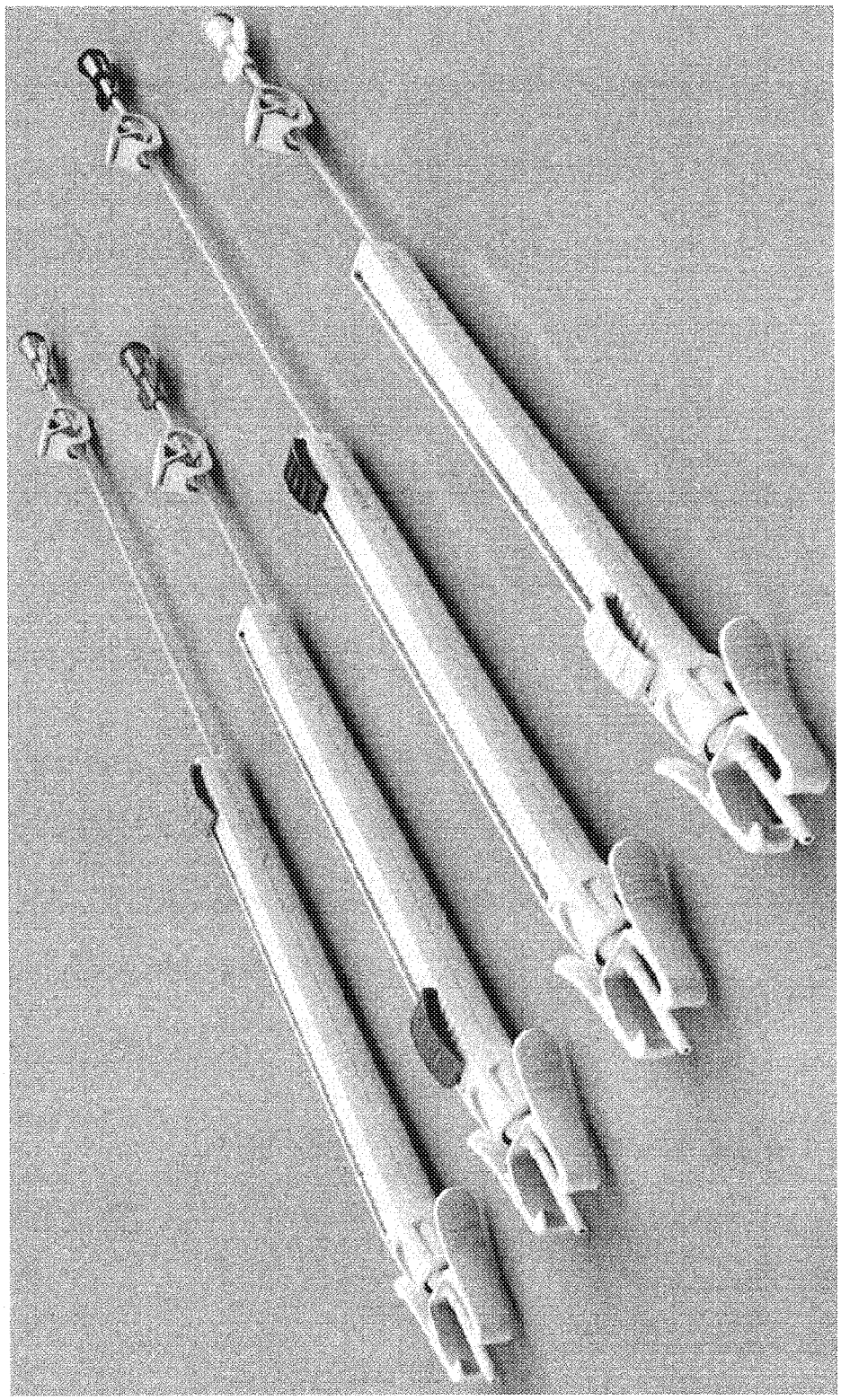
Figure 57:
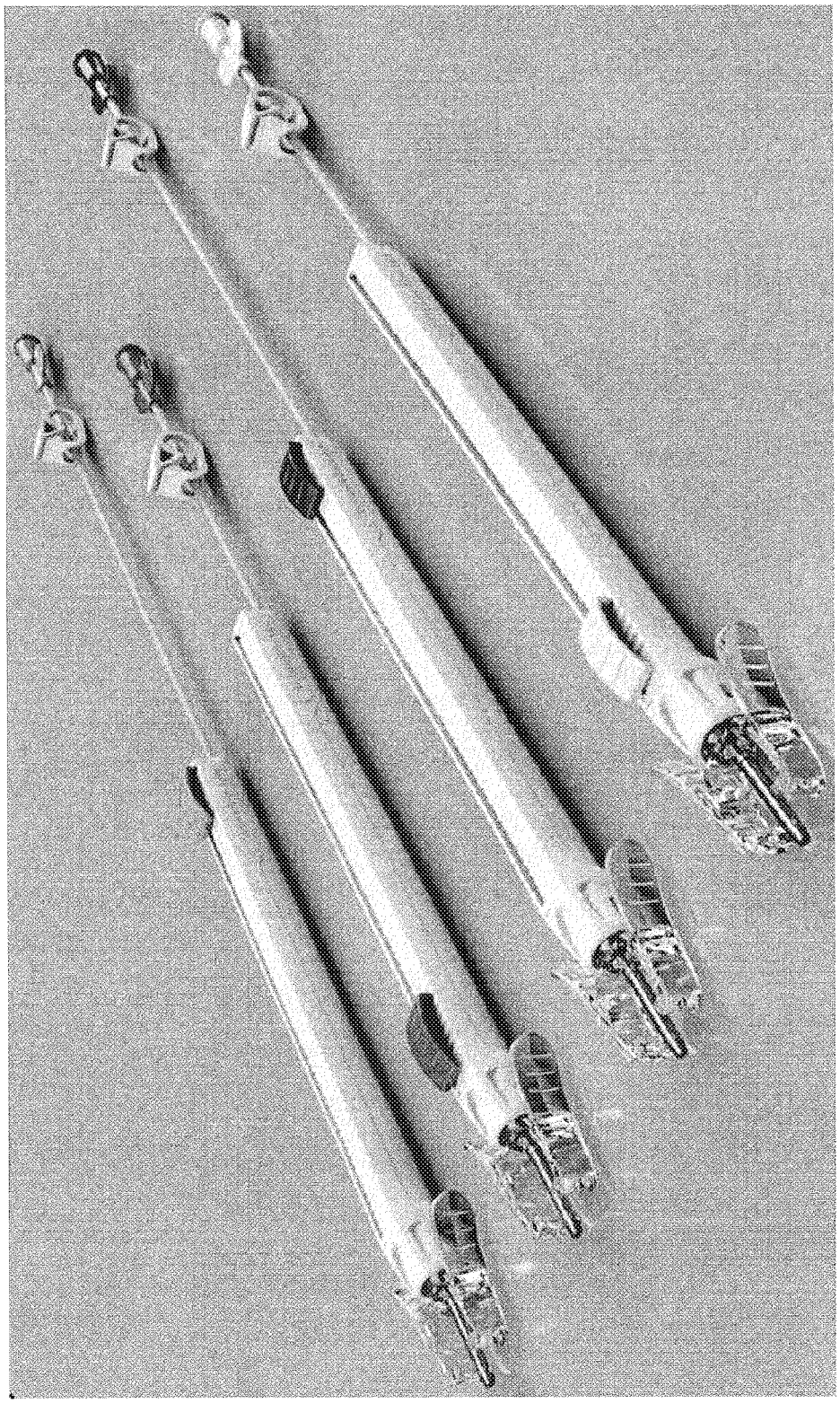
Figure 58:
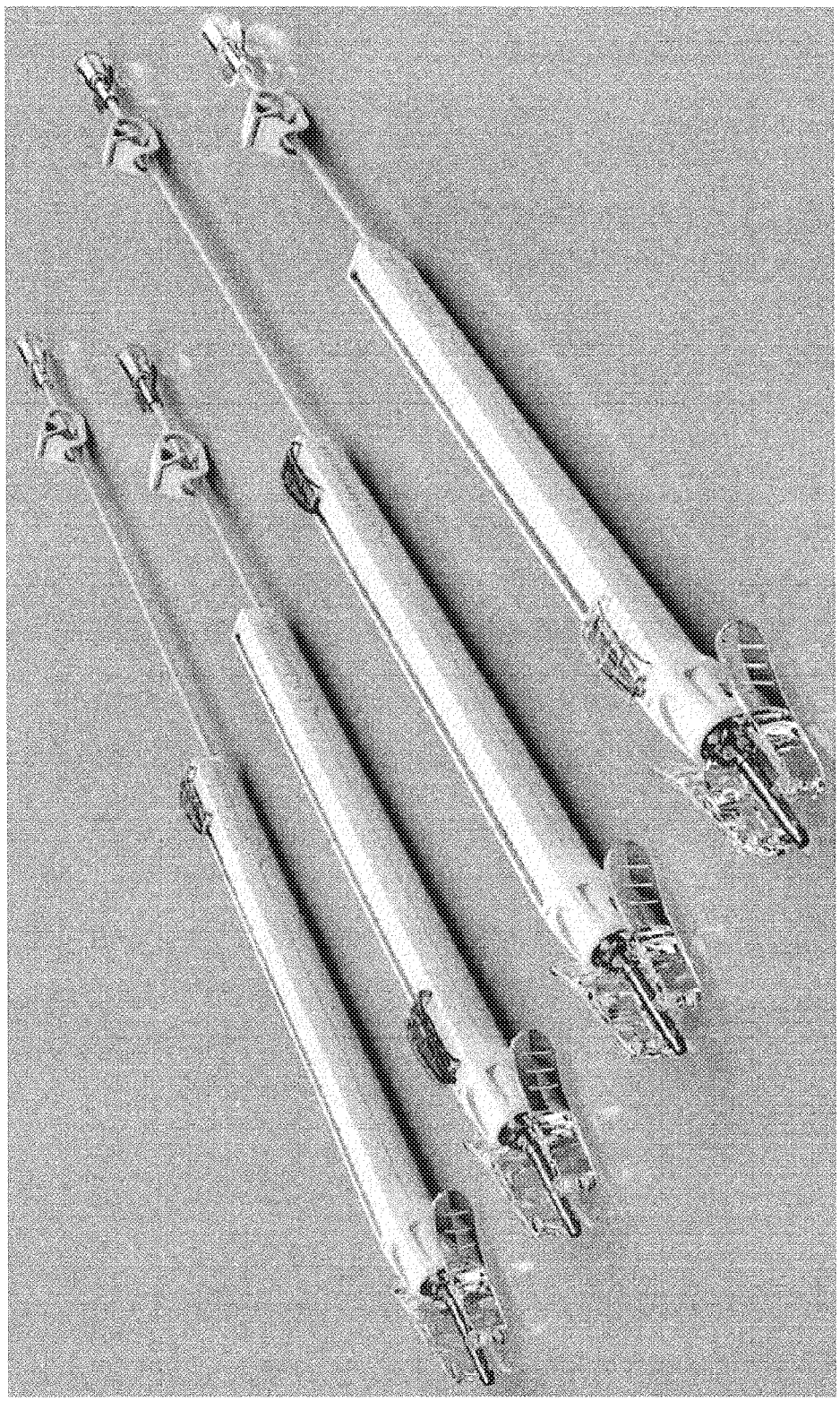
Figure 59:
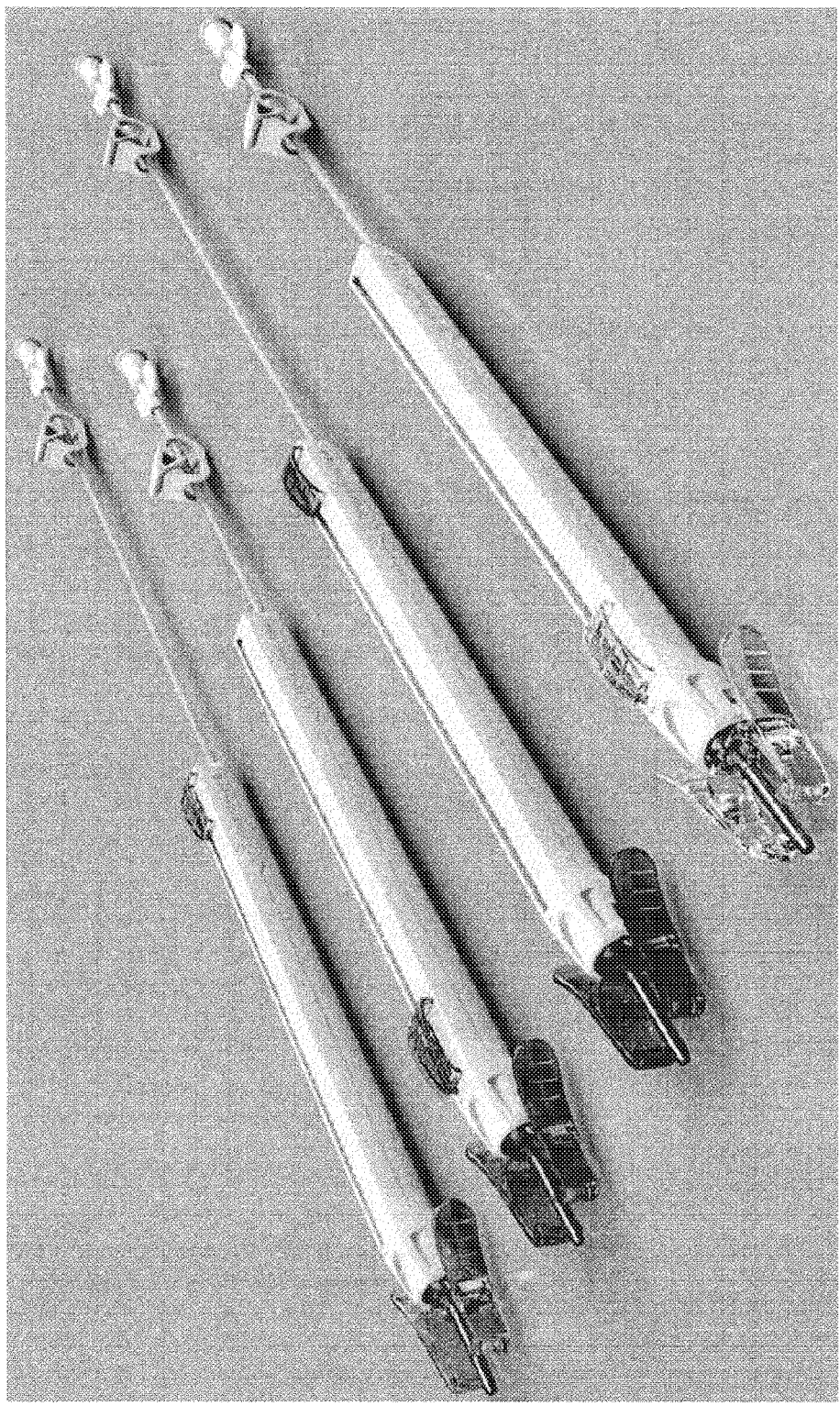
Figure 60:
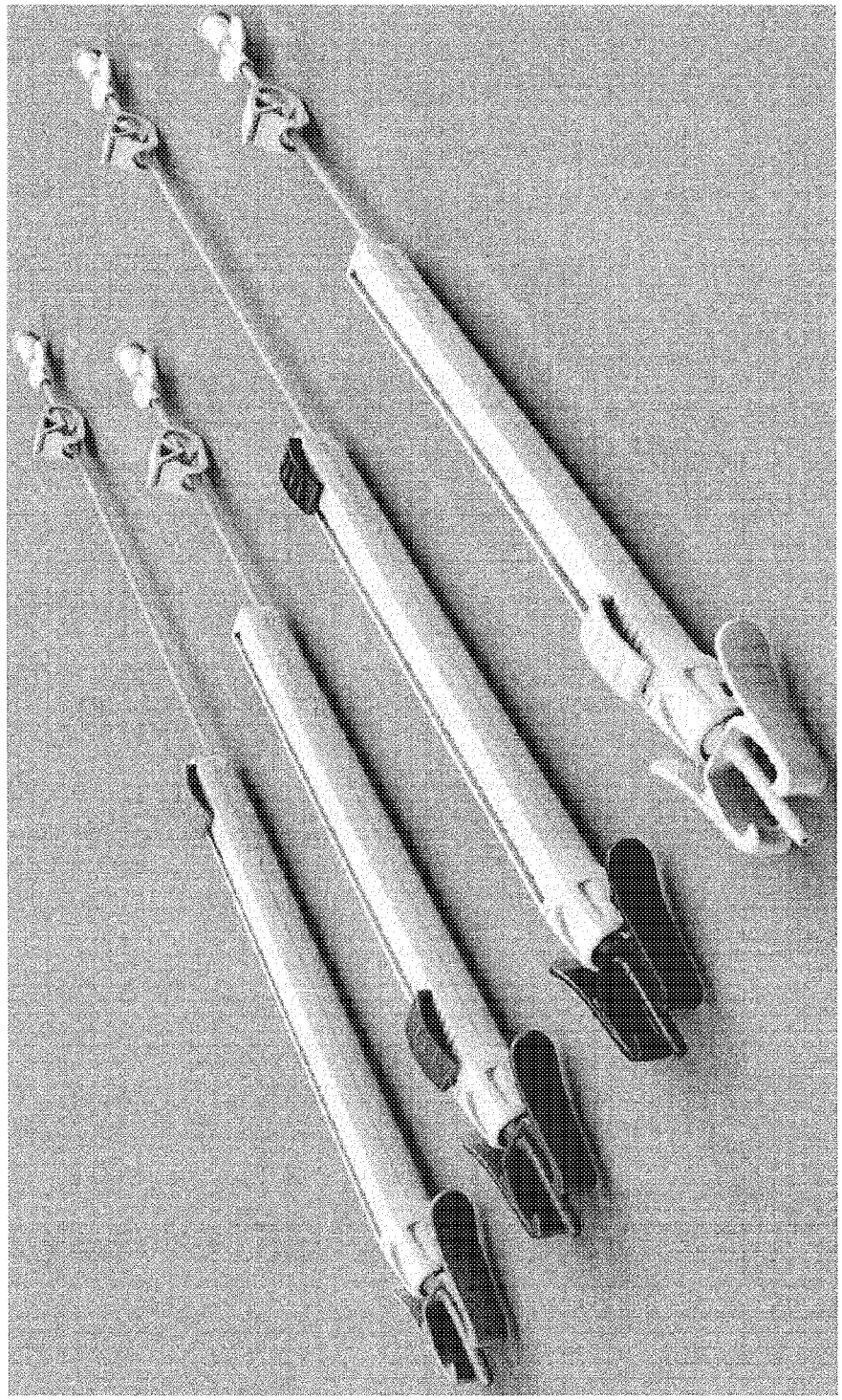

As shown, for example, in FIGS. 46-52, any suitable portion of a transfer device such as, for example, the transfer device 400 described above, can have a substantially uncolored and at least partially transparent (clear or light grey) introducer (e.g., the introducer 410) and a color coded partially transparent or opaque lock (e.g., the lock 450) and/or actuator (e.g., the actuator 470). In some embodiments, a transfer device can also include a color coded partially transparent or opaque coupler (e.g., the coupler 379 included in the transfer device 300), as shown in FIGS. 50-52. In some embodiments, a transfer device can include a white, opaque lock, as shown in FIG. 52. In some embodiments, such as those shown in FIGS. 53-55, an introducer, lock, actuator, and/or coupler can each be color coded and partially transparent or color coded and opaque, or a combination thereof. In some embodiments, such as those shown in FIGS. 56-61, a transfer device can include a white, opaque introducer and any suitable combination of color-coding described above.

While embodiments are particularly shown and described herein, various changes in form and details may be made. Any of the aspects and/or features of the embodiments shown and described herein can be modified to affect the performance thereof. For example, the ribs in the set of ribs 436 of the introducer 410 and the actuator 470 can have any suitable shape, size, configuration, and/or arrangement to produce a desired set of characteristics associated with the movement of the actuator 470 relative to the introducer 410, as described above. By way of another example, any of the components of the transfer device 400 can be formed from any suitable material that can result in a desired hardness, durometer, and/or stiffness of that component. As another example, the size and/or shape of the transfer device 400 can be increased or decreased based on a desired usage. For example, in some embodiments, a transfer device having a size that is smaller than the transfer device 400, but otherwise being substantially similar in form and/or function to the transfer device 400 can be used with or for pediatric patients.

Where methods and/or schematics described above indicate certain events and/or flow patterns occurring in certain order, the ordering of certain events and/or flow patterns may be modified. Additionally certain events may be performed concurrently in parallel processes when possible, or may be performed sequentially. Moreover, while the fluid transfer devices 300 and/or 400 are described above as being used in the method 50, in other instances, any suitable device can be used in any of the methods described herein (including the method 50). For example, in some embodiments, a user can manipulate a catheter to advance the catheter from a first position to a second position relative to an indwelling peripheral intravenous line, as described above with reference to the method 50. In such instances, the catheter can be independent of a fluid transfer device such as the fluid transfer devices 300 and/or 400. In other words, a separate and/or independent catheter can be used in any of the methods described herein including, for example, the method 50. Said another way, a fluid transfer device that includes only a catheter can be used in any of the methods described herein including, for example, the method 50.

What is claimed is:

1. A method, comprising:
   coupling a fluid transfer device to an indwelling peripheral intravenous line at least partially disposed in a vein of a patient, the fluid transfer device including at least a catheter configured to be moved relative to the indwelling peripheral intravenous line;
   moving the catheter from a first position, in which the catheter is proximal to the indwelling peripheral intravenous line, to a second position, in which at least a portion of the catheter is disposed within the indwelling peripheral intravenous line such that a distal surface of the catheter is disposed at a predetermined distance from a distal tip of the indwelling peripheral intravenous line, the predetermined distance based at least in part on a predefined average distance of a plurality of distances, each distance from the plurality of distances being along a vein from a plurality of veins calculated between a position associated with a distal tip of a peripheral intravenous line and a position associated with a branch vessel having a volumetric flow rate that is greater than a volumetric flow rate threshold;

transferring a volume of blood via the catheter from the vein to a fluid reservoir in fluid communication with the catheter;

moving the catheter from the second position toward the first position after transferring a desired volume of blood to the fluid reservoir; and decoupling the fluid transfer device from the indwelling peripheral intravenous line after moving the catheter from the second position toward the first position.

2. The method of claim 1, wherein a determining of the venous anatomy associated with each vein from the plurality of veins being based at least in part on ultrasonic imaging of each vein from the plurality of veins, each distance from the plurality of distances being determined based on images resulting from the ultrasonic imaging.

3. The method of claim 1, wherein the predetermined distance is at least partially based on at least one of a valve being proximally disposed within the vein relative to a position within the vein associated with a distal tip of a peripheral intravenous line or a branch vessel coupled to the vein in a proximal position along the vein relative to the position within the vein associated with the distal tip of the peripheral intravenous line.

4. The method of claim 3, wherein the moving of the catheter to the second position includes placing the distal surface of the catheter in a distal position relative to the distal tip of the indwelling peripheral intravenous line at the predetermined distance such that at least one of the valve or the branch vessel is disposed at a position along the vein between the distal surface of the catheter and the distal tip of the indwelling peripheral intravenous line.

5. The method of claim 1, wherein the distal tip of the peripheral intravenous line is disposed in a first compartment of the vein, the moving of the catheter to the second position includes placing the distal surface of the catheter in a distal position relative to a valve within the vein such that the distal surface of the catheter is disposed within a second compartment of the vein separated from the first compartment of the vein by at least the valve, the second compartment having a volumetric flow rate greater than a volumetric flow rate of the first compartment.

6. The method of claim 1, wherein the indwelling peripheral intravenous line includes a hub opposite the distal tip of the indwelling peripheral intravenous line, the moving of the catheter to the second position includes placing the distal surface of the catheter in a distal position relative to the hub and one of a proximal position relative to the distal tip of the indwelling peripheral intravenous line or flush with the distal tip of the indwelling peripheral intravenous line.

7. The method of claim 1, wherein the predetermined distance is between about 0.0 millimeters (mm) and about 50.0 mm.

8. The method of claim 1, wherein the catheter is in a distal most position relative to the indwelling peripheral intravenous line when the catheter is in the second position such that the predetermined distance is about 30.0 mm.

9. The method of claim 1, wherein the predetermined distance is based at least in part on a length of the indwelling peripheral intravenous line.

10. A method, comprising:

coupling an introducer to an indwelling peripheral intravenous line at least partially disposed in a vein of a patient;

moving a catheter from a first position, in which the catheter is at least partially disposed in the introducer and proximal to the indwelling peripheral intravenous line, to a second position, in which a portion of the catheter is disposed within the indwelling peripheral intravenous line such that (1) a distal surface of the catheter is disposed within the vein and distally spaced a predetermined distance from a distal tip of the indwelling peripheral intravenous line, and (2) at least one of a valve disposed within the vein, an obstruction within the vein, or a branch vessel coupled to the vein is disposed between the distal tip of the indwelling peripheral intravenous line and the distal surface of the catheter, wherein the predetermined distance is based at least in part on a predefined average distance between the distal tip of the indwelling peripheral intravenous line and at least one of a valve disposed within the vein or a branch vessel in fluid communication with the vein;

transferring a volume of blood via the catheter from the vein to a fluid reservoir in fluid communication with the catheter;

moving the catheter from the second position toward the first position after transferring a desired volume of blood to the fluid reservoir; and decoupling the fluid transfer device from the indwelling peripheral intravenous line after moving the catheter from the second position toward the first position.

11. The method of claim 10, wherein the predetermined distance is a distance between about 15.0 millimeters (mm) and about 50.0 mm.

12. The method of claim 10, wherein the predetermined distance is about 30.0 mm.

13. The method of claim 10, wherein a volumetric flow rate through the catheter is based at least in part on the length of the catheter, the length of the catheter being such that the volumetric flow rate through the catheter is greater than a volumetric flow rate threshold.

14. The method of claim 10, further comprising:

coupling an adapter to the indwelling peripheral intravenous line, the coupling of the introducer to the indwelling peripheral intravenous line being such that the adapter is disposed between the introducer and the indwelling peripheral intravenous line, the catheter configured to extend through the adapter and the indwelling peripheral intravenous line when the catheter is placed in the second position.

15. The method of claim 10, wherein the introducer and the catheter are included in a fluid transfer device, the fluid transfer device including an actuator coupled to the catheter and configured to move relative to the introducer, the moving the catheter from the first position to the second position includes moving the actuator relative to the introducer from a first actuator position to a second actuator position.

16. A method, comprising:

coupling an introducer to an indwelling peripheral intravenous line at least partially disposed in a vein of a patient;

moving a catheter from a first position, in which the catheter is at least partially disposed in the introducer and proximal to the indwelling peripheral intravenous line, to a second position, in which a portion of the catheter is disposed within the indwelling peripheral intravenous line such that a distal surface of the catheter is spaced apart from a distal tip of the indwelling peripheral intravenous line by at least a first distance, the first distance based at least in part on a predefined average distance between the distal tip of the indwelling peripheral intravenous line and at least one of a valve disposed within the vein or a branch vessel in fluid communication with the vein; and transferring a volume of blood via a lumen of the catheter from the vein to a fluid reservoir in fluid communication with the catheter in response to a negative pressure within the lumen, a volumetric flow rate through the catheter in response to the negative pressure when the distal surface of the catheter is in the second position being greater than a volumetric flow rate through the catheter in response to the negative pressure when the catheter is in a position in which the distal surface of the catheter is spaced apart from the distal tip of the indwelling peripheral intravenous line by a second distance less than the first distance.

17. The method of claim 16, wherein the second position of the catheter is a distal most position of the catheter.

18. The method of claim 16, wherein the first distance is a distance between about 15.0 millimeters (mm) and about 50.0 mm.

19. The method of claim 16, wherein the first distance is about 30.0 mm.

20. The method of claim 16, wherein the volumetric flow rate through the catheter is based at least in part on a length of the catheter, the length of the catheter being such that the volumetric flow rate through the catheter is greater than a volumetric flow rate threshold.

21. The method of claim 16, wherein the volumetric flow rate through the catheter is based at least in part on a volumetric flow rate through the vein, the catheter has a length such that when the catheter is in the second position, the distal surface of the catheter is disposed within a portion of the vein having a volumetric flow rate greater than a volumetric flow rate threshold, a portion of the indwelling peripheral intravenous line disposed in the vein reduces a volumetric flow rate through a portion of the vein defined between the distal tip of the indwelling peripheral intravenous line and the first distance from the distal tip of the indwelling peripheral intravenous line.

22. The method of claim 16, wherein the moving of the catheter to the second position is such that at least one of a valve within the vein or a branch vessel coupled to the vein is disposed at a position along the vein between the distal surface of the catheter and the distal tip of the indwelling peripheral intravenous line.

23. The method of claim 16, further comprising:

coupling an adapter to the indwelling peripheral intravenous line, the coupling of the introducer to the indwelling peripheral intravenous line being such that the adapter is disposed between the introducer and the indwelling peripheral intravenous line, the catheter configured to extend through the adapter and the indwelling peripheral intravenous line when the catheter is placed in the second position.

24. The method of claim 16, wherein the introducer includes a lock disposed at a distal end portion of the introducer, the coupling of the introducer to the indwelling peripheral intravenous line includes coupling the lock to at least one of a hub of the indwelling peripheral intravenous line or an adapter coupled to the hub of the indwelling peripheral intravenous line to operably couple the introducer to the indwelling peripheral intravenous line.

25. The method of claim 16, wherein the introducer and the catheter are included in a fluid transfer device, the fluid transfer device including an actuator coupled to the catheter and configured to move relative to the introducer, the moving the catheter from the first position to the second position includes moving the actuator relative to the introducer from a first actuator position to a second actuator position.

* * * * *